US011357890B2

(12) United States Patent
de Peppo et al.

(10) Patent No.: US 11,357,890 B2
(45) Date of Patent: Jun. 14, 2022

(54) CUSTOMIZED HYBRID BONE-IMPLANT GRAFTS

(71) Applicant: New York Stem Cell Foundation, Inc., New York, NY (US)

(72) Inventors: Giuseppe Maria de Peppo, New York, NY (US); Martina Sladkova, New York, NY (US)

(73) Assignee: New York Stem Cell Foundation, Inc., New York, NY (US)

( * ) Notice: Subject to any disclaimer, the term of this patent is extended or adjusted under 35 U.S.C. 154(b) by 0 days.

(21) Appl. No.: 16/088,640

(22) PCT Filed: Mar. 31, 2017

(86) PCT No.: PCT/US2017/025390
§ 371 (c)(1),
(2) Date: Sep. 26, 2018

(87) PCT Pub. No.: WO2017/173280
PCT Pub. Date: Oct. 5, 2017

(65) Prior Publication Data
US 2019/0105429 A1    Apr. 11, 2019

Related U.S. Application Data

(60) Provisional application No. 62/317,165, filed on Apr. 1, 2016.

(51) Int. Cl.
*A61F 2/28* (2006.01)
*A61L 27/38* (2006.01)
(Continued)

(52) U.S. Cl.
CPC .......... *A61L 27/3834* (2013.01); *A61K 35/28* (2013.01); *A61K 35/32* (2013.01);
(Continued)

(58) Field of Classification Search
CPC .............. A61F 2/28; A61F 2002/30971; A61F 2/30965; A61B 2017/00964; A61B 2017/00933
See application file for complete search history.

(56) References Cited

U.S. PATENT DOCUMENTS 5,899,939 A    5/1999  Boyce et al.
6,143,293 A   11/2000  Weiss
(Continued)

FOREIGN PATENT DOCUMENTS

WO    WO 1996/040002 A1    12/1996
WO    WO 1999/048541 A1     9/1999
(Continued)

OTHER PUBLICATIONS

CT Scan (CAT Scan, Computerized Tomography) Imaging Procedure, Jun. 13, 2018; retrieved from the internet Dec. 7, 2018: www.medicinenet.com /cat scan/article.htnn#what is a ct scan, 4 pages.
(Continued)

Primary Examiner — Jason-Dennis N Stewart
(74) Attorney, Agent, or Firm — Goodwin Procter LLP

(57) ABSTRACT

The present invention provides customized hybrid bone-implant grafts and a method of manufacture thereof.

22 Claims, 26 Drawing Sheets

(51) Int. Cl.

| | | |
|---|---|---|
| *A61L 27/06* | (2006.01) | |
| *A61L 27/36* | (2006.01) | |
| *A61K 35/28* | (2015.01) | |
| *A61K 35/545* | (2015.01) | |
| *A61K 35/44* | (2015.01) | |
| *A61K 35/32* | (2015.01) | |
| *C12N 5/071* | (2010.01) | |

(52) U.S. Cl.
CPC .......... *A61K 35/44* (2013.01); *A61K 35/545* (2013.01); *A61L 27/06* (2013.01); *A61L 27/3608* (2013.01); *A61L 27/3691* (2013.01); *A61L 27/3886* (2013.01); *C12N 5/0697* (2013.01); *A61F 2/2803* (2013.01); *A61L 2430/02* (2013.01); *A61L 2430/06* (2013.01); *C12N 2506/45* (2013.01)

(56) References Cited

U.S. PATENT DOCUMENTS

| | | | |
|---|---|---|---|
| 6,472,202 B1 | 10/2002 | Banes | |
| 8,398,714 B2 | 3/2013 | Boiangiu et al. | |
| 8,895,046 B2 | 11/2014 | Xuenong et al. | |
| 8,926,699 B2 | 1/2015 | Burkinshaw | |
| 9,456,893 B2 | 10/2016 | Ling | |
| 2003/0100107 A1 | 5/2003 | Peschle | |
| 2006/0253192 A1* | 11/2006 | Atala | A61L 27/3839 623/2.13 |
| 2006/0257447 A1 | 11/2006 | Hinds et al. | |
| 2008/0033548 A1 | 2/2008 | Xuenong et al. | |
| 2010/0003222 A1 | 1/2010 | Yayon | |
| 2010/0040584 A1* | 2/2010 | Melero-Martin | A61L 27/3804 424/93.7 |
| 2010/0249931 A1 | 10/2010 | Laurencin et al. | |
| 2010/0303911 A1 | 12/2010 | Sheardown et al. | |
| 2011/0151400 A1 | 6/2011 | Boiangiu et al. | |
| 2012/0035742 A1 | 2/2012 | Vunjak-Novakovic et al. | |
| 2012/0209403 A1 | 8/2012 | Morrison et al. | |
| 2013/0017232 A1 | 1/2013 | Varghese | |
| 2013/0030547 A1 | 1/2013 | Burkinshaw | |
| 2013/0030548 A1* | 1/2013 | Ling | A61F 2/105 623/23.72 |
| 2013/0046392 A1* | 2/2013 | Venu | A61L 27/32 623/23.53 |
| 2013/0274892 A1 | 10/2013 | Lelkes et al. | |
| 2013/0344114 A1 | 12/2013 | Chang et al. | |
| 2014/0030762 A1 | 1/2014 | De Plano et al. | |
| 2014/0147419 A1 | 5/2014 | Novakovic et al. | |
| 2014/0178455 A1* | 6/2014 | Nukavarapu | A61L 27/58 424/426 |
| 2015/0289889 A1 | 10/2015 | Altschuler et al. | |

FOREIGN PATENT DOCUMENTS

| | | |
|---|---|---|
| WO | WO 2006/109137 A1 | 10/2006 |
| WO | WO 2013/010283 A2 | 1/2013 |
| WO | WO 2015/103149 A1 | 7/2015 |

OTHER PUBLICATIONS

European Examination Report dated Apr. 9, 2019, regarding EP14 877 521.6.

Datta, N. et al.: "*Effect of bone extracellular matrix synthesized in vitro on the osteoblastic differentiation of marrow stromal cells*"; Biomaterials, Mar. 1, 2005, vol. 26, No. 9, pp. 971-977, XP027767796.

Extended European Search Report dated Oct. 31, 2019, regarding EP 17 77 6781.

Griffin, Kaitlyn S. et al.: "*Evolution of Bone Grafting: Bone Grafts and Tissue Engineering Strategies for Vascularized Bone Regeneration*", Clinic Rev Bone Miner Metab, Sep. 2, 2015, vol. 13, pp. 232-244, XP035951944.

Lovati, Arianna B. et al.: "*In vivo evaluation of bone deposition in macroporous titanium implants loaded with mesenchymal stem cells and strontium-enriched hydrogel*"; J. of Biome Mater Res Part B Feb. 1, 2015, vol. 103B, pp. 448-456. XP055635131.

Kohl et al., Proc Am Thorac Soc, vol. 2, pp. 470-476, 2005 (Year: 2005).

Walter et al., RadioGraphics, Mar. 1988, vol. 8, No. 2, pp. 327-348 (Year: 1988).

Chen et al., "Anchoring Dental Implant in Tissue-Engineered Bone Using Composite Scaffold: A Preliminary Study in Nude Mouse Model," *J. Oral Maxillofac. Surg.* (2005), 63:586-591, American Association of Oral and Maxillofacial Surgeons.

Yu et al., "Bioreactor-Based Bone Tissue Engineering: The Influence of Dynamic Flow on Osteoblast Phenotypic Expression and Matrix Mineralization," *PNAS* (2004), 101(31):11203-11208, The National Academy of Sciences of the USA.

De Peppo et al.: "*Cultivation of Human Bone-Like Tissue from Pluripotent Stem Cell-Derived Osteogenic Progenitors in Perfusion Bioreactors*"; Methods Mol Biol., Nov. 27, 2013, vol. 1202, pp. 173-184.

Eldesoni, Karam et al.: "*High Calcium Bioglass Enhances Differentiation and Survival of Endothelial Progenitor Cells, Inducing Early Vascularization in Critical Size Bone Defects*"; PLOS ONE, Nov. 2013, vol. 8, No. 11, e79058.

Extended European Search Report dated Jul. 7, 2017, regarding EP 14 87 7521.6.

Grayson at al.: "*Effects of Initial Seeding Density and Fluid Perfusion Rate on Formation of Tissue-Engineered Bone*"; Tissue Eng Part A, Jul. 11, 2008, vol. 14, pp. 1809-1820.

International Search Report dated Jun. 22, 2017, regarding PCT/US2017/025390.

International Search Report dated Aug. 22, 2016, regarding PCT/US2016/025601.

International Search Report dated Feb. 16, 2016, regarding PCT/US2015/064076.

International Search Report dated Apr. 6, 2015 regarding PCT/US2014/072579.

Japanese Office Action dated Aug. 23, 2018, regarding JP 2016-543600.

* cited by examiner

A.

B.

CUSTOMIZED HYBRID BONE-IMPLANT GRAFTS

CROSS-REFERENCE TO RELATED APPLICATIONS

This application is a 35 USC § 371 National Stage application of International Application No. PCT/US2017/025390 filed Mar. 31, 2017, now pending; which claims the benefit under 35 USC § 119(e) to U.S. Application Ser. No. 62/317,165 filed Apr. 1, 2016. The disclosure of each of the prior applications is considered part of and is incorporated by reference in the disclosure of this application.

BACKGROUND INFORMATION

Field of the Invention

The present invention relates generally to tissue engineering, and more particularly to customized hybrid bone-implant grafts.

Background of the Invention

The global dental implant and prosthetics market was valued at $11.9 billion in 2014, and is expected to grow at a compound annual growth rate (CAGR) of 7.2% during the forecast period of 2015 to 2020. The massive market growth, at least in part, is driven by the increase in life expectancy, with higher incidence of skeletal trauma and diseases, and rising number of edentate people. Every year millions of patients achieve improved quality of life through implantation of biomaterials and medical devices. Materials for maxillofacial and skeletal reconstructions vary depending on the specific application and include metals, ceramics, and composite materials.

Metals and alloys are commonly used for their good mechanical properties and ability, under favorable conditions, to form a stable bond with the surrounding tissue—osseointegration. The quality of this bond is highly dependent on the surface characteristics of the implant material at macro-, micro- and nano-scale. Yet, full integration of prosthetic implants takes time, and often fails in clinical situations characterized by poor bone quality, compromised regenerative capacity, and other factors that are still unclear. Intense research efforts are thus necessary to develop materials that are cost-effective, safe, and optimal for each patient in each clinical situation.

SUMMARY OF THE INVENTION

Some of the main aspects of the present invention are summarized below. Additional aspects of the present invention are described in the Detailed Description of the Invention, Examples, Drawings and Claims sections of this patent application. The description in each of the sections of this patent application is intended to be read in conjunction with the other sections. Furthermore, the various embodiments described in each of the sections of this patent application can be combined in various different ways, and all such combinations are intended to fall within the scope of the present invention.

Advances in stem cell biology, material science and engineering have recently facilitated the development of functional tissue substitutes in the laboratory using progenitor cells derived from induced pluripotent stem cells in combination with biomimetic approaches of tissue development and perfusion bioreactor systems. Building on these discoveries, the present invention is based in part on the finding that tissue grafts engineered in vitro can be used to generate hybrid tissue-implant grafts for implantation. For example, functional bone grafts engineered from induced pluripotent stem cells (iPSC) using a biomimetic approach of bone development may be combined with an implant material to gerated such hybrid implants. As described herein, the present invention provides methods, compositions, systems and kits that can be used to facilitate development of improved or novel grafts suitable for or compatible with clinical applications, such as implantation into a subject.

As such, the present invention provides a hybrid bone-implant graft comprising: a) an implant material; and b) an engineered bone tissue graft having a scaffold, wherein the graft is composed of cells seeded on the scaffold and cultured to promote formation of a stable bond between the implant and engineered tissue.

In another aspect, the invention provides a kit for generating a hybrid bone-implant graft comprising: a) one or more populations of tissue forming cells; b) two or more scaffolds; and c) an implant material.

In another aspect, the invention provides a method of preparing a hybrid bone-implant graft, the method comprising culturing one or more populations of cells on a scaffold to form a tissue graft, wherein the tissue graft is cultured in vitro with an implant material to promote formation of a stable bond between the implant and engineered tissue.

In some embodiments the tissue graft comprises a cell culture scaffold. In some embodiments the scaffold has a thickness of less than one centimeter or a thickness of from about 0.3 millimeters to about 10 millimeters. In some embodiments, the scaffold consists essentially of decellularized bone tissue, for example bovine bone tissue or human bone tissue. In some embodiments the scaffold comprises a natural material or a synthetic material or a combination of natural and synthetic materials. In some embodiments the scaffold comprises one or more natural or synthetic materials. Non-limiting examples of synthetic materials include ceramic, cement, or polymer composite. In some embodiments the scaffold material is functionalized, for example, to enhance performance under desired testing conditions. In some embodiments the scaffold comprises functionalized material, for example where the material has been modified with cytokines, growth factors, synthetic molecules, and the like. In some embodiments the scaffold comprises an opening to accommodate culturing of the implant material with the tissue graft. In some embodiments more than one implant material is assessed. In such embodiments more than one scaffold may be used (for example one scaffold for each implant material) and/or the scaffold may be configured to accommodate more than one test sample or device, for example a scaffold having more than one openings to accommodate culturing of more than one implant material with the tissue grafts.

In some embodiments, the scaffold may have any desired size and shape for personalized reconstructions. Any scaffold described herein, or made by a method described herein, may be used in conjunction with any implant material known in the art or described in this disclosure.

In some embodiments the culturing of the tissue graft with an implant material is carried out under static culture conditions or dynamic culture conditions. In some embodiments the culturing is carried out for about 2, about 3, about 4, about 5, about 6, about 7, about 8, about 9, or about 10 weeks. In some embodiments the culturing is carried out for more than 10 weeks. In some embodiments the culturing is carried out until a desired or suitable amount of mature tissue has been formed. In some embodiments the culturing is carried out in a culture vessel, for example, a perfusion bioreactor such as those described herein. In some embodiments the culture vessel comprises a bioreactor, a spinner flask, a rotating vessel, a perfusion or compressive system, or any combination thereof. Culture conditions are further described herein, including direct perfusion and press fit conditions.

In some embodiments the tissue graft comprises cells derived from stem cells or progenitor cells; for example induced pluripotent stem cells, or any other tissue-forming cells described herein. In some embodiments the tissue graft is a bone graft. In some embodiments the tissue graft is vascularized. Tissue grafts and methods for preparing such tissue graft, including bone grafts and vascularized grafts, are described herein. The present invention may comprise any tissue described herein, including any tissue graft, tissue sample, tissue segment, or tissue portion described herein, or any tissue prepared by any method described herein.

In some embodiments of the present invention the implant material is a device, or a portion of a device. In embodiments, the device is a medical device, including but not limited to a class I medical device, a class II medical device or a class III medical device, and/or a medical device as defined in Section 201(h) of the Federal Food, Drug, and Cosmetic Act (FDCA) as "an instrument, apparatus, etc., that is intended for use in the diagnosis or treatment of disease or is intended to affect the structure or any function of man or other animals and which does not achieve its primary intended purposes through chemical action and is not dependent upon being metabolized for the achievement of its primary intended purposes." In some embodiments an implant material may be a synthetic material or a natural material or a mix of synthetic and natural materials. In some embodiments an implant material may be functionalized for enhanced performance (for example, with cytokines, growth factors or synthetic molecule). In some embodiments an implant material may comprise one or more cytokines, growth factors or synthetic molecules. In some embodiments an implant material may comprise a coating on the surface of an implant or device. In such embodiments the implant material may comprise a coating on an exposed outer surface of an implant or device. In such embodiments, the internal (e.g., non-exposed) portion of the implant or device may comprise the same or different materials compared to the coating on the exposed surface, for example, the internal portion of an implant may comprise titanium and the surface coating may comprise a novel material, for example a material having a desired or specified chemistry, topography and/or surface energy, being screened for tissue compatibility.

During or after culture of an engineered tissue graft with an implant material or device, tissue compatibility may be determined by assessing or measuring properties of the tissue, and/or properties of the material or device, and/or the interaction of the tissue and the material or device. For example, response of the tissue or cells to the material or device can be determined by evaluating cell attachment, migration, viability and proliferation, the quality of tissue formed, gene expression, protein expression, mineralization (e.g. for bone), or any other desired property. In some embodiments such determinations may be carried out by evaluating cells at or near the interface of the tissue with the material or device. The interaction of the tissue with the material or device may be assessed, for example, by determining migration of the cells to or growth of cells on/around the material or device. The strength or extent of integration of the material or device may be assessed using biomechanical methods, for example a pull-out test, push-out test, removal torque test, or screw-out test. In some embodiments any molecular and/or biological response of the tissue to the implant material may be assessed. In some embodiments determining whether the implant material is compatible with the tissue graft comprises determining one or more of the following: integration of the implant material with the tissue graft; amount and/or quality of the tissue graft; interaction of the implant material with the tissue graft; migration of cells to and/or on and/or around the implant material; gene and/or protein expression in the tissue graft and in cells/tissue surrounding material; strength of the interaction of the implant material with the tissue graft; or biomechanics of the implant material. In some embodiments the determining is by computed tomography (CT), microtomography (microCT), microscopy, electron microscopy, scanning electron microscopy, immunohistochemistry, Western blot and enzymatic assays, PCR, karyotyping, histology, surface profilometry, X-ray photoelectron spectroscopy (XPS) and/or any other high-resolution characterization method. A person having ordinary skill in the art will appreciate that the methods described herein are illustrative and that a variety of other methods are known in the art and of may be used in the context of the present invention.

In some embodiments the present invention provides novel methods, compositions and devices that can be used to overcome the obstacles associated with current methods for generating functional tissue, such as bone, in vitro. In some embodiments the methods provided by the present invention utilize three-dimensional models of a particular tissue portion (e.g. a portion of tissue to be constructed, replaced, or repaired), in order to make customized tissue culture scaffolds, customized tissue grafts, and/or customized bioreactors for producing such tissue grafts. In some such embodiments the tissue culture scaffolds, tissue grafts, and/or bioreactors are designed and produced such that they have a size and shape corresponding to that of the desired tissue portion, or a segment thereof. In some embodiments the methods of the present invention involve making tissue grafts by producing two or more tissue graft segments that can then be assembled/connected to produce the final tissue graft. Such methods may be referred to herein as segmental additive tissue engineering (SATE) methods. In addition to the various different methods provided herein, the present invention also provides certain compositions and devices, including customized tissue grafts, customized tissue culture scaffolds, customized bioreactors, customized bioreactor graft chambers, and customized bioreactor graft chamber inserts. These and other aspects of the present invention are described in more detail below and throughout the present patent specification.

In some embodiments, the present invention provides various methods for preparing tissue grafts, and segments thereof (tissue graft segments).

In one such embodiment the present invention provides a method of preparing a tissue graft, the method comprising: culturing one or more populations of cells on a scaffold to form a tissue graft.

In one such embodiment, the present invention provides a method of preparing a tissue graft, comprising: obtaining a three-dimensional model of a tissue portion to be produced, replaced, or repaired.

In another such embodiment, the present invention provides a method of preparing a tissue graft, comprising: (a)

obtaining a three-dimensional model of a tissue portion to be produced, replaced, or repaired, and (b) partitioning the three-dimensional model into two or more segments (model segments).

In another such embodiment, the present invention provides a method of preparing a tissue graft, comprising: obtaining a three-dimensional model of a tissue portion to be produced, replaced, or repaired wherein the model has been partitioned into two or more segments (model segments).

In another such embodiment, the present invention provides a method of preparing a tissue graft, comprising: preparing or obtaining two or more tissue graft segments.

In another such embodiment, the present invention provides a method of preparing a tissue graft, comprising: assembling two or more tissue graft segments.

In another such embodiment, the present invention provides a method of preparing a tissue graft, comprising: (a) preparing or obtaining two or more tissue graft segments, and (b) assembling the two or more tissue graft segments to form a tissue graft.

In another such embodiment, the present invention provides a method of preparing a tissue graft, comprising: (a) obtaining a three-dimensional model of a tissue portion to be produced, replaced, or repaired, (b) partitioning the three-dimensional model into two or more model segments, (c) preparing two or more tissue graft segments, wherein each tissue graft segment has a size and shape corresponding to one of the model segments of step (b), and (d) assembling the two or more tissue graft segments to form a tissue graft.

In some embodiments the present invention provides a method of preparing a tissue graft segment (for example for use in preparing a tissue graft, as described above or elsewhere herein), wherein the method comprises: obtaining a scaffold, wherein the scaffold has a size and shape corresponding to a segment of a tissue portion to be produced, replaced, or repaired (a tissue segment) or a three dimensional model thereof (a model segment).

In some embodiments the present invention provides a method of preparing a tissue graft segment (for example for use in preparing a tissue graft, as described above or elsewhere herein), wherein the method comprises: obtaining a scaffold precursor, wherein the scaffold precursor has a size and shape corresponding to a tissue portion to be produced, replaced, or repaired (a tissue segment) or a three dimensional model thereof, and partitioning (e.g. slicing) the scaffold precursor to form two or more scaffolds, wherein the scaffold has a size and shape corresponding to a segment of a tissue portion to be produced, replaced, or repaired (a tissue segment) or a three dimensional model thereof (a model segment).

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), and (ii) applying one or more populations of cells to the scaffold.

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), (ii) applying one or more populations of cells to the scaffold, and (iii) culturing the cells on the scaffold to form a tissue graft segment.

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), (ii) applying one or more populations of cells to the scaffold, (iii) obtaining a culture vessel comprising a graft chamber configured to accommodate the scaffold, (for example having a graft chamber or graft chamber insert having an internal size and shape corresponding to the scaffold), (iv) inserting the scaffold into the graft chamber of the culture vessel, and (v) culturing the cells on the scaffold within the culture vessel to form a tissue graft segment.

In some embodiments the present invention provides a method of preparing a tissue graft segment (for example for use in conjunction with one of the methods described above or elsewhere herein), wherein the method comprises: (i) obtaining a scaffold, wherein the scaffold has a size and shape corresponding to a segment of a tissue portion to be produced, replaced, or repaired (a tissue segment) or a three dimensional model thereof (a model segment), (ii) obtaining a culture vessel comprising a graft chamber configured to accommodate the scaffold, (for example having a graft chamber or graft chamber insert having an internal size and shape corresponding to the scaffold), (iii) inserting the scaffold into the graft chamber of the culture vessel, (iv) applying one or more populations of cells to the scaffold in the graft chamber, and (v) culturing the cells on the scaffold with in the culture vessel to form a tissue graft segment.

In some embodiments, the present invention provides various methods for preparing scaffolds that may be used in the production of tissue grafts or tissue graft segments.

In one such embodiment, the present invention provides a method of preparing a scaffold precursor, comprising: obtaining a three-dimensional model of a tissue portion to be produced, replaced, or repaired, wherein the scaffold precursor has a size and shape corresponding to the tissue portion or the three dimensional model thereof.

In one such embodiment, the present invention provides a method of preparing a scaffold, comprising: obtaining a three-dimensional model of a tissue portion to be produced, replaced, or repaired, wherein the scaffold has a size and shape corresponding to a segment of the tissue portion or a segment of the three dimensional model of the tissue portion.

In another such embodiment, the present invention provides a method of preparing a scaffold, comprising: (a) obtaining a three-dimensional model of a tissue portion to be produced, replaced, or repaired, and (b) partitioning the three-dimensional model into two or more segments (model segments).

In another such embodiment, the present invention provides a method of preparing a scaffold, comprising: obtaining a three-dimensional model of a tissue portion to be produced, replaced, or repaired wherein the model has been partitioned into two or segments (model segments).

In some embodiments the present invention provides a method of preparing a scaffold, wherein the method comprises: obtaining a scaffold precursor, wherein the scaffold precursor has a size and shape corresponding to a tissue portion to be produced, replaced, or repaired, or a three dimensional model thereof, and partitioning (e.g. slicing) the scaffold precursor to form two or more scaffolds, wherein each the scaffold has a size and shape corresponding to a segment of a tissue portion to be produced, replaced, or repaired (a tissue segment) or a three dimensional model thereof (a model segment).

In some embodiments, the present invention provides various methods of preparing bioreactors, bioreactor graft chambers, or bioreactor graft chamber inserts, suitable for use in preparing the tissue grafts and/or tissue graft segments described herein.

In one such embodiment, the present invention provides a method of preparing a bioreactor, bioreactor graft chamber, or bioreactor graft chamber insert, comprising: obtaining a three-dimensional model of a tissue portion to be produced, replaced, or repaired.

In another such embodiment, the present invention provides a method of preparing a bioreactor, bioreactor graft chamber, or bioreactor graft chamber insert, comprising: (a) obtaining a three-dimensional model of a tissue portion to be produced, replaced, or repaired, and (b) partitioning the three-dimensional model into two or more segments (model segments).

In another such embodiment, the present invention provides a method of preparing a bioreactor, bioreactor graft chamber, or bioreactor graft chamber insert, comprising: obtaining a three-dimensional model of a tissue portion to be produced, replaced, or repaired wherein the model has been partitioned into two or segments (model segments).

In another such embodiment, the present invention provides a method of preparing a bioreactor, bioreactor graft chamber, or bioreactor graft chamber insert, comprising: (a) obtaining a three-dimensional model of a tissue portion to be produced, replaced, or repaired, (b) partitioning the three-dimensional model into two or more model segments, (c) preparing two or more bioreactors, bioreactor graft chambers, or bioreactor graft chamber inserts, wherein each has an internal size and shape that corresponds to the size and shape of one of the model segments of step (b).

In addition to the methods described above, numerous variations on such embodiments are envisioned and are within the scope of the present invention, including, but not limited to embodiments that combine any one or more of the methods or method steps described above, or alter the order of any of the method steps described above.

In some embodiments, the present invention provides tissue grafts, and segments thereof (tissue graft segments). For example, in some embodiments, the present invention provides tissue grafts and tissue graft segments made using any of the methods described herein.

In one embodiment the present invention provides a tissue graft comprising two or more tissue graft segments. In one embodiment the present invention provides a tissue graft comprising two or more tissue graft segments, wherein the tissue graft has a shape and size corresponding to a tissue portion to be replaced or repaired, or a three-dimensional model thereof.

In one embodiment the present invention provides a tissue graft comprising two or more tissue graft segments, wherein each tissue graft segment has a maximum thickness (i.e. at its thickest point) of from about 0.3 millimeters to about 10 millimeters.

In one embodiment the present invention provides a tissue graft comprising two or more tissue graft segments, wherein each tissue graft segment comprises tissue cells differentiated from stem cells or progenitor cells (e.g. induced pluripotent stem cells).

In one embodiment the present invention provides a tissue graft comprising two or more tissue graft segments, wherein each tissue graft segment comprises endothelial cells, such as endothelial cells differentiated from stem cells or progenitor cells (e.g. induced pluripotent stem cells).

In one embodiment the present invention provides a tissue graft comprising an implant material (i.e., titanium or steel) and two or more tissue graft segments, wherein each tissue graft segment has a maximum thickness (i.e. at its thickest point) of from about 0.3 millimeters to about 10 millimeters.

In one embodiment the present invention provides a customized bone graft comprising an implant material (i.e., titanium or steel) and two or more bone graft segments, wherein each bone graft segment has a maximum thickness (i.e. at its thickest point) of from about 0.3 millimeters to about 10 millimeters and wherein the bone graft comprises bone cells derived from stem cells or progenitor cells (e.g. induced pluripotent stem cells) and endothelial cells derived stem cells or progenitor cells (e.g. induced pluripotent stem cells).

In addition to the tissue grafts described above, numerous variations of such tissue grafts are envisioned and are within the scope of the present invention, including, but not limited to those described elsewhere in the present specification and those that combine any one or more of the elements described above or elsewhere in the application.

In some of the above embodiments, the tissue grafts or tissue graft segments are bone tissue grafts or bone tissue graft segments. In some embodiments, the tissue grafts or tissue graft segments are cartilage grafts or cartilage graft segments.

In some of the above embodiments, the tissue grafts or tissue graft segments comprise mammalian cells, such as cells from non-human primates, sheep, or rodents (such as rats or mice). In some of the above embodiments, the tissue grafts or tissue graft segments comprise human cells. In some of the above embodiments, the tissue grafts or tissue graft segments comprise one or more populations of cells derived from the same subject into which the tissue graft is to be implanted (i.e. autologous cells). In some of the above embodiments, the tissue grafts or tissue graft segments comprise one or more populations of cells derived from stem cells or progenitor cells, such as induced pluripotent stem cells.

In some of the above embodiments, the tissue grafts or tissue graft segments are vascularized. In some of the above embodiments, the tissue grafts or tissue graft segments comprise endothelial cells, such as endothelial cells derived from stem cells or progenitor cells, such as induced pluripotent stem cells.

In some of the above embodiments the tissue graft segments have a thickness of about 20 millimeters or less, or 15 millimeters or less, or 10 millimeters or less, for example at their thickest point. For example, in some of the above embodiments the tissue graft segments have a thickness of from about 0.3 millimeters to about 10 millimeters, for example at their thickest point.

In some of the above embodiments the culture vessels are bioreactors, such as direct perfusion bioreactors. In some of the above embodiments the scaffolds or tissue graft segments are placed into bioreactors under press-fit conditions. In some of the above embodiments tissue graft segments are cultured in a bioreactor under direct perfusion and/or press-fit conditions.

In some of the above embodiments the scaffolds are generated or customized using computer assisted manufacturing, three-dimensional printing, casting, milling, laser cutting, rapid prototyping, or any combination thereof.

In some of the above embodiments the bioreactors, bioreactor graft chambers, or bioreactor graft chamber inserts are generated or customized using computer assisted manufacturing, three-dimensional printing, casting, milling, laser cutting, rapid prototyping, or any combination thereof.

In some of the above embodiments, the tissue grafts comprise two or more tissue graft segments connected using a biocompatible adhesive, stitches, sutures, staples, plates, pins, screws, or any combination thereof.

In some embodiments the methods, compositions, and devices provided by the present invention, and tissues prepared therefrom, can be useful for a variety of applications including for therapeutic purposes (such as repairing pathological or traumatic tissue defects), cosmetic purposes, or in model systems for studying diseases or developing therapeutics.

BRIEF DESCRIPTION OF THE FIGURES

FIG. 4A: Three-dimensional digital model of a human femur with a digital reconstruction of a bone defect to be repaired (dark gray). FIG. 4B: Partitioning of the digital model of the bone defect shown in FIG. 4A into five model segments (dark gray). The model segments can be used to drive the manufacturing of biomaterial cell scaffolds (light gray) having a size and shape that corresponds to each of the model segments.

FIG. 5A shows an enlarged view of a single scaffold. The scaffold can be designed and manufactured based on a digital image of a portion of tissue, as described herein. FIG. 5B shows multiple scaffolds of different shapes and sizes. Multiple scaffolds can be used, for example, to prepare complementary segments of a large bone graft, as described herein.

FIG. 7A: A flow chart of an embodiment of the invention where engineered bone grafts were cultured with an implant material (titanium screw) under static culture conditions or dynamic culture conditions for 7 weeks under osteogenic conditions. The chart includes examples of methods and analyses that can be carried out to determine the biocompatibility of the implant material with the tissue, for example, cytotoxicity of the tissue, microCT, pull-out test, hard histology, and DNA content, RNA expression, and protein production and release. FIG. 7B: An example of static culture in a multi-well cell culture dish. FIG. 7C: An example of static culture in a multi-well cell culture dish. FIG. 7D: An example of a perfusion bioreactor for dynamic culture.

FIG. 13A: Undifferentiated 1013A human induced pluripotent stem cell line is positive for OCT4 (green), SOX2 (green) and TRA-1-60 (red). Nuclei are stained with DAPI (blue). Scale bar: 200 µm. FIG. 13B: Morphology of mesenchymal 1013A-derived mesenchymal progenitors (1013A-MP) and bone marrow-derived mesenchymal stem cell line 1 (BMSC1) at passage (P) 4 and P10. Scale bar: 100 µm. FIG. 13C: 1013A-MP exhibit higher proliferation potential than BMSC1 when culture over ten passages (numbers indicate cumulative days in culture during expansion). FIG. 13D: Flow cytometry characterization reveals similar surface antigen profiles for 1013A-MP and BMSC1. FIG. 13E: 1013A-MP and BMSC1 are negative when stained for OCT4 (green), SOX2 (green) and TRA-1-60 (red). Nuclei are stained with DAPI (blue). Scale bar: 50 µm. FIG. 13F: 1013A-MP and BMSC1 do not express pluripotency genes (except limited amount of ZPF42) but express several mesoderm lineage-specific genes. Data represent averages±SD (n=3, P<0.05; asterisks denote significant difference between 1013A-MP and BMSC1 lines.

FIG. 14A: Titanium mini-implant (6 mm in height and 2 mm in diameter). FIG. 14B: Construct of decellularized bone scaffold anchoring the Ti implant. FIG. 14C: Mosaic image generated from fluorescence micrographs showing live iPSC-MP cells (green; line 1013A) 3 days after seeding. FIG. 14D: High magnification confocal images (10x) showing live (green) and dead (red) cells at the implant-scaffold interface. FIG. 14E: Mosaic cross-section of the screening platform stained with Van Gieson picro-fuchsin 7 weeks after culture in osteogenic medium.

FIG. 16A: A thread is made perpendicularly to the center of the scaffolds using a M1.6 tap before insertion. FIG. 16B: Instron DynaMite 8841™ tester extracting the implant at a rate of 0.2 mm/s. FIG. 16C: Comparison between pullout force required to extract the implants after manual or mechanized insertion.

FIG. 17A: Decellularized bovine bone scaffold anchoring a titanium implant (6 mm in height, 2 mm in diameter). FIG. 17B: Mosaic image generated from fluorescence micrographs showing live iPSC-MPs (green; line 1013A) 3 days after seeding. FIG. 17C: Bottom-view high-magnification confocal image showing live (green) and dead (red) cells at the implant-scaffold interface region. FIG. 17D: Mosaic cross-section of the testing platform stained with Van Gieson picro-fuchsin 7 weeks after culture in osteogenic medium. FIG. 17E: Microcomputed tomography reconstruction of the testing platform 3 days after seeding. FIG. 17F: EDS analysis of the bone-implant interface.

DETAILED DESCRIPTION OF THE INVENTION

Figure 1:
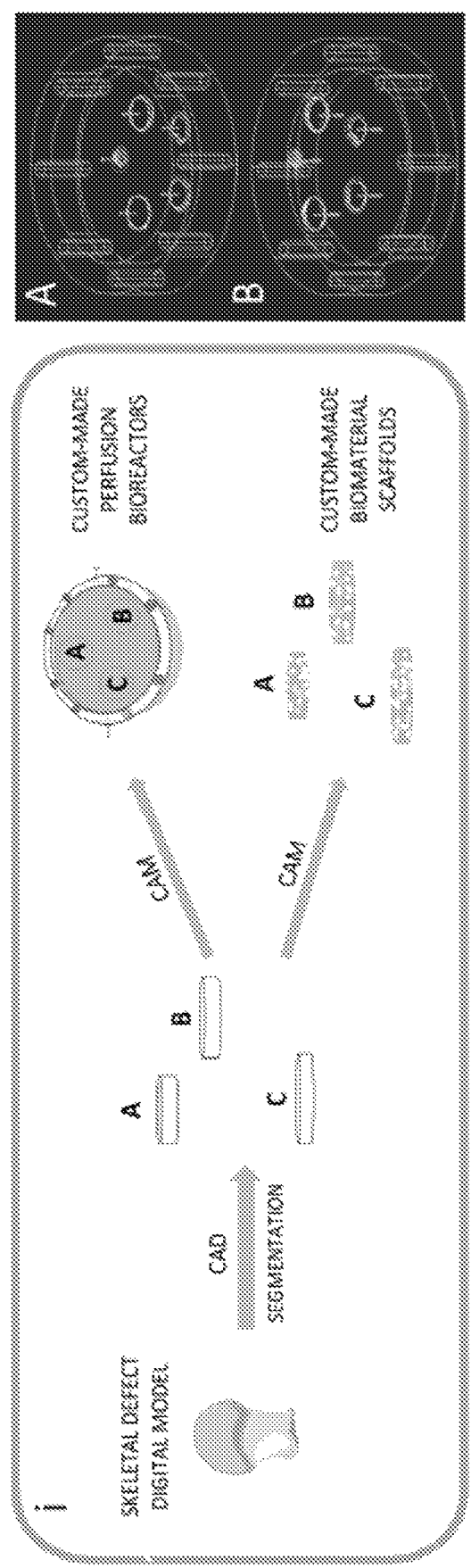
FIG. 1. (Left Panel) Digital models of skeletal defects are created, segmented (here, into three segments labeled A, B and C) and used to fabricate custom-made biomaterial scaffolds and bioreactors; (Right Panel) Example of the top part (A) and bottom part (B) of a perfusion bioreactor created using CAD software.

The present invention provides engineered tissue grafts, such as bone grafts including an implant material, such as titanium or steel, and a bone material, such as a decellularized bone scaffold seeded with bone progenitor cells and cultured to form a non-naturally occurring bone material.

Implants of the present invention have a wide range of medical applications. For example, in dentistry and orthopedics, prosthetic materials are used daily to treat edentulous people and patients affected by skeletal defects, with a global market worth many billion dollars every year. These devices have improved the life of numerous patients over the last decades, but are not effective in clinical cases characterized by limited amount of bone tissue bone amount and/or poor bone quality. For example, reconstruction of large maxillofacial defects at the interface between the skull and the teeth requires a multidisciplinary approach and often multiple surgeries resulting in long healing and rehabilitation times. New strategies are therefore required to provide the patients with safer and more effective treatment solutions, such as for example grafts and/or prostheses that replace not only the missing teeth but also the lost bone tissue to which the teeth are anchored.

It has been demonstrated that hybrid bone-implant grafts may be engineered from patient specific cells with the potential to revolutionize the way complex skeletal reconstructions are managed and treated today. In one aspect, the disclosure envisions interlocking implants (titanium or other prostheses) with anatomically shaped biomimetic scaffolds (natural or synthetic), and then seeding the scaffold-implant constructs with patient-specific cells to grow customized bone-implant grafts in-vivo or in-vitro with subsequent implantation. In embodiments, the implant materials may be interlocked/anchored after culturing the engineered tissue in-vitro, and before implantation in patients.

As described herein, in one embodiment, the inventors have anchored titanium implants (2 mm diameter, 6 mm height) into decellularized cow bone scaffolds (8 mm diameter, 3-4 mm height), and seeded the implant-scaffold constructs with human iPSC-MPs to grow living tissue around the implant. To interlock the implants with the scaffolds, a perpendicular thread was made in the center of the scaffold using a tap holding stand and a M1.6 tap, and then inserted the implants either manually or mechanically (using an ASG XPAC® SD2500 electric screwdriver with a linear torque stabilization arm at a rotation angle of 2000 degrees). The use of the ASG XPAC® SD2500 allows to place the implants consistently in the scaffolds, by controlling for example the torque value and/or rotation angle. Following placement of the implants into the scaffolds, the implant-scaffolds constructs were imaged via μCT to acquire data on the scaffold architectural features (porosity, pore size and distribution), and estimate the contact area between the implant and the scaffolds. Then after, biomechanical testing was performed, including pull-out, push-out and torque tests, using the Instron DynaMite® 8841 tester. Multiple regression analysis was performed to rule out any association between the scaffold density and architectural features and the primary implant stability achieved using different placement methods.

The use of an electric screwdriver supported by a linear torque stabilization arm is expected to allow precise placement of the implants into the scaffolds (or scaffolds seeded with cells, or scaffolds cultured with the cells for a desired period of time, i.e., 1, 2, 3, 4, 5, 6, 7, 8, 9, 10 weeks or longer).

Precise implant placement is critical to reduce fracture of the scaffold and implant motion, and is expected to result in a more uniform bone-to-implant contact area between samples. Since the bone-to-implant contact area affects the strength of interaction between the implant and the tissue in vivo (both primary and secondary), reproducible strategies of implant placement are crucial to increase the accuracy of the platform for testing implant materials in vitro.

The technology could provide better treatment options for civilians and veterans, with reduced number of surgeries, rehabilitation time, and healthcare cost associated with this medical burden. The possibility to grow personalized living bone around implants could also lead to development of bone coatings for enhanced ossointegration in patients with degenerative disorders or osteonecrosis.

In some embodiments bone grafts are engineered from induced pluripotent stem cells using a biomimetic approach of bone development in vitro (de Peppo et al., *PNAS* 110(21):8680-5 (2013)).

In some embodiments the present invention provides, in part, tissue grafts, such as bone grafts, and methods for preparing such tissue grafts, including, for example, production via bioreactor devices. In some embodiments the methods described herein can be used, for example, to generate a tissue graft, such as a bone graft, in vitro by segmental additive bone engineering (SABE) and/or segmental additive tissue engineering (SATE). In some embodiments the methods provided by the invention utilize digital models of portions of tissue, and/or custom-shaped tissue culture scaffolds, and/or customized bioreactors for growing segments of tissue in vitro. In some embodiments the size and shape of the scaffolds and bioreactors can be customized to correspond to the size and shape of the desired tissue graft using innovative engineering strategies, including, but not limited to, medical imaging, computer-assisted design (CAD), and/or computer-assisted manufacturing (CAM) strategies. In some embodiments functional tissue can be grown using any suitable cell capable of forming the desired tissue(s), such as a bone-forming cell (e.g., for preparation of a bone graft) or blood vessel-forming cell (e.g., for preparation of a vascularized tissue graft), or any cell capable of differentiating into a desired tissue-forming cell, such as a progenitor cell or pluripotent cell. In some embodiments such cells may be or may include a patient's own cells (i.e. autologous cells), or cells derived from a patient's own cells, for example, induced pluripotent stem cells. In some embodiments, following culture in bioreactors, multiple tissue segments may be assembled and secured together (e.g., in a "lego-like" approach) to form a tissue graft, for example a tissue graft corresponding to the dimensions and geometrical shape of a particular tissue portion, for example a tissue portion that needs to be replaced or reconstructed. Such techniques may be referred to herein as segmental additive tissue engineering (SATE), or, in the case of bone specifically, segmental additive bone engineering (SABE).

In some embodiments the tissue grafts and methods provided by the invention may be used to facilitate reproducible and/or large-scale fabrication of tissue or tissue substitutes for clinical applications, such as to repair or replace a tissue defect in a subject, such as a bone defect. As further described in the Examples and other sections of this application, some embodiments of the present invention can be used to make functional vascularized tissue grafts, such as functional vascularized bone grafts. Production of large, geometrically defined tissue grafts, for example using cells such as induced pluripotent stem cells, is a novel, innovative strategy at the interface between stem cell biology and medical engineering that can be used for a variety of purposes including but not limited to clinical applications, modeling of pathologies and drug screening.

Some of the main embodiments of the present invention are described in the above Summary of the Invention section of this application, as well as in the Examples, Figures and Claims. This Detailed Description section provides additional description relating to the compositions and methods of the present invention, and is intended to be read in conjunction with all other sections of the present patent application, including the Summary of the Invention, Examples, Figures and Claims sections of the present application.

Abbreviations & Definitions

The abbreviation "CAD" refers to computer-aided design.

The abbreviation "CAM" refers to computer-aided manufacture.

The abbreviation "CNC" refers to computer-numerical-control.

As used herein, the terms "cell/scaffold" and "scaffold/cell" and "cell/scaffold construct" and "cell/scaffold complex" and "scaffold/cell construct" and "scaffold/cell complex" are used interchangeably to refer to a scaffold to which cells have been applied.

As used herein, the terms "about" and "approximately," when used in relation to numerical values, mean within + or −20% of the stated value.

Additional definitions and abbreviations are provided elsewhere in this patent specification or are well known in the art.

Size and Shape Variations

As used herein, the terms "corresponding to" and "correspond to," when used in relation to any aspect of the present invention where size and shape matching of two or more elements is contemplated, can mean any of the size and shape variations described in this section. Such variations described in this section can apply equally to all aspects of the present invention where size and shape matching of two or more elements is contemplated. Such elements include, tissue portions, tissue models, tissue grafts, model segments, tissue segments, bioreactors, bioreactor chambers (e.g. bioreactor graft chambers) and inserts (e.g. bioreactor graft chamber inserts), scaffolds, scaffold precursors, cell/scaffold constructs, and any other element of the invention as described in the present application.

The illustrative embodiments in this section describe size and shape variations between two elements of the invention—a first element and a second element. However the present invention contemplates that any desired number of elements, such as three, four, five or more, may have corresponding sizes and shapes as described herein. Numerous combinations of elements are envisioned and are within the scope of the present invention, including, but not limited to those described elsewhere in the present specification and those that combine any one or more of the elements described above or elsewhere in the application. The variations described in this section apply equally to any such combinations where elements may be matched by size and shape.

In some embodiments where a first element has a size and shape corresponding to a second element, the first element has the same, or about the same, or approximately the same size and shape as the second element. In some embodiments where a first element has a size and shape corresponding to a second element, the first element has a similar or complementary size and shape as the second element.

In some embodiments where a first element has a size and shape corresponding to the size and shape of a second element, the size and shape of the first element varies by plus or minus 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, or 20% of the size and shape of the second element.

For example, in some embodiments the present invention provides a three-dimensional model having a size and shape corresponding to a particular tissue portion (e.g. a portion of tissue to be constructed, replaced, or repaired). In some embodiments the present invention provides a three-dimensional model segment having a size and shape corresponding to a cell scaffold, a bioreactor, a graft chamber, a graft chamber insert, and/or a tissue segment. In some embodiments the present invention provides a cell scaffold or cell scaffold precursor having a size and shape corresponding to a tissue portion model, a model segment, a bioreactor, a graft chamber, a graft chamber insert, a tissue segment, and/or a tissue graft. In some embodiments the present invention provides a bioreactor having a size and shape corresponding to a tissue portion model, a model segment, a scaffold, a graft chamber, a graft chamber insert, a tissue segment, and/or a tissue graft. In some embodiments the present invention provides a bioreactor graft chamber or a bioreactor graft chamber insert having a shape and size corresponding to tissue portion model, a model segment, a tissue segment, and/or a tissue graft. In some embodiments the present invention provides a tissue segment having a size and shape corresponding to a model segment, a bioreactor, a scaffold, a graft chamber, and/or a graft chamber insert. In some embodiments the present invention provides a tissue graft having a size and shape corresponding to a particular tissue portion and/or a three-dimensional model of a particular tissue portion.

Acceptable variations in size and shape can also be determined based on the desired function of the two or more elements to be matched by size and shape. In some embodiments where a first element has a size and shape corresponding to the size and shape of a second element, the first and second elements can have any suitable size and shape suitable that allows one or both elements to perform a desired function and/or have a desired property. For example, in some such embodiments a tissue graft has a size and shape corresponding to a portion of tissue to be repaired provided that the tissue graft is capable of suitably repairing the tissue portion. In some such embodiments a cell scaffold has a size and shape corresponding to a graft chamber or graft chamber insert provided that the cell scaffold fits into the graft chamber or graft chamber insert under press fit conditions.

In addition, a person having ordinary skill in the art will appreciate that other acceptable variations in size and shape can be determined and that such variations are intended fall within the scope of the present invention.

Three-Dimensional Models

Figure 4A:
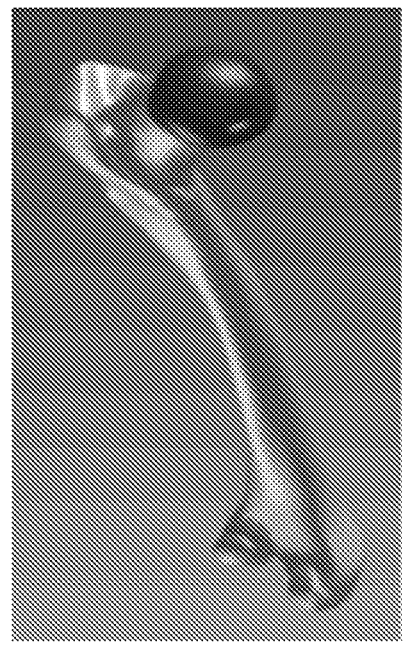
FIGS. 4A-4B.
Figure 4B:
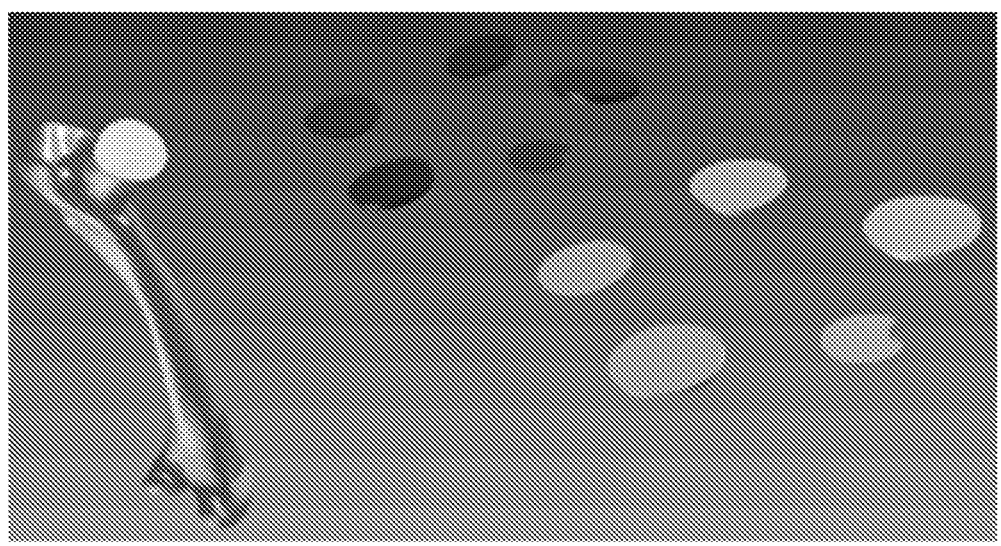

In some embodiments of the present invention, three-dimensional models of a particular tissue or tissue portion may be generated and/or used, for example to serve as a template for the production of a tissue graft or tissue graft segment, and/or to serve as a template for the production of a scaffold material to be used in the manufacture of such a tissue graft or tissue graft segment, and/or to serve as a template for the production of a bioreactor, bioreactor chamber, or bioreactor chamber insert that could be used in the production of a tissue graft, tissue graft segment, or hybrid tissue-implant grafts. See, for example, FIGS. 4A-4B and FIG. 6. In some embodiments such three-dimensional models are digital models, such as digital models that represent the three-dimensional shape and size of a tissue portion of interest. For example, three-dimensional models or images, such as digital models or images of structures inside the body, can be generated by any suitable method known in the art, including, for example, computed tomography (CT) (including small-scale CT such as micro-CT) which uses x-rays to make detailed pictures of internal body structures and organs. In some embodiments medical imaging technologies can be used to generate a digital model of a desired tissue portion, for example a tissue portion comprising a defect, such as a skeletal defect, and that digital model can then be used to facilitate the manufacture of a tissue graft, and/or one or more tissue graft segments—for example by enabling the production of a scaffold material and/or bioreactor that is custom designed to be used in the manufacture of the desired tissue graft or tissue graft segment. A model of a tissue portion will preferably be anatomically accurate, having dimensions, geometry, size and shape that correspond to the physical tissue portion and/or the desired tissue graft. In some embodiments, the portion of tissue may comprise a defect, such as a traumatic or pathological defect. In some embodiments, such defect can be repaired a using a tissue graft prepared according to the present invention. Digital models of tissue portions can be created using any suitable computer-aided design (CAD) software, such as Autocad™, Solidworks™, ProE™, or Creo™. In some embodiments a digital model of a tissue portion can be edited and segmented/partitioned into two or more smaller sub-parts or segments (which may be referred to as "model segments" or "model portions"), for example representing tissue graft segments that can be prepared according to the present invention, and/or representing scaffold materials or bioreactor chambers that can be used for the preparation of such tissue graft segments. The thickness of the model segments can be selected such that a tissue graft segment having the same thickness could be effectively perfused in a bioreactor. Thus, in some embodiments, a model segment, and/or a corresponding tissue graft segment (e.g. a bone graft segment), has a thickness or a maximum thickness of about one centimeter or less. In some embodiments, the model segment and/or the corresponding tissue graft segment has a thickness or a maximum thickness of about 0.3 millimeters to about 10 millimeters, or about 0.3 millimeters to about 5 millimeters, or about 0.3 millimeters to about 1 millimeter. In some embodiments, the model segment and/or the corresponding tissue graft segment has a thickness of about 0.3, about 0.5, about 1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10 millimeters.

The models, such as digital models, described herein can be used to design and manufacture customized bioreactors and/or customized scaffolds to grow physical tissue graft segments having a size and shape corresponding to the complementary models. In the case of digital models, the models or model segments can be created using, or converted into, any suitable file formats, for example, IGES or SLT formats, and can be created using, or imported into, any suitable computer-aided manufacturing (CAM) software, for example, SprutCAM™. Manufacture of custom bioreactors and scaffolds is further described herein.

Digital models of tissues, and segments thereof, provided by the invention can be generated, edited and otherwise manipulated as described herein. In addition, a person having ordinary skill in the art will appreciate that any other suitable methods may be used to generate, edit or otherwise manipulate digital models of tissues or segments thereof as described herein.

Cell Scaffolds

In some embodiments, the present invention provides scaffolds suitable for use in the preparation of tissue grafts and/or tissue graft segments, for example as described herein. Scaffolds can be made of any suitable material having appropriate pore sizes, porosity and/or mechanical properties for the intended use. Such suitable materials will typically be non-toxic, biocompatible and/or biodegradable, and capable of infiltration by cells of the desired tissue graft type, for example bone-forming cells in the case of bone tissue grafts. Non-limiting examples of such materials include de-cellularized tissue (such as de-cellularized bone), materials that comprise or one or more extracellular matrix ("ECM") components such as collagen, laminin, and/or fibrin, and natural or synthetic polymers or composites (such as ceramic/polymer composite materials). In some embodiments the scaffold material may be capable of being absorbed by cells (e.g., resorbable materials), while in other embodiments non-resorbable scaffold materials may be used. In some embodiments, the scaffold may comprise, consist of, or consist essentially of, any of the above-listed materials, or any combination thereof.

Figure 5A:
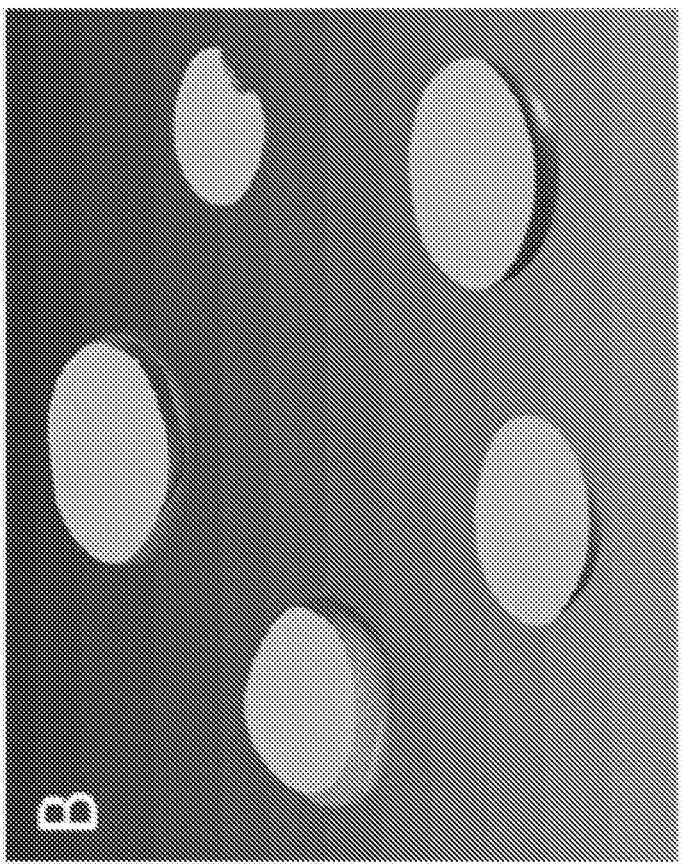
FIGS. 5A-5B. Perspective view of exemplary cell culture scaffolds provided by the invention.
Figure 5B:
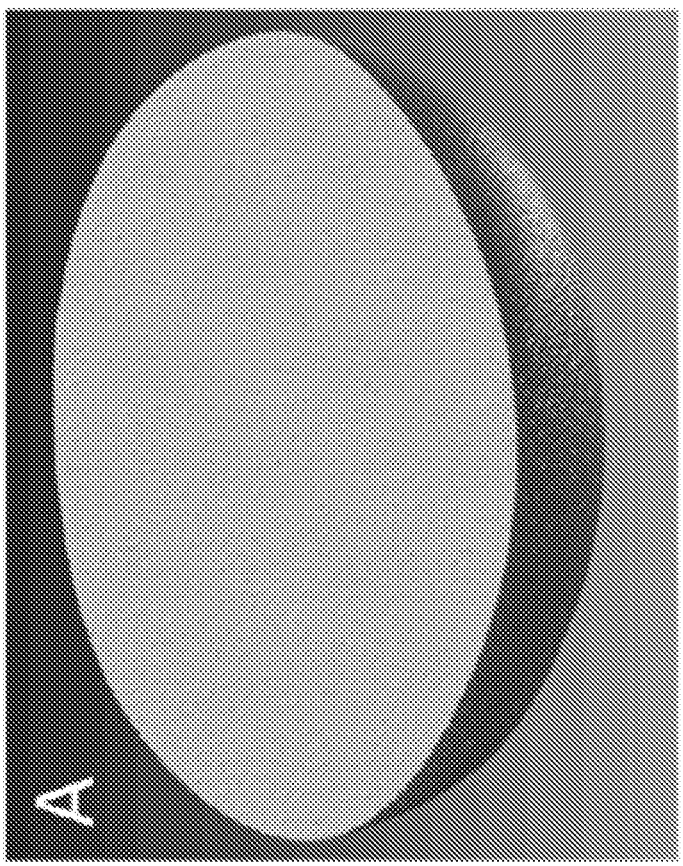

In some embodiments, the dimensions and geometry of a scaffold correspond to that of a three-dimensional model, such as a digital model, of a tissue portion or tissue segment, and/or correspond to that of the desired tissue graft of tissue graft segment, as described above. In some embodiments the dimensions and geometry of a scaffold can be designed or selected based on such a model in order to facilitate culturing of cells, e.g., tissue-forming cells or other cells as described herein, on the scaffold within a bioreactor, as further described below, for example in order to produce a tissue graft or tissue graft segment having a size and shape corresponding to a model or model segment. In some embodiments, scaffolds may be designed to fit into a bioreactor chamber of suitable size and shape to allow direct perfusion of the scaffold and the cells therein (e.g., during the process of producing the tissue graft and/or tissue graft segment) under press-fit conditions. FIGS. 5A-5B show illustrative scaffolds as provided herein.

In some embodiments, the scaffold is generated or customized using computer-assisted manufacturing. For example, a tissue model segment file can be used with, CAM software to drive the fabrication of geometrically defined scaffolds using any suitable method known in the art, or a combination thereof, for example, computer-controlled milling methods, rapid prototyping methods, laser cutting methods, three-dimensional printing, and/or casting technologies. In some embodiments, manufacturing of the scaffold comprises using rapid prototyping, a milling machine, casting technologies, laser cutting, and/or three-dimensional printing, or any combination thereof. In some embodiments, manufacturing of the scaffold comprises using computer-numerical-control, such as when the manufacturing comprises laser cutting or using a milling machine. For example, digital models, such as those generated using CAD software as described above, can be processed to generate the appropriate codes (such as "G-Codes") to drive a computer-numerical-control (CNC) milling machine (for example, Tormach™, Bridgeport™) and to select appropriate machining tool bits and program machining paths to cut the scaffold material into the desired shapes and sizes (e.g., corresponding to that of a digital models of a tissue segment).

While scaffolds provided by the invention can be designed and manufactured as described herein, a person having ordinary skill in the art will appreciate that a variety of other methods of designing and manufacturing may be used to generate scaffolds according to the present invention.

Bioreactors

In some embodiments, the present invention provides culture vessels, such as bioreactors, suitable for use in the preparation of tissue grafts and tissue graft segments, for example as described herein. In some embodiments, the bioreactors are perfusion bioreactors, for example, direct perfusion bioreactors. Perfusion bioreactors for tissue engineering applications are culture systems that typically comprise several elements, including, but not limited to one or more chambers where cell/scaffold constructs are placed (referred to herein as a "graft chamber"), a culture medium reservoir, a tubing circuit, and a pump enabling mass transport of nutrients and oxygen. Perfusion bioreactors may be broadly classified into indirect or direct systems, depending on whether the culture medium is perfused around or through the cell/scaffold constructs. For a review of bioreactors, see, Sladkova et al. (*Processes* 2(2) 494-525 (2014)), the contents of which is hereby incorporated by reference).

With direct perfusion bioreactors, cell/scaffold constructs are placed in a suitable graft chamber in a press-fit fashion so that the culture medium is forced to pass through the cell/scaffold construct, rather than around the cell/scaffold construct. Direct perfusion bioreactors have been used to engineer bone substitutes using a combination of different human osteocompetent cells and biomaterial scaffolds. Furthermore, in the case of bone engineering, studies demonstrate that direct perfusion of different combinations of cell/scaffold constructs can support cell survival and proliferation, and formation of mature bone-like tissue in vitro (for review, see, Sladkova, supra).

In some embodiments, the present invention provides certain novel bioreactors, such as novel direct perfusion bioreactors, and methods for designing and making such novel bioreactors. For example, in some embodiments models, such as digital models, of tissue portions or segments thereof, as described above, can be used to design and manufacture bioreactors that can accommodate one or more cell/scaffold constructs in a press-fit fashion under direct perfusion conditions. In some such embodiments CAD files of a tissue segment can be used to fabricate bioreactors, or graft chambers of bioreactors, or inserts for graft chambers of bioreactors, such that the bioreactor graft chamber has a size and geometry that is custom-designed to correspond to that of the tissue graft or tissue graft segment to be produced therein, and such that the scaffold and/or tissue graft/graft segment fits snugly within the bioreactor graft chamber in a press-fit configuration. Such bioreactors, or the graft chambers or graft chamber inserts thereof, can be made out of any suitable material. Materials that are suitable for the manufacture of bioreactors, or inserts thereof, are known in the art and any such materials can be used. For example, in some embodiments bioreactors, or chambers or inserts thereof, may be made of an inert metal, such as stainless steel, or made of biocompatible plastic, or any other suitable material known in the art.

In some embodiments, a bioreactor, bioreactor graft chamber, or bioreactor graft chamber insert is generated or customized using computer-assisted manufacturing. For example, in some such embodiments tissue segment files can be imported into CAM software to drive the fabrication or customization of bioreactors, bioreactor graft chambers, or bioreactor graft chamber inserts capable of accommodating geometrically defined scaffolds and/or tissue grafts or tissue graft segments using any suitable method known in the art, or a combination thereof. In some such embodiments, manufacturing or customization of the bioreactor may comprise using a rapid prototyping method, using a milling machine, using casting technologies, using laser cutting, and/or using three-dimensional printing. In some embodiments, manufacturing or customization of a bioreactor, bioreactor graft chamber, or bioreactor graft chamber insert may comprise using computer-numerical-control methods, such as when the manufacturing or customization process involves laser cutting or using a milling machine. For example, in some embodiments digital models generated using CAD software, for example, as described above may be processed to generate the appropriate G-Codes to drive a computer-numerical-control (CNC) milling machine (for example, Tormach™, Bridgeport™) and/or to select appropriate machining tool bits and/or program machining paths to cut the bioreactor, bioreactor graft chamber, or bioreactor graft chamber insert material into the desired shapes (e.g., complementary to the digital models of the tissue segments). In addition, digital drawing and simulation software can be used to optimize the design of bioreactors, bioreactor graft chambers, or bioreactor graft chamber inserts, and to drive the controlled manufacturing or customization thereof. In some embodiments bioreactors, bioreactor graft chambers, or bioreactor graft chamber inserts, can be designed based on digital models of tissues or tissue segments to facilitate culturing of cells, e.g., tissue-forming cells or other cells as described herein or known in the art, on scaffolds in order to produce a tissue graft or tissue graft segment having a size and shape corresponding to the complementary digital model of the tissue or tissue segment.

In some embodiments a bioreactor according to the present invention may comprise one or more elements, wherein these elements are secured together, for example by screws or latches or any other securing system, to form one or more internal chambers, including but not limited to a graft chamber. In one embodiment, the bioreactor comprises a reservoir for culture medium, a fluid inlet port and one or more fluid channels.

In some embodiments, the bioreactors of the invention may comprise a graft chamber that is designed or customized in order to accommodate a scaffold, tissue graft, or tissue graft segment of the desired shape and size. In one embodiment this may be achieved by designing or customizing the bioreactor itself such that it has a graft chamber having the desired shape and size. In another embodiment this may be achieved using a graft chamber insert that, when placed inside a bioreactor, produces a graft chamber that has the desired shape and size. In one embodiment, a bioreactor according to the present invention comprises a graft chamber of a size sufficient to accommodate a scaffold, tissue graft, or tissue graft segment having a thickness of about 0.3 millimeters to about 10 millimeters. In some embodiments, the scaffold and/or tissue graft segment may be positioned in the graft chamber using a graft chamber insert, which may also be referred to herein as a "frame." As described above, frames or graft chamber inserts may be used to customize the size and shape of a graft chamber and position a scaffold and/or tissue graft segment in the graft chamber, as desired, for example in order to allow culture the tissue graft segment under direct perfusion, press-fit conditions to maximize the flow of fluid through the scaffold and/or tissue graft segment, and minimize the flow of fluid around the scaffold and/or tissue graft segment. In some embodiments the graft chamber may have a generic shape or size, but one or more frames or graft chamber inserts may be used to customize the size and shape (e.g., the internal size and shape) of the graft chamber, as desired, to accommodate the scaffold and/or tissue graft segment. Frames or graft chamber inserts may be made of any suitable material. For example, in some embodiments the frame and/or graft chamber insert may comprise, consist essentially of, or consist of, a biocompatible, non-toxic, moldable plastic, such as silicone or a silicone-like material. In some such embodiments, the frame and/or graft chamber insert may comprise polydimethylsiloxane (PDMS). Frames or graft chamber inserts may be designed and manufactured by any suitable method, including, but not limited to, the methods described herein.

Figure 6:
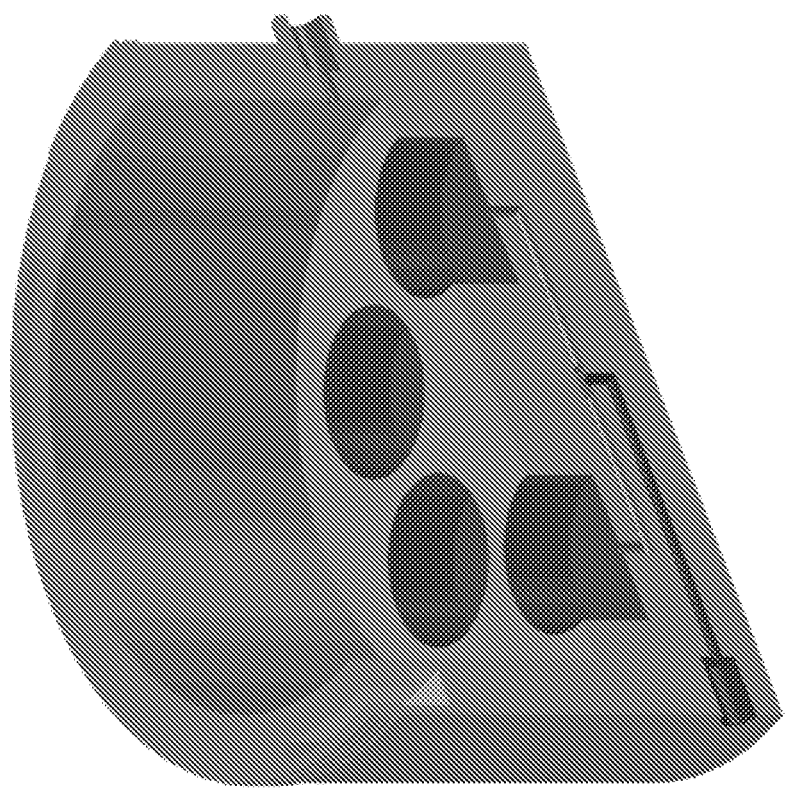
FIG. 6. Cross-sectional view of an exemplary multi-chamber bioreactor provided by the invention.
Figure 7A:
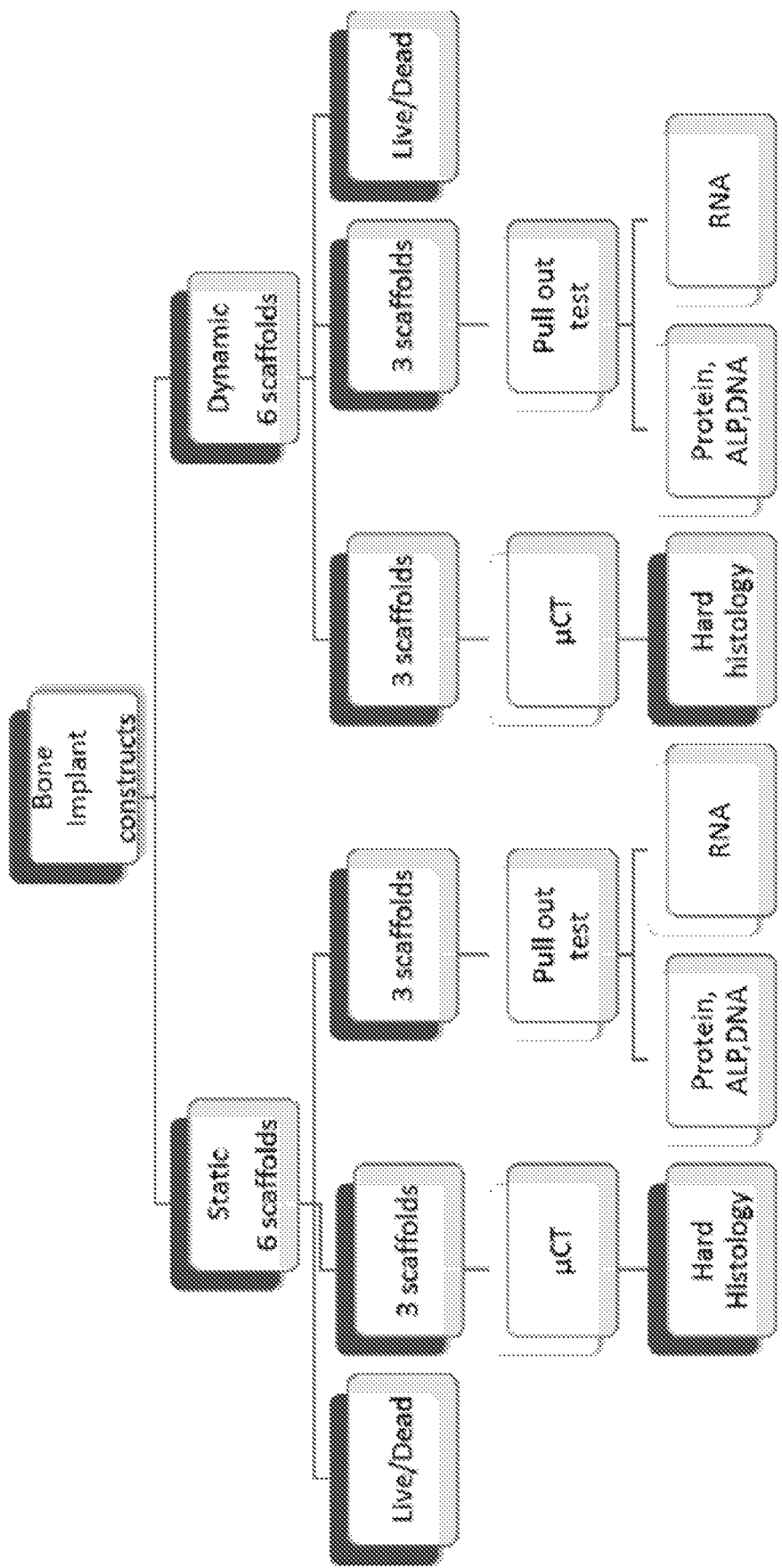
FIGS. 7A-7D.
Figure 7B:
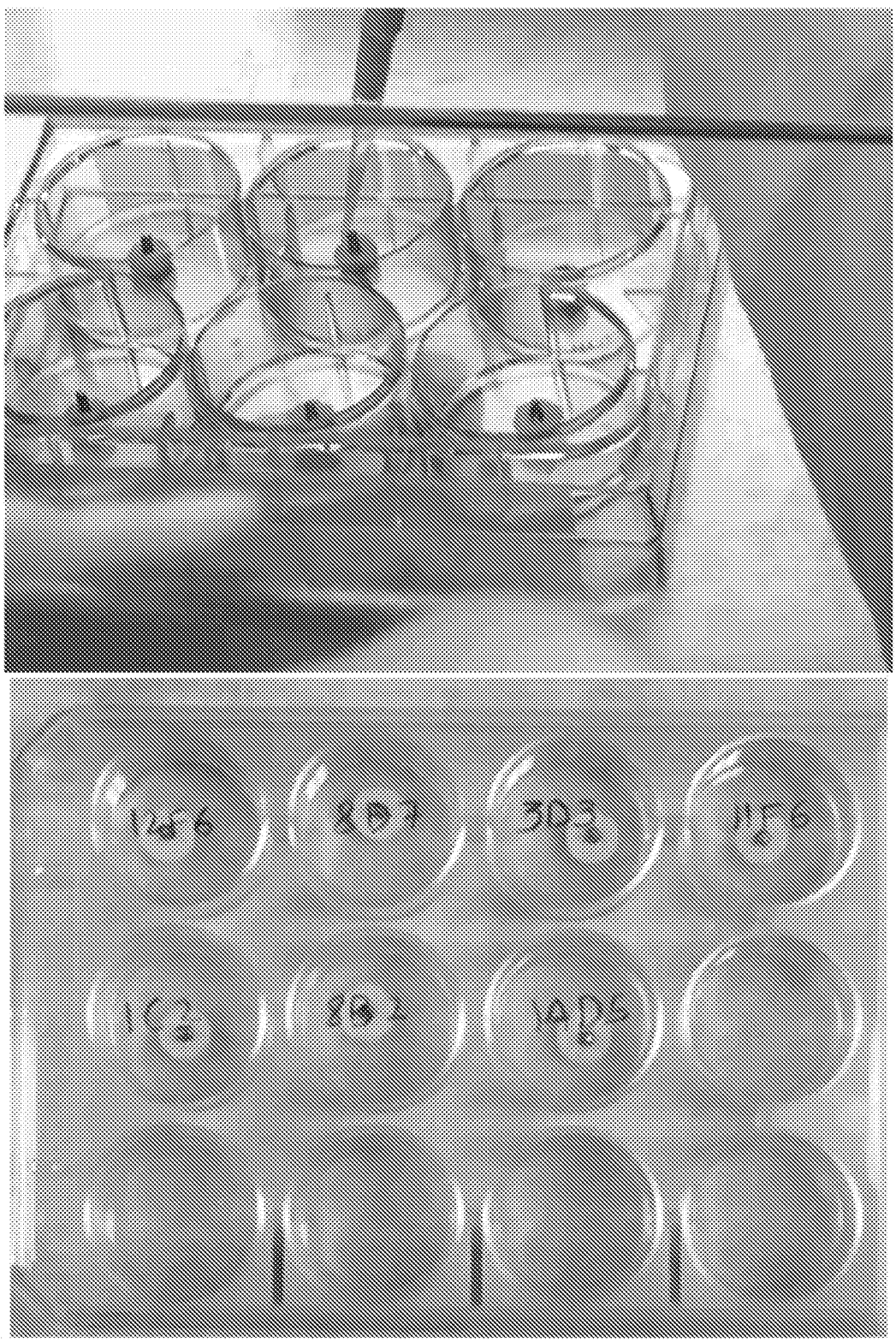
Figure 7C:
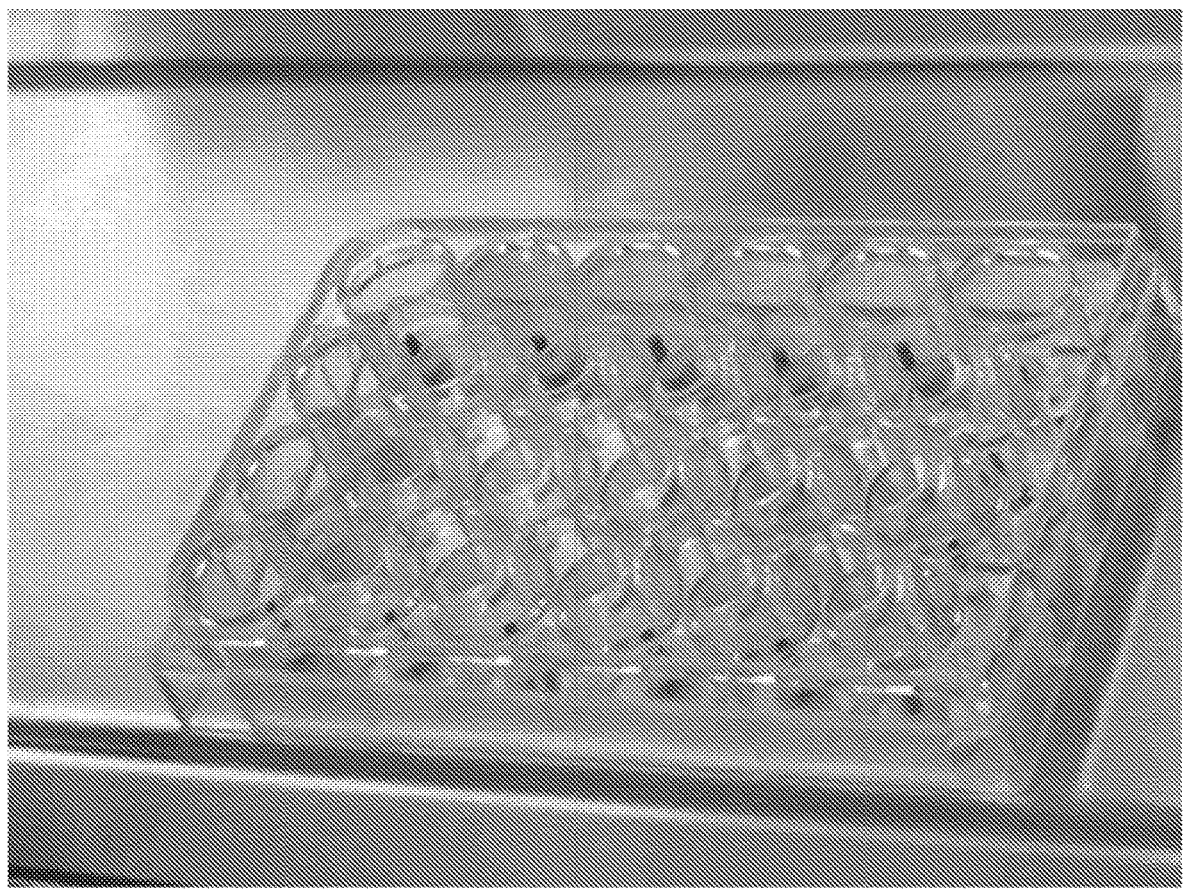
Figure 7D:
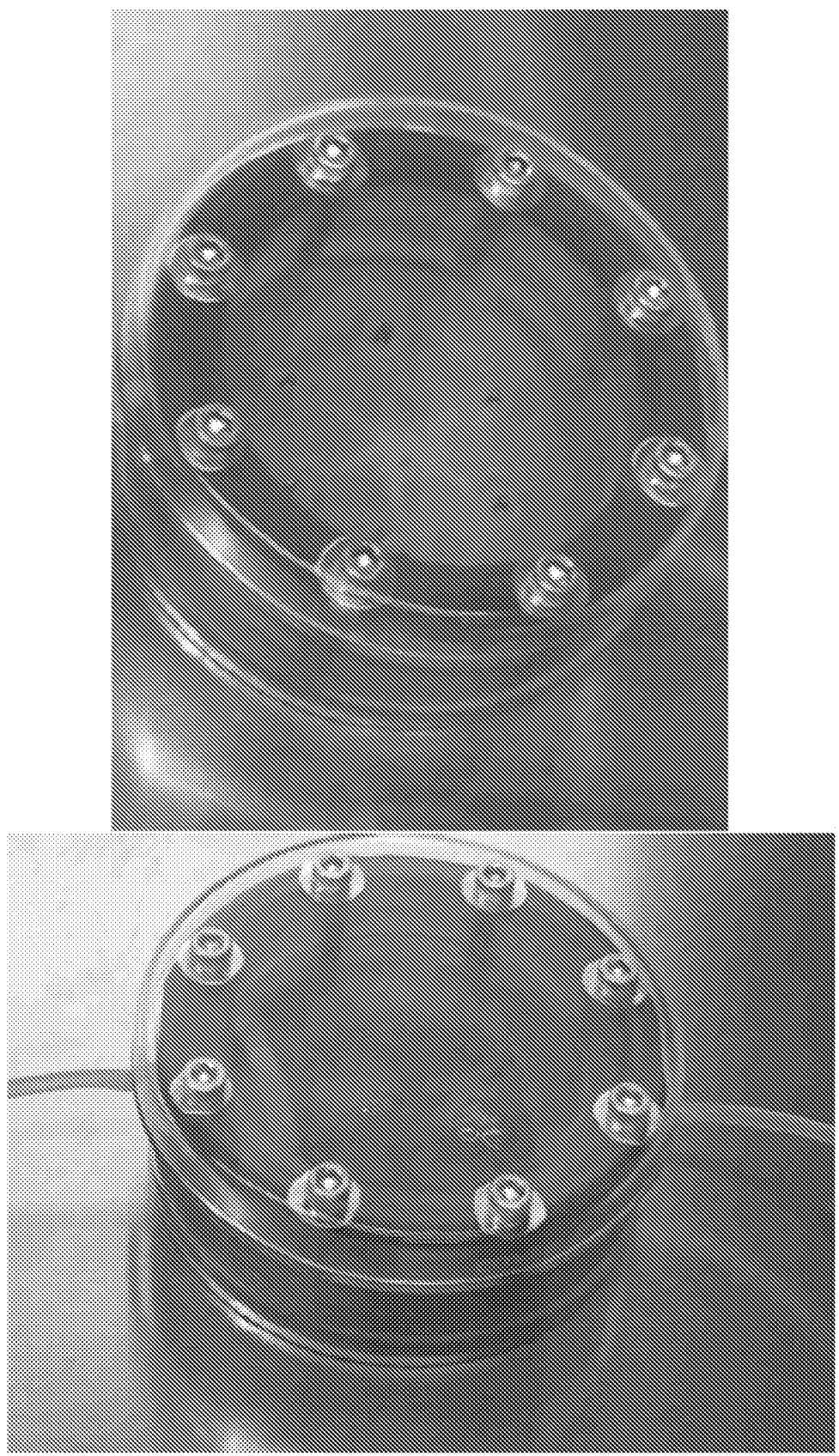

In some embodiments, the bioreactors of the present invention may comprise more than one graft chamber to facilitate the collective culture of multiple tissue graft segments (see, FIG. 6). For example, in one embodiment a bioreactor according to the present invention may be configured to accommodate the culture of one, two, three, four, five or more tissue graft segments, as desired.

In some embodiments bioreactors, bioreactor graft chambers, and graft chamber frames or inserts, as provided by the present invention, can be designed and manufactured as described herein, for example using computer-aided design (CAD) and computer-aided manufacture (CAM) methods. However, a person having ordinary skill in the art will appreciate that a variety of other methods of may be used to generate and customize bioreactors, bioreactor graft chambers, and bioreactor graft chamber frames or inserts according to the present invention.

Cells

Any suitable or desired type of cell or cells may be used in the preparation of tissue grafts or tissue graft segments in accordance with the present invention, as described herein. Typically the selected cell(s) will be capable of forming the desired tissue graft (for example, for a vascularized bone graft, mesenchymal progenitor cells and endothelial progenitor cells or any other cell types suitable for or capable of forming bone and blood vessels, as further described herein), or any cell(s) capable of differentiating into the desired tissue-forming cell(s) (for example, a pluripotent cell). Non-limiting examples of cells that may be used include pluripotent cells, stem cells, embryonic stem cells, induced pluripotent stem cells, progenitor cells, tissue-forming cells, or differentiated cells.

The cells used may be obtained from any suitable source. In some embodiments, the cells may be human cells. In some embodiments, the cells may be mammalian cells, including, but not limited to, cells from a non-human primate, sheep, or rodent (such as a rat or mouse). For example, cells may be obtained from tissue banks, cell banks or human subjects. In some embodiments, the cells are autologous cells, for example, cells obtained from the subject into which the prepared tissue graft will be subsequently transplanted, or the cells may be derived from such autologous cells. In some embodiments, the cells may be obtained from a "matched" donor, or the cells may be derived from cells obtained from a "matched" donor. For cell and tissue transplants, donor and recipient cells can be matched by methods well known in the art. For example, human leukocyte antigen (HLA) typing is widely used to match a tissue or cell donor with a recipient to reduce the risk of transplant rejection. HLA is a protein marker found on most cells in the body, and is used by the immune system to detect cells that belong in the body and cells that do not. HLA matching increases the likelihood of a successful transplant because the recipient is less likely to identify the transplant as foreign. Thus, in some embodiments of the present invention, the cells used are HLA-matched cells or cells derived from HLA-matched cells, for example, cells obtained from a donor subject that has been HLA-matched to the recipient subject who will receive the tissue graft. In some embodiments the cells used may be cells that have been modified to avoid recognition by the recipient's immune system (e.g. universal cells). In some such embodiments the cells are genetically-modified universal cells. For example, in some embodiments the universal cells may be MHC universal cells, such as major histocompatibility complex (MHC) class I-silenced cells (see, i.e., Figueiredo et al., *Biomed Res Int* (2013)). Human MHC proteins are referred to as HLA because they were first discovered in leukocytes. Universal cells have the potential to be used in any recipient, thus circumventing the need for matched cells.

In some embodiments, the cells used in making the tissue grafts of the present invention are, or include, pluripotent stem cells, such as induced pluripotent stem cells (iPSCs). In some such embodiments, the pluripotent stem cells may be generated from cells obtained from the subject (i.e. autologous cells) that will receive the tissue graft. In other such embodiments, the pluripotent stem cells may be generated from cells obtained from a different individual—i.e. not the subject that will receive the tissue graft (i.e. allogeneic cells). In some such embodiments, the pluripotent stem cells may be generated from cells obtained from a different individual—i.e. not the subject that will receive the tissue graft—but where that different individual is a "matched" donor—for example as described above. In some embodiments, the cells used are differentiated cells, such as bone cells. In some embodiments, the differentiated cells are derived from pluripotent stem cells, such as induced pluripotent stem cells. In some embodiments, the differentiated cells are derived by trans-differentiation of differentiated somatic cells, or by trans-differentiation of pluripotent cells (such as pluripotent stem cells or induced pluripotent stem cells), for example induced pluripotent stem cells generated from somatic cells.

A pluripotent stem cell is a cell that can (a) self-renew and (b) differentiate to produce cells of all three germ layers (i.e. ectoderm, mesoderm, and endoderm). The term "induced pluripotent stem cell" encompasses pluripotent stem cells, that, like embryonic stem cells (ESC), can be cultured over a long period of time while maintaining the ability to differentiate into cells of all three germ layers, but that, unlike ES cells (which are derived from the inner cell mass of blastocysts), are derived from somatic cells, that is, cells that had a narrower, more defined potential and that in the absence of experimental manipulation could not give rise to cells of all three germ layers. iPSCs generally have an hESC-like morphology, growing as flat colonies with large nucleo-cytoplasmic ratios, defined borders and prominent nuclei. In addition, iPSCs generally express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, iPSCs, like other pluripotent stem cells, are generally capable of forming teratomas. In addition, they are generally capable of forming or contributing to ectoderm, mesoderm, or endoderm tissues in a living organism.

Illustrative iPSCs include cells into which the genes Oct-4, Sox-2, c-Myc, and Klf have been transduced, as described by Takahashi and Yamanaka (*Cell* 126(4):663-76 (2006), the contents of which is hereby incorporated by reference in its entirety). Other exemplary iPSCs are cells into which OCT4, SOX2, NANOG, and LIN28 have been transduced (Yu et al., *Science* 318:1917-1920 (2007), the contents of which is hereby incorporated by reference in its entirety). One of skill in the art would know that various different cocktails of reprogramming factors can be used to produce iPSCs, such as factors selected from the group consisting of OCT4, SOX2, KLF4, MYC, Nanog, and Lin28. The methods described herein for producing iPSCs are illustrative only and are not intended to be limiting. Rather any suitable methods or cocktails of reprogramming factors known in the art can be used. In embodiments where reprogramming factors are used, such factors can be delivered using any suitable means known in the art. For example, in some embodiments any suitable vector, such as a Sendai virus vector, may be used. In some embodiments reprogramming factors may be delivered using modified RNA methods and systems. A variety of different methods and systems are known in the art for delivery of reprogramming factors and any such method or system can be used.

Any culture medium suitable for culture of cells, such as pluripotent stem cells, may be used in accordance with the present invention, and several such media are known in the art. For example, a culture medium for culture of pluripotent stem cells may comprise Knockout™ DMEM, 20% Knockout™ Serum Replacement, nonessential amino acids, 2.5% FBS, Glutamax, beta-mercaptoethanol, 10 ng/microliter bFGF, and antibiotic. The employed medium may also be a variation of this medium, for example without the 2.5% FBS, or with a higher or lower % of knockout serum replacement, or without antibiotic. The employed medium may also be any other suitable medium that supports the growth of human pluripotent stem cells in undifferentiated conditions, such as mTeSR™ (available from STEMCELL Technologies), or Nutristem™ (available from Stemgent™), or ES medium, or any other suitable medium known in the art. Other exemplary methods for generating/obtaining pluripotent stem cells from a population of cells obtained from a subject are provided in the Examples of the present application.

In some embodiments, pluripotent stem cells are differentiated into a desired cell type, for example, a bone-forming cell or a blood vessel-forming cell, or any other desired cell type. Differentiated cells provided by the invention can be derived by various methods known in the art using, for example, adult stem cells, embryonic stem cells (ESCs), epiblast stem cells (EpiSCs), and/or induced pluripotent stem cells (iPSCs; somatic cells that have been reprogrammed to a pluripotent state). Methods are known in the art for directed differentiation or spontaneous differentiation of pluripotent stem cells, for example by use of various differentiation factors. Differentiation of pluripotent stem cells may be monitored by a variety of methods known in the art. Changes in a parameter between a stem cell and a differentiation factor-treated cell may indicate that the treated cell has differentiated. Microscopy may be used to directly monitor morphology of the cells during differentiation.

In each of the embodiments of the invention, any suitable or desired types of cells can be used to produce the tissue grafts and tissue graft segments described herein, including, but not limited to, pluripotent stem cells or progenitor cells or differentiated cells. In some embodiments, the pluripotent stem cells may be induced pluripotent stem cells. In embodiments where induced pluripotent stem cells are used, such cells may be derived from differentiated somatic cells obtained from a subject, for example by contacting such differentiated somatic cells with one or more reprogramming factors. In some embodiments, pluripotent cells may have been induced toward a desired lineage, for example, mesenchymal lineage or endothelial lineage. In some embodiments, the differentiated cells can be any suitable type of differentiated cells. In some embodiments, the differentiated cells may be derived from pluripotent stem cells (such as induced pluripotent stem cells), for example by contacting such pluripotent cells with one or more differentiation factors. In some embodiments, the differentiated cells may be derived by trans-differentiation of another differentiated cell type, for example by contacting the cells with one or more reprogramming factors. In the various embodiments of the present invention involving differentiated cells, such differentiated cells may be any desired differentiated cell type, including, but not limited to, bone cells and blood vessel cells.

Cell/Scaffold Constructs

Any suitable or desired type of cell, such as the cell types described herein, can be applied to or seeded onto a scaffold to prepare tissue graft or tissue graft segment according to the present invention.

In some embodiments, cells may be in a differentiated state prior to being applied to a scaffold. For example, in some embodiments differentiated cells may be obtained and used directly. Similarly, in some embodiments non-differentiated cells may be cultured according to any suitable method known in the art, such as in a culture dish or multi-well plate or in suspension, for a suitable period or length of time, for example, until desired levels of cell growth or differentiation or other parameters are achieved, then the differentiated cells may be transferred to the scaffold and subsequently the cell/scaffold construct is inserted into a bioreactor to facilitate development of a tissue graft or tissue graft segment. In some embodiments, non-differentiated cells (for example, stem cells (such as iPSCs) or progenitor cells) may be applied to the scaffold. In such embodiments, the non-differentiated cells may undergo differentiation while being cultured on the scaffold. Cells can be applied using static and dynamic methods (e.g. using bioreactor systems), or combination thereof. Dynamic systems facilitate uniform seeding when engineering large tissue-implant grafts.

In some embodiments, two or more different cell populations may be seeded onto a scaffold to prepare a cell/scaffold construct. For example, in some embodiments both bone-forming cells and blood vessel-forming cells may be seeded onto a scaffold and co-cultured for the preparation of a vascularized bone graft (see, FIG. 7). In some embodiments, the two or more populations of cells are co-cultured on the scaffold for a suitable period of time, for example, until desired levels of growth or differentiation or other parameters are achieved, before the cell/scaffold construct is inserted into the bioreactor. Populations of cells may comprise, consist essentially of, or consist of, any desired type of cell in any stage of growth or differentiation, and any combinations thereof. For example, in some embodiments, each cell population may comprise cells capable of forming a different tissue, for example for the preparation of a vascularized bone graft, a first population containing cells capable of forming bone, such as mesenchymal progenitor cells, and a second population containing cells capable of forming blood vessels, such as endothelial progenitor cells. In some embodiments, each population of cells may comprise cells capable of forming the same tissue (e.g., bone) but each population of cells may be at different stages of differentiation (e.g., mesenchymal stem cells and bone marrow stromal cells). Populations of cells to be co-cultured may be applied to a scaffold at the same time or at different times, as desired. Where two or more populations of cells are applied at different times, the sequence or order of co-culture (e.g., which population is applied to the scaffold first, which population is applied to the scaffold second, etc.) may be selected as desired, for example depending on the cell types being used, the state or growth or differentiation of the populations of cells, or any other parameters, as desired.

Where two or more populations of cells are to be applied to the scaffold, they can be applied at any suitable cell ratio, as desired. For example, in some embodiments two different populations of cells may be seeded at a ratio of about 1:1, or any ratio from about 2:8 to about 8:2. In some embodiments, the cell populations may be seeded at a ratio of about 2:8, about 3:7, about 4:6, about 5:5, about 6:4, about 7:3, or about 8:2.

A cell/scaffold construct may be transferred to a bioreactor at any suitable point, for example, immediately after seeding with cells, following a certain period of cell culture following seeding, after the seeded cells have reached a desired state of differentiation or any other desired state, as desired. In some embodiments the cell/scaffold construct is inserted into a bioreactor and cultured under press fit conditions to allow formation of a tissue graft or tissue graft segment. Tissue/graft development can be assessed using any suitable qualitative or quantitative methods known in the art, including but not limited to histological and immunohistochemical examination, biochemical assays, high-resolution characterization techniques (e.g., SEM, FIB-TEM, Tof-SIMS), imaging procedures (e.g., CT or microCT) and mechanical testing (e.g., Young's modulus, tensile and compressive strength).

A person having ordinary skill in the art will recognize that countless variations and combinations of cells and culture methods will fall within the scope of the present invention. For example, cell culture methods, including cell seeding methods and ratios, concentration of differentiation factors and sequence of co-culture, will typically be determined according to the desired cell type being used or the tissue graft being prepared.

Tissue Grafts, and Assembly and Use Thereof

In some embodiments, the present invention provides tissue grafts, such as bone grafts, that are assembled from multiple tissue graft segments. The present invention also provides methods of making such tissue grafts. Such methods may be referred to as segmental additive tissue engineering (SATE) methods. In the case of bone grafts in particular, such methods may be referred to as segmental additive bone engineering (SABE) methods. At any suitable point, for example when a tissue graft segment having the desired properties has been produced, tissue graft segments can be removed from the bioreactor in which they are produced and multiple tissue graft segments can be assembled together to form a tissue graft having the desired size and shape, for example a size and shape corresponding to the tissue portion to be replaced.

Assembled tissue graft segments can be secured or attached together by any suitable means or method capable of maintaining the intended assembly of the segments. For example typically, such securing means or methods will be non-toxic, biocompatible and/or resorbable (e.g., capable of being absorbed by the body), for example, where the assembled tissue graft will be transplanted into a subject. For example, in some embodiments, the tissue graft segments may be secured to each other using an adhesive, stitches or sutures, staples, plates, pins and holes, screws, bolts, or the like, as desired. In some embodiments, the means used to secure the tissue segments together are biocompatible or resorbable or both.

In some embodiments, where an adhesive is used to secure the graft segments to each other, the adhesive may be a biocompatible glue, for example, a biocompatible polymer glue such as NovoSorb™ (PolyNovo Biomaterials, Melbourne) or any gel, liquid, rubber-like substance, or other biocompatible adhesive material capable of securing together two or more tissue graft segments. For example, in the case of bone grafts, exemplary bone glues that can be used to secure bone graft segments to each other include, but are not limited to, polymer-based or polymeric bone glues such as polyurethane-based and polymethylmethacrylate-based bone glues. In some embodiments, the adhesive may be a tape, for example, a surgical tape. In some embodiments, tissue graft segments may be secured to each other using one or more plates, pins, screws, bolts, staples, stitches, sutures, or the like, for example made of plastic, metal (for example, titanium) or any other suitable material. In some embodiments such pins, screws, bolts, staples, stitches, sutures, or the like may be manufactured using 3D printing or any other suitable method known in the art.

Figure 8:
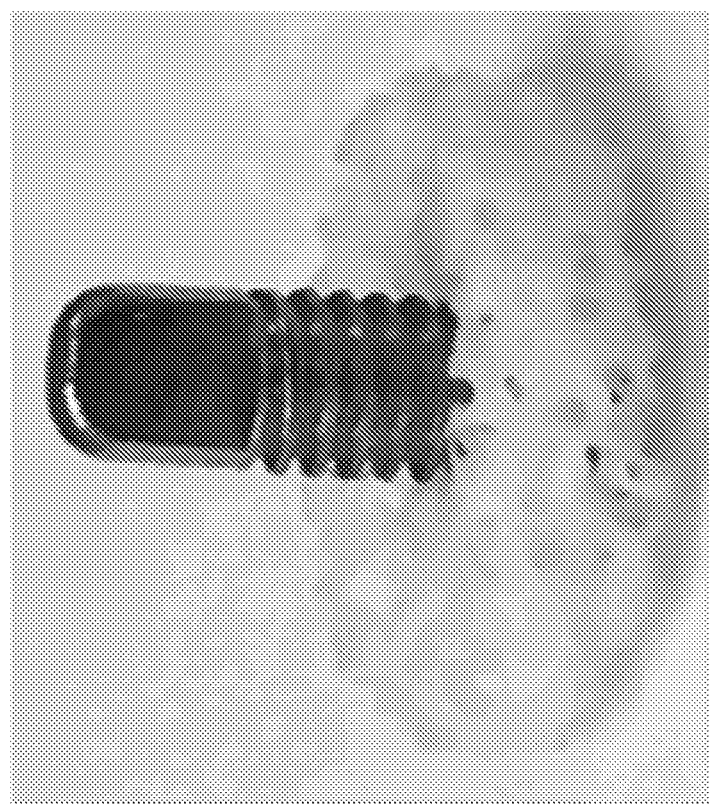
FIG. 8. The left panel shows a titanium screw mini-implant. The right panel shows the titanium mini-implant inserted into a demineralized cow bone scaffold.
Figure 8:
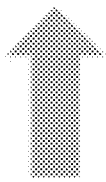
Figure 8:
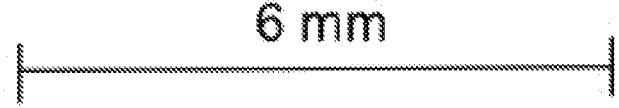
Figure 8:
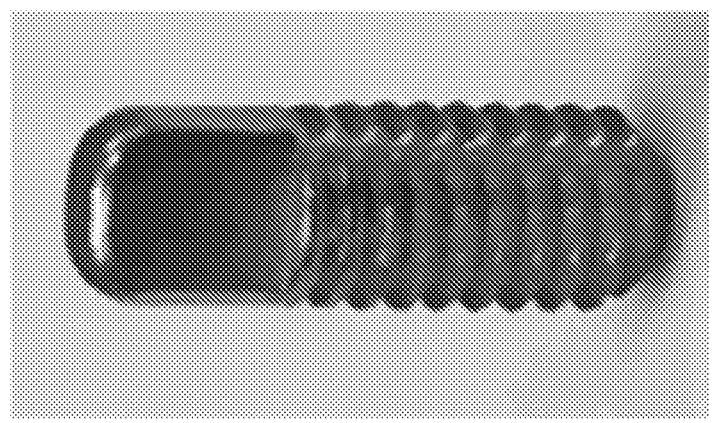
Figure 9:
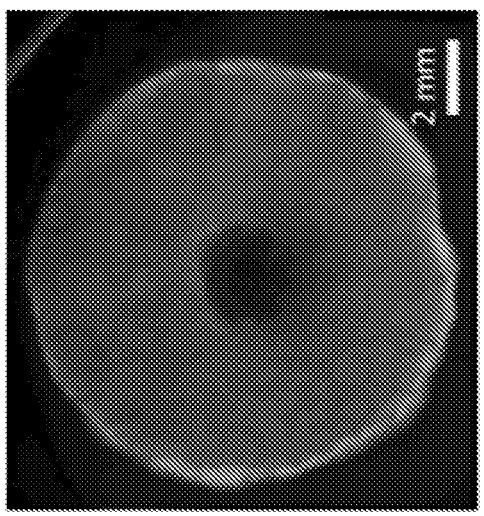
FIG. 9. Bone cells grow on the demineralized cow bone scaffold and migrate onto a titanium implant. Live healthy bone cells are stained green, dead cells are stained red. The upper panel shows live bone cells growing on the implant. The lower panels show the migration of bone cells toward the implant (the edge of the implant is depicted by a dotted line) and onto the implant.
Figure 9:
Figure 10:
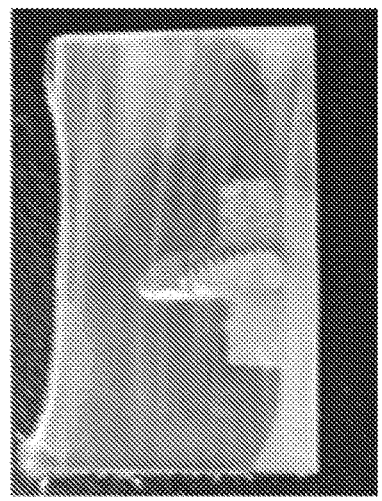
FIG. 10. To perform histology on the implant/bone graft constructs, the constructs were embedded in resin and sectioned according to a modified Erben 1779 protocol (Reinhold G. Erben, *J Histochem Cytochem* 45: 307 (1997)).
Figure 10:
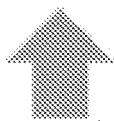
Figure 10:
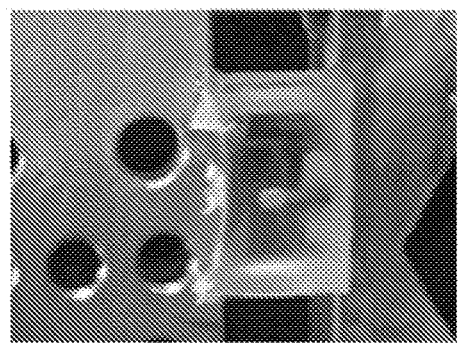
Figure 10:
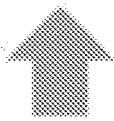
Figure 10:
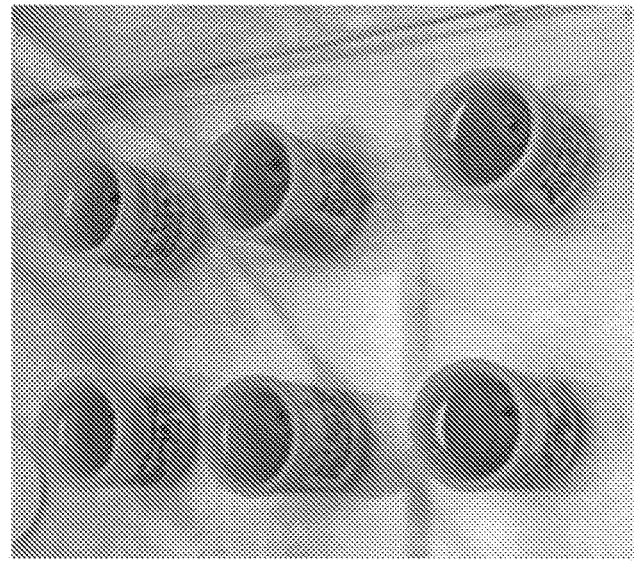
Figure 11:
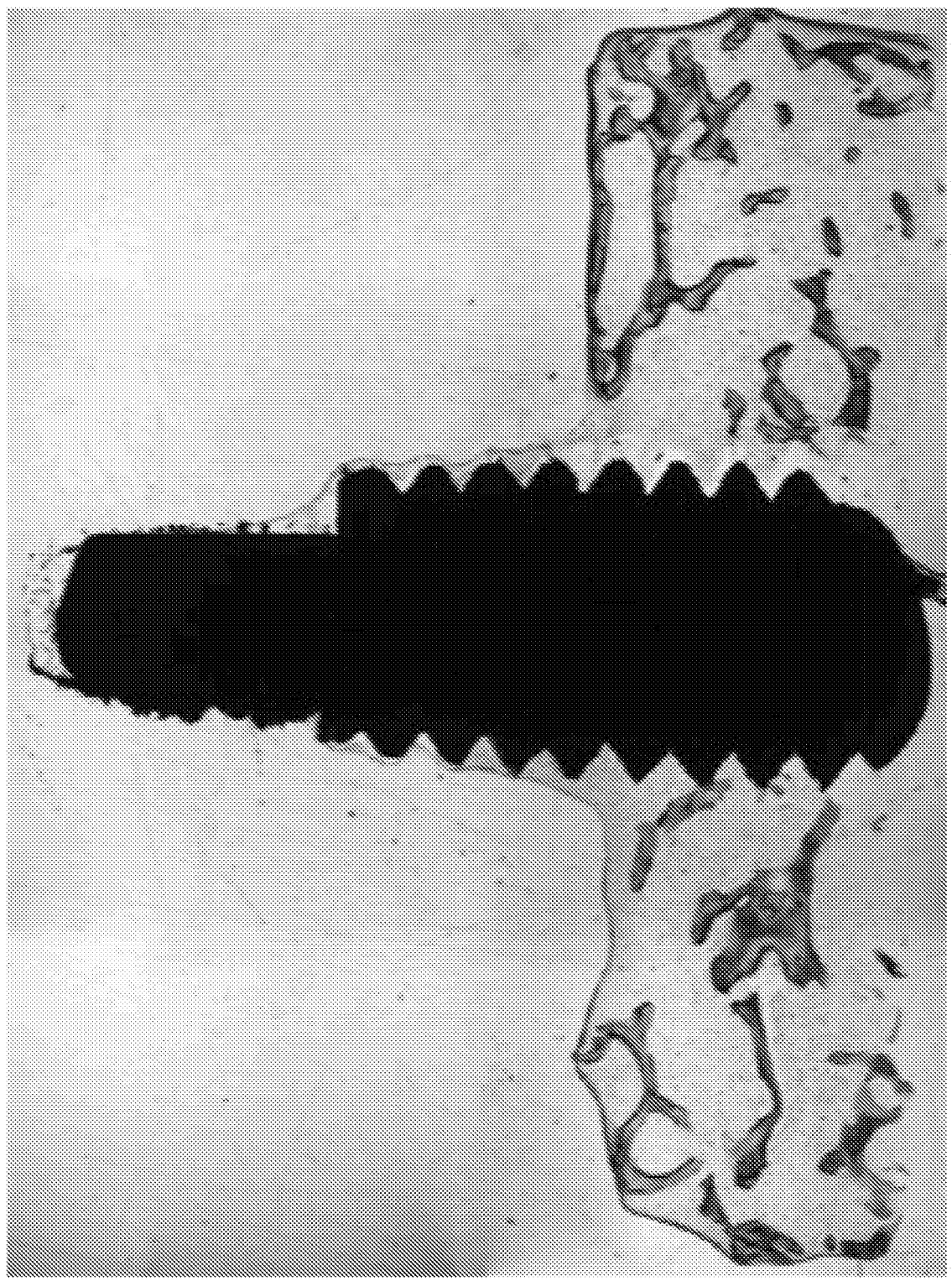
FIG. 11. Histological staining of a cross-section of the implant/bone graft construct shows bone cells growing on the surface of the titanium implant. Stevenel's blue was used to stain the nuclei of cells in the newly formed bone tissue (blue). The demineralized cow bone scaffold stains brown.
Figure 12:
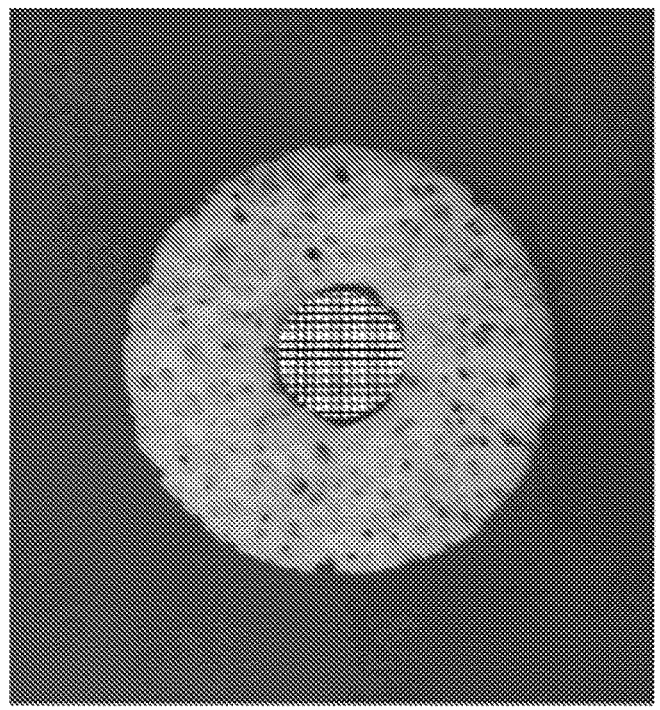
FIG. 12. The left panel shows a top view of a scaffold with an opening in the center to accommodate insertion of an implant material. The right panel shows a top view of a hypothetical material or implant or device inserted into the opening of the scaffold.
Figure 12:
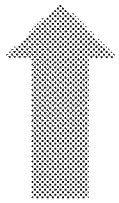
Figure 12:
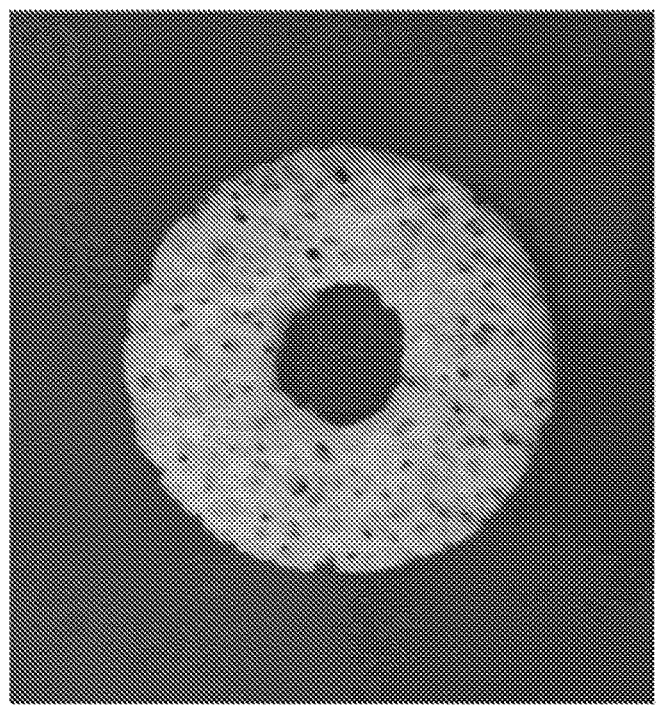

In some embodiments, various different means and/or methods to secure the assembled tissue graft segments together may be used in combination, for example, to reinforce the connection between the assembled tissue graft segments and/or to attach or anchor or secure the tissue graft to the host tissues, such as where a tissue graft is transplanted into a subject (see, FIG. 8). For example, in some embodiments engineered bone graft segments as described herein can be assembled together using both a biocompatible bone glue and metallic or resorbable pins.

Following assembly and securing together of the tissue graft segments, the resulting tissue graft can be transplanted into a subject, where it may also be anchored to the subject's tissues (such as surrounding bone in the case of a bone graft). In some embodiments, the methods and compositions provided by the present invention may be used to engineer tissue grafts for clinical applications, including therapeutic and/or cosmetic applications. Non-limiting examples of such applications include repair or replacement of a tissue defect or damage or tissue loss, tissue reconstruction or rebuilding, tissue reinforcement (e.g., to prevent or delay progression of tissue damage or loss of tissue) or to assist in the implantation of surgical devices (e.g., bone grafts can be used to help bone heal around surgically implanted devices such as joint replacements, plates or screws). In some embodiments, a subject has a tissue defect or tissue loss caused by injury, disease, birth defect, trauma or infection.

In some embodiments, the invention provides a method of repairing or replacing a tissue defect, tissue loss or tissue damage, comprising transplanting a tissue graft according to the present invention into a subject so as to repair or replace the tissue defect, tissue loss or tissue damage in the subject. In some embodiments, the tissue graft will have a size and shape corresponding to that of the tissue being repaired or replaced. Tissue grafts according to the present invention can be prepared using the segmental additive tissue engineering or SATE methods provided herein. Thus, in some embodiments, a tissue graft according to the present invention may comprise, consist of, or consist essentially of, two or more tissue graft segments, wherein the tissue graft segments have a thickness of less than about 1 centimeter, or a thickness of about 0.3 millimeters to about 10 millimeters. In some embodiments, such a tissue graft may be an autograft (also referred to as an autogenous, autogeneic or autogenic graft), such as where the subject's own cells or tissue (e.g., autologous cells or tissue) are used to generate the tissue graft. In some embodiments, the tissue graft is an allograft (e.g., the tissue graft is generated from cells or tissues obtained from a donor subject of the same species as the recipient subject), such as where the donor and recipient subjects have been matched, for example, by HLA-matching. In some embodiments, the tissue graft is a xenograft (e.g., the tissue graft is generated from cells or tissues obtained from a donor subject of a different species as the recipient subject). For example, a tissue graft comprising human tissue may be transplanted into a non-human mammal, such as a sheep, for example for performing certain in vivo testing, etc.

A tissue graft prepared according to the present invention and transplanted into a subject can be anchored or attached or secured to existing structures (e.g., tissue) in the subject by any suitable method capable of securing tissue, such as described above. In some embodiments, the transplanted tissue graft is secured by an adhesive, stitches or sutures, staples, plates, pins or the like. In some embodiments, the means to secure the tissue graft inside the subject's body will be biocompatible or resorbable or both.

Figure 20A:
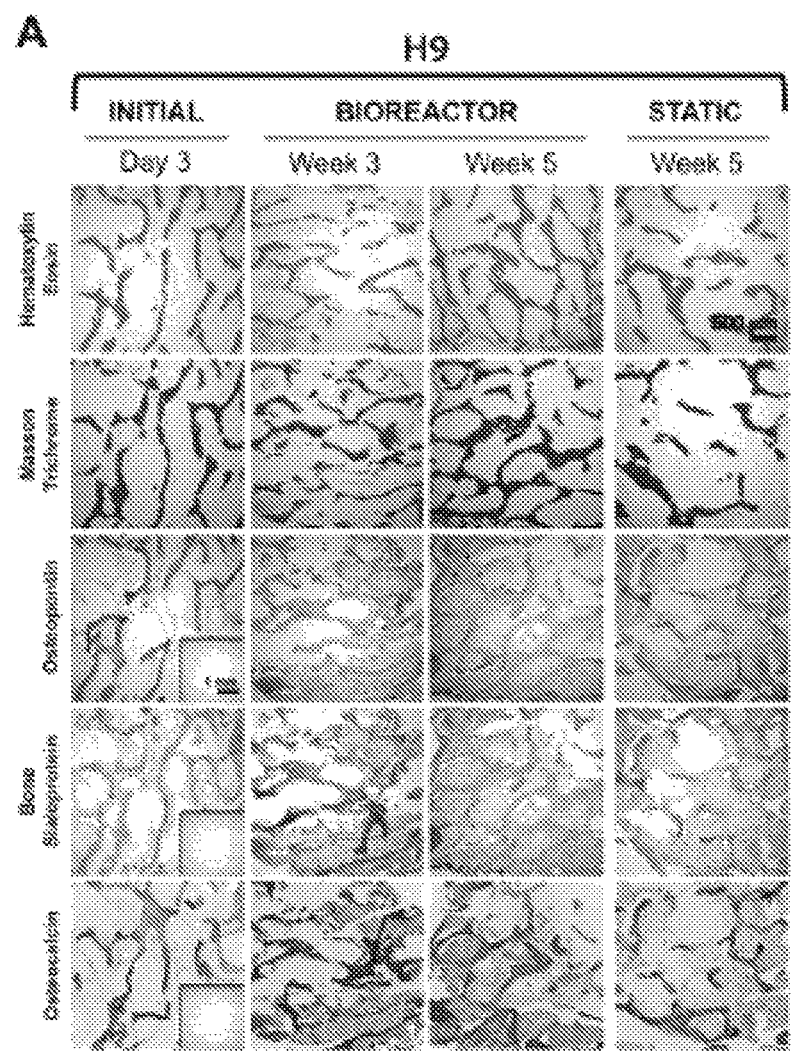
FIGS. 20A-20C are a series of images showing the effect of bioreactor on bone tissue development. Low-magnification histological micrographs. Constructs of (A) H9-, (B) 1013A-, and (C) BC1-derived progenitors cultured on decellularized cow scaffolds for 5 weeks in perfusion bioreactors showed uniform tissue formation and denser tissue matrix compared with constructs from static cultures (TOP). Higher deposition of bone matrix proteins in perfusion bioreactor was confirmed by positive staining of collagen (Masson trichrome, blue; Upper Middle), osteopontin (brown; Middle), bone sialoprotein (brown; Lower Middle), and osteocalcin (brown; Bottom). Only minimal staining was observed in statically cultured constructs at weeks 3 and 5. (Inserts) Negative staining control.
Figure 20B:
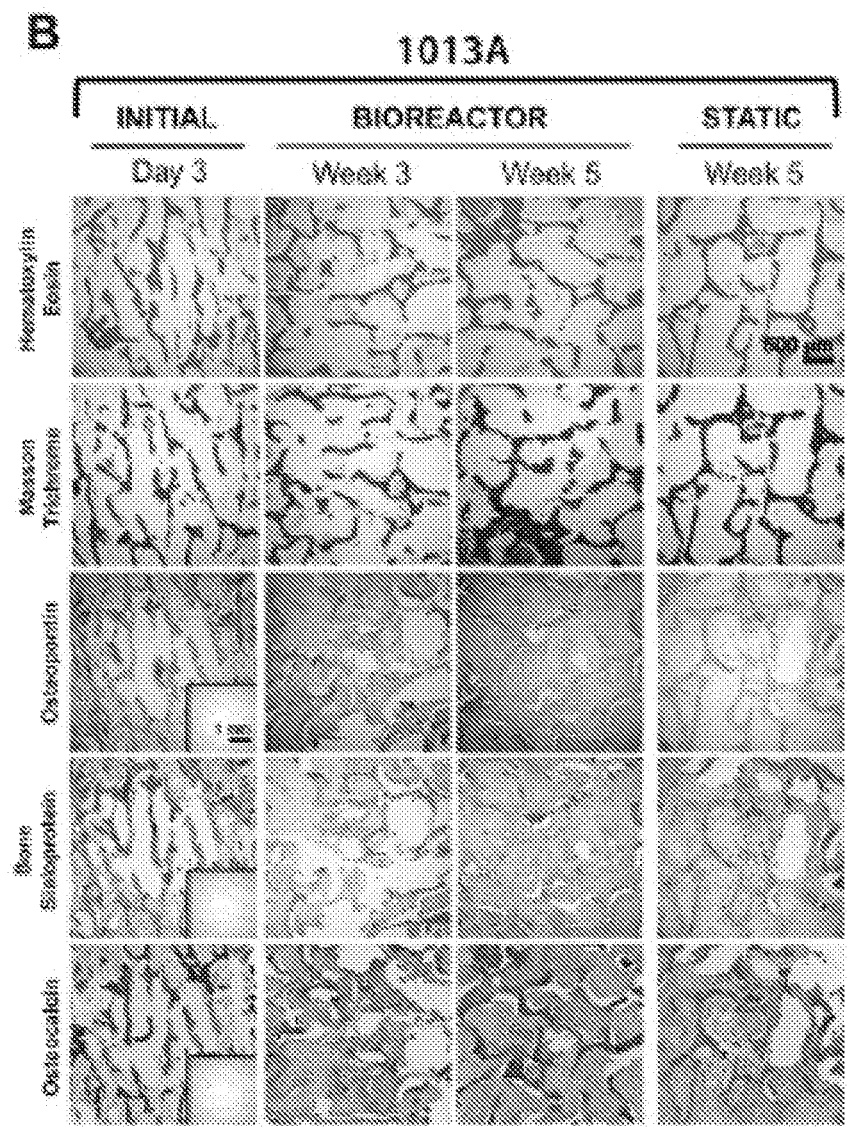
Figure 20C:
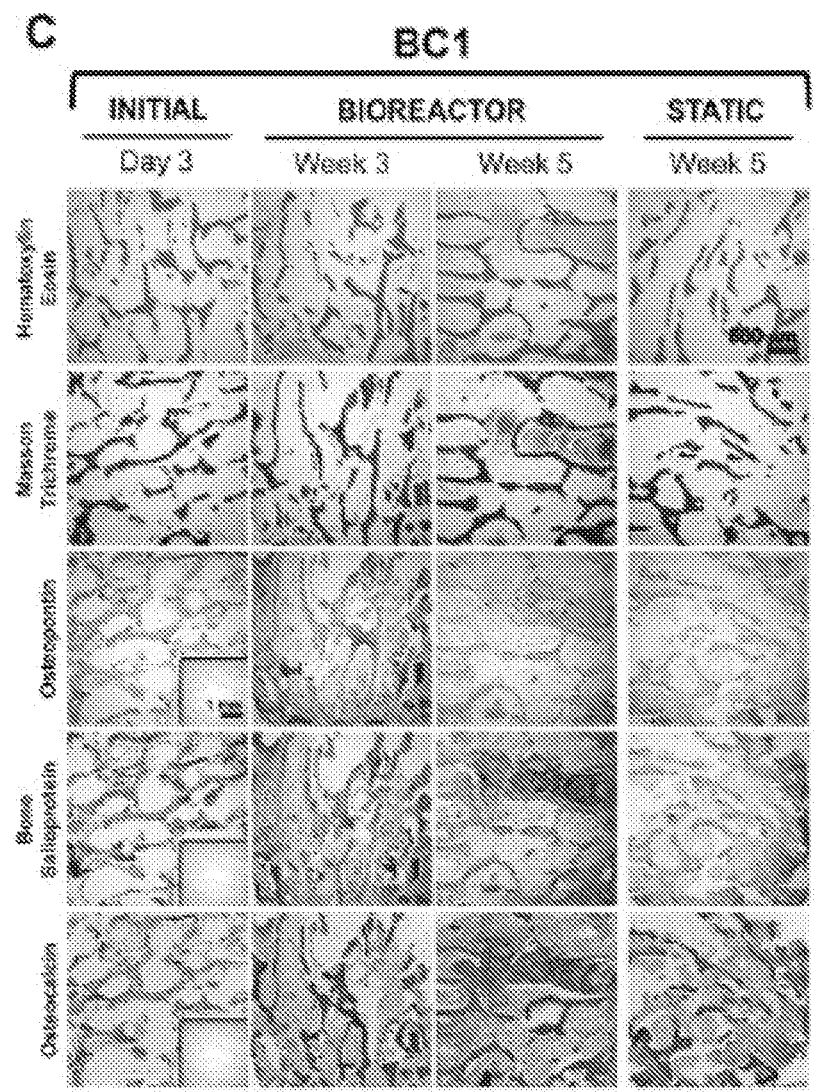

The bone matrix composition of the bone-engineering grafts generated via the present invention (i.e., Example 3) is shown in FIGS. 20A-20C. The porous bone architecture is filled with a thick cell-synthesized matrix including collagen 1, osteopontin, osteocalcin and bone salioprotein. The matrix also contains other structural and biologically active proteins, in a concentration and ratio that is different from the native tissue thereby distinguishing the two bone materials.

Figure 21:
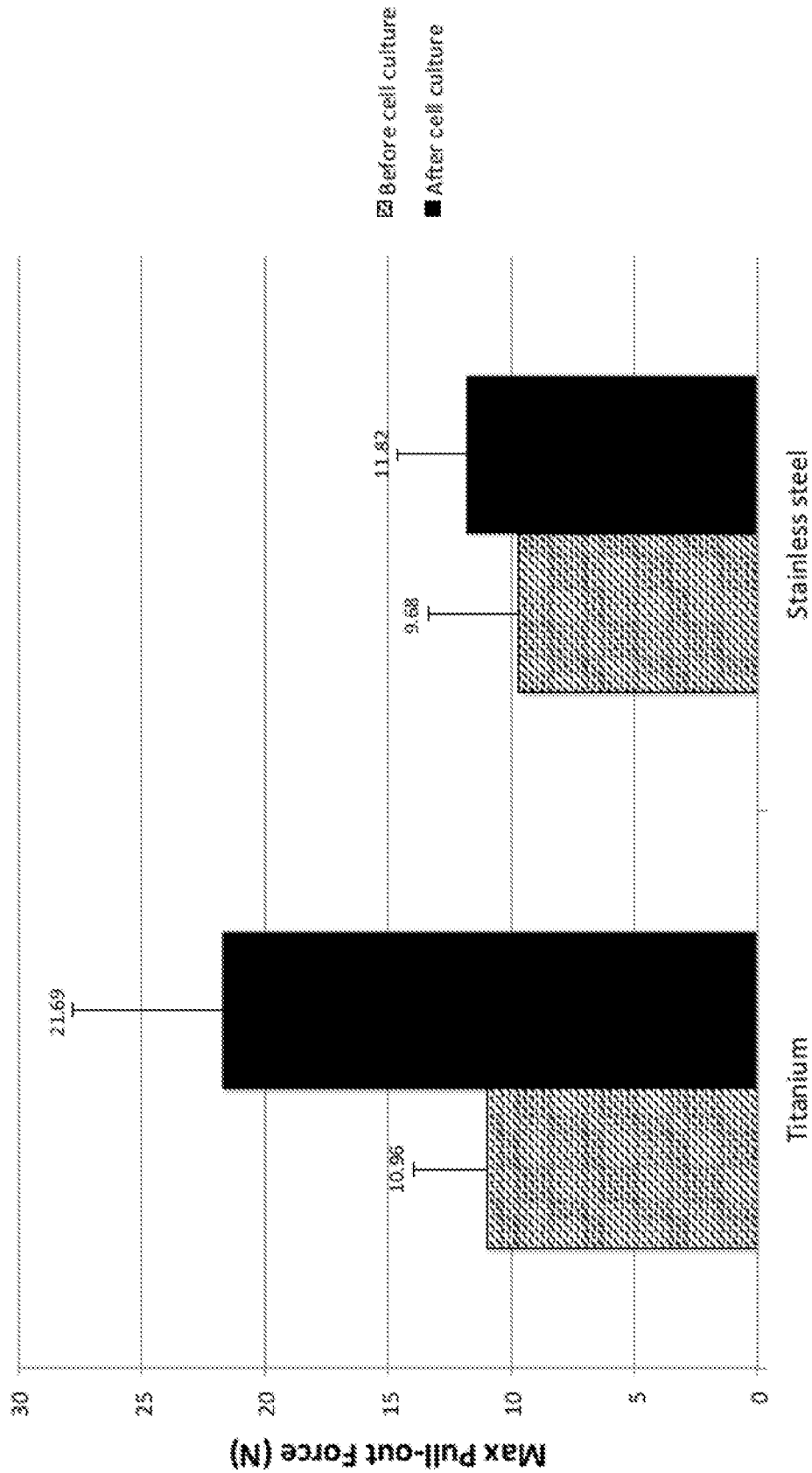
FIG. 21 is a graph of a comparison between pullout force required to extract implants (titanium and stainless steel) after insertion into decellularized bone scaffold, seeding with bone progenitor cells, and culturing for 7 weeks as discussed in Example 3.

As shown in FIG. 21, there is an increase in strength due to cell activity and tissue formation at the implant site (i.e., attachment of the seeded cells to the implant material). This increase is significant and higher for titanium implants as shown from in-vivo experiments.

In embodiments, attachment strength of the implant to the bone material is increased after culture of seeded cells by 15, 10, 15, 20, 25, 30, 35, 40, 45, 50, 55, 60, 65, 70, 75, 80, 90, 100, 110, 120, 130, 140, 150, 160, 170, 180, 190, 200, 150, 300, 350, 400, 500, 600, 700, 800, 900, 1000 percent or greater.

Bone

Bone is a two-phase porous composite material with a complex hierarchical structure, in which the HA crystals are arranged in parallel layers within the collagen framework surrounded by ground substance.

The ECM of mature bone tissue is composed of 30-40 percent of organic matrix and 60-70 percent (dry weight) of mineral substance. The organic material mainly consists of type I collagen fibrils (85-90 percent) embedded in the ground substance containing proteoglycan aggregates (mainly biglycan and decorin) and glycoproteins. Glycoproteins represent the largest proportion of non-collagenous proteins (NCPs) and include Sialoprotein, Alkaline Phosphatase, Osteonectin, Osteocalcin and Osteopontin. The sequence of most NCPs includes high density of amino acids with high affinity for calcium, such as aspartic and glutamic acid residues. The inorganic material consists mainly of calcium phosphate crystals in the form of hydroxyapatite (HA) with molecular formula $Ca10(PO4)6(OH)2$, although bicarbonate, citrate, magnesium, potassium and sodium are also found.

Engineered Bone of the Present Invention

The ECM of tissue-engineered bone includes Sialoprotein, Alkaline Phosphatase, Osteonectin, Osteocalcin and Osteopontin. The mineral content of the newly formed bone is lower than native bone, and it is made of calcium phosphate minerals arranged in different forms, which include amorphous and crystalline calcium phosphate with different calcium to phosphorus ratios (dicalcium phosphate, tricalcium phosphate, and the like).

Porosity and Mechanical Properties

The porosity of trabecular bone varies in different anatomical locations and ranges from 30-95% (mostly in the range 75-95%). It also can differ from species to species at same anatomical locations.

In embodiments, after seeding the cells on decellularized bone scaffolds, the cells produce new tissue that starts filling the voids until substantially complete occlusion of the scaffold pores. The porosity of the scaffold therefore decreases over time of culture, for example, 10-20% after 3 days, 30-50% after 3 weeks, 75-90% after 5 weeks and up to or equal to 100% at complete maturation. The speed of decrease in porosity also depends on cell proliferation potential, use of growth factors, culture under dynamic conditions, initial seeding density and so forth.

Bone has very strong mechanical properties, with a compressive strength of several MPa. The newly formed bone instead is very week in compressive strength, and the exact value depends on length of cultures and mineralization potential of employed cells under given culture conditions.

Model Systems and Screening Methods

In some embodiments, the present invention provides model systems for studying various biological processes or biological properties, and screening methods for testing the effects of various agents on such biological processes and/or biological properties. In some embodiments such biological processes may include, for example, those associated with a disease or disorder or those associated with a surgical procedure. In some such embodiments such biological processes or properties may include, for example, those associated with formation of biological tissues (including, but not limited to production of tissue grafts), such as those relating to the differentiation or culture of various cell types, or those relating to the ability of various cell types to form functional tissues, or those relating to the biological, mechanical, immunological, or other biological properties of a tissue (or tissue graft), and the like. For example, the methods, compositions (e.g. tissue grafts), and devices (e.g. bioreactors), described herein can be used in, or in conjunction with, model systems, such as models for studying particular diseases or disorders, or model systems for studying the ability of cells, such as stem cells (e.g. iPSCs) to form functional tissues. Similarly, the methods, compositions (e.g. tissue grafts), and devices (e.g. bioreactors), described herein can be used in, or in conjunction with, screening systems, for studying the effects of one or more agents (such as drugs, or any other agents) on the ability of cells to form functional tissues, such as tissue grafts. For example, in one embodiment, the present invention provides a method of identifying an agent that may be useful for treating, preventing or delaying the progression of a disease or disorder, or for supporting the formation of a particular tissue (for example from stem cells), or for producing a tissue graft having one or more desired properties, comprising (a) contacting a tissue graft according to the present invention with a test agent in vitro or in vivo, and (b) assessing the effects of the test agent on the tissue graft and/or on one of the biological processes or properties described above. Some such methods may also comprise contacting a tissue graft with a control agent, and comparing the effects of the test agent to that of the control agent. In some such embodiments, the tissue graft comprises cells derived from progenitor cells, pluripotent cells (such as induced pluripotent stem cells), autologous cells (such as the subject's own cells), or any cell capable of (i) forming the desired tissue(s), or (ii) differentiating into a cell that is capable of forming the desired tissue(s). In some embodiments, the tissue graft can be a vascularized tissue graft, wherein the tissue graft comprises endothelial cells or other blood vessel cells, such as those derived from progenitor cells (such as endothelial progenitor cells), pluripotent cells (such as induced pluripotent stem cells), autologous cells (such as the subject's own cells), or any cell capable of (i) forming endothelium and/or blood vessels, or (ii) differentiating into a cell that is capable of forming endothelium and/or blood vessels. In some embodiments, the tissue grafts are generated using induced pluripotent stem cells. In some embodiments, the tissue grafts comprise cells derived from a subject having a particular disease or disorder. In some embodiments, a vascularized tissue graft according to the invention can be used in, or in conjunction with, model systems, such as model systems for studying vascular diseases or disorders. In some embodiments, a vascularized tissue graft according to the invention may be used in, or in conjunction with, screening systems for studying the effects of one or more agents (such as drugs, or any other agents) on the vascularized tissue.

Test agents to be screened encompass numerous chemical classes, though typically they are chemical compounds, such as an organic molecule, and often oligonucleotides or small organic compounds (i.e., small molecules) having a molecular weight of more than 100 Daltons and less than about 2,500 Daltons. Test agents comprise functional groups necessary for structural interaction with proteins, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one aspect, an agent for use in with the present invention is a polynucleotide, such as an antisense oligonucleotide or RNA molecule. In various aspects, the agent may be a polynucleotide, such as an antisense oligonucleotide or RNA molecule, such as microRNA, dsRNA, siRNA, stRNA, and shRNA.

In some embodiments, the present invention provides a model system comprising a tissue graft according to the present invention. For example, in some embodiments the present invention provides a model system comprising a tissue graft according to the present invention that has been implanted into a subject that is a non-human mammal. In one such embodiment, the non-human mammal is a sheep. In some embodiments, the present invention provides a model system comprising a tissue graft or tissue segment according to the present invention that is used to determine whether an implant material is suitable for implantation into a subject (see, Example 2). For example, in some such embodiments, an implant material may be screened or tested for desired properties, such as biocompatibility, mechanical properties, or toxicity. In some such embodiments, an implant material may be a synthetic material or a natural material or a mix of synthetic and natural materials. Model systems provided by the invention can be used for various purposes such as but not limited to screening or testing materials for implantation (see, Example 2) and to study diseases under defined tissue-specific conditions, including for understanding underlying mechanisms, defining therapeutic targets and conducting compound screening, and the like.

Furthermore, those of ordinary skill in the art will appreciate that the methods, compositions (e.g. tissue grafts), and devices (e.g. bioreactors), described herein can be used in, or in conjunction with, a variety of different model systems and screening methods.

Subjects

In some embodiments the cells used in producing the tissue grafts of the present invention may be obtained from or derived from any subject, as needed or as desired. In some embodiments the methods (e.g. treatment methods) and compositions (e.g., tissue grafts) provided by the present invention may be used in any subject, as needed or as desired (for example, to repair a pathological or traumatic tissue defect, or for cosmetic or reconstructive purposes). In some embodiments, the subject is a human. In some embodiments, the subject is a mammal including but not limited to a non-human primate, sheep, or rodent (such as a rat or mouse). In some embodiments, a first subject is a donor subject and a second subject is a recipient subject. In some such embodiments the donor subject, or cells of the donor subject, may be matched to the recipient subject or cells of the recipient subject, for example, by HLA-type matching.

Vascularized Bone Grafts

In one embodiment, the present invention provides a method of preparing a vascularized bone graft, comprising: (a) obtaining a three-dimensional model of a bone portion; (b) partitioning the three-dimensional model of step (a) into two or more bone segment models; (c) preparing two or more bone graft segments, comprising: (i) obtaining a scaffold having a size and shape corresponding to each of the bone segment models of step (b); (ii) obtaining a bioreactor having an internal chamber configured to hold the scaffold; (iii) applying to the scaffold (1) bone-forming cells, or cells capable of differentiating into bone-forming cells, and (2) blood vessel-forming cells, or cells capable of differentiating into blood-vessel forming cells; (iv) culturing the cells on the scaffold within the bioreactor to form a bone graft segment; and (v) removing the bone graft segment from the bioreactor; and (d) assembling the two or more bone graft segments prepared in step (c) to form a bone graft having a size and shape corresponding to the bone portion of step (a). In one embodiment, the cells applied to the scaffold in (c) (iii) comprise pluripotent cells, induced pluripotent cells, progenitor cells, differentiated cells, or any combination thereof. In one embodiment, the cells of (c) (iii) (1) comprise bone marrow stromal cells or mesenchymal stem cells or pluripotent cells induced toward mesenchymal lineage or differentiated bone cells or any combination thereof. In one embodiment, the cells of (c) (iii) (2) comprise endothelial progenitor cells or pluripotent cells induced toward endothelial lineage or differentiated endothelial cells or any combination thereof. In one embodiment, the bone graft segment has a thickness of about one centimeter or less. In one embodiment, the bone graft segment has a thickness of about 0.3 millimeters to about 10 millimeters. In one embodiment, the assembling of the bone graft segments is carried out with an adhesive, one or more pins and holes, or both. In one embodiment, the pins are metallic or resorbable. In one embodiment, the pins are titanium. In one embodiment, the adhesive is a biocompatible bone glue, for example, a polymer such as NovoSorb™ (PolyNovo Biomaterials, Melbourne) or any gel, liquid, rubber-like substance or any other biocompatible material capable of securing together two or more bone segments. Examples of bone glues include, but are not limited to, polymer based bone glues such as polyurethane-based and polymethylmethacrylate-based bone glues. In one aspect, the invention provides a method of repairing or replacing a bone portion in a subject, comprising steps (a)-(d) described above, and further comprising transplanting the bone graft into a subject so as to repair or replace the bone portion in the subject. In one aspect, the invention provides a vascularized bone graft prepared by a method of the invention. In another aspect, the invention provides a vascularized bone graft for repairing or replacing a bone portion in a subject, wherein the bone graft comprises two or more bone graft segments, wherein the two or more bone graft segments are connected together to form a vascularized bone graft having a size and shape corresponding to the bone portion to be replaced or repaired. In some embodiments, the bone graft segments comprise bone cells derived from progenitor cells (such as mesenchymal progenitor cells), pluripotent cells (such as induced pluripotent stem cells), autologous cells (such as the subject's own cells), or any cell capable of (i) forming bone, or (ii) differentiating into a cell that is capable of forming bone. In some embodiments, the bone graft segments comprise endothelial or blood vessel cells derived from progenitor cells (such as endothelial progenitor cells), pluripotent cells (such as induced pluripotent stem cells), autologous cells (such as the subject's own cells), or any cell capable of (i) forming endothelium and/or blood vessels, or (ii) differentiating into a cell that is capable of forming endothelium and/or blood vessels. In some embodiments, each bone segment has a maximum thickness of less than about one centimeter, or has a maximum thickness of about 0.3 millimeters to about 10 millimeters.

In some embodiments the cells used in accordance with the above methods, or used in the manufacture of the above bone grafts, are derived from, or derived from a cell obtained from, the same subject into which the bone graft is to be placed such that they are autologous cells, or are derived from autologous cells. In one embodiment, the cells are derived from pluripotent stem cells, such as, for example, induced pluripotent stem cells, embryonic stem cells, cloned stem cells, or adult stem cells (such as bone marrow stem cells). In some embodiments the induced pluripotent stem cells may be derived from a somatic cell taken from the same subject into which the bone graft is to be placed or from a suitably matched donor, such as HLA-matched. In some embodiments, the cells are mesenchymal stem cells and/or endothelial progenitor cells. In some embodiments, the cells are seeded onto the scaffold at a cell ratio of 1:1, or any ratio from about 2:8 to about 8:2.

In some embodiments, the present invention provides culture vessels suitable for use in the manufacture of bone grafts, such as bioreactors described herein. Such culture vessels may be perfusion bioreactors comprising one or more custom-designed graft chambers into which a cell/scaffold construct can be inserted and cultured under press fit conditions. Bioreactors may comprise a top element and a bottom element, wherein the top element and the bottom element are secured together. In one embodiment, the top element comprises a reservoir for culture medium, a fluid outlet port and one or more fluid channels. In one embodiment, the bottom element comprises a fluid inlet port and one or more fluid channels. In one embodiment, the culture vessel is generated using computer-assisted manufacturing. In one embodiment, the computer-assisted manufacturing comprises a computer-numerical-control milling machine and/or three-dimensional printing.

In some embodiments, the graft chamber may be a custom-shaped chamber(s) that accommodates the scaffold/cell construct(s) until maturation of functional bone. In some embodiments, a graft chamber is of a size sufficient to accommodate a segment of bone having a thickness of about 0.3 millimeters to about 10 millimeters.

In some embodiments, the scaffold and/or bone segment may be positioned in the graft chamber using frames or inserts. Frames or inserts may be used to customize the size and shape of a graft chamber and position the scaffold and/or bone segment in the graft chamber, as desired, to culture the bone segment under direct perfusion, press-fit conditions to maximize the flow of fluid through the scaffold and/or bone segment, and minimize the flow of fluid around the scaffold and/or bone segment. In some embodiments the graft chamber may have a generic shape or size, but a frame(s) or insert may be used to customize the size and shape (e.g. the internal size and shape) of the graft chamber, as desired, to accommodate the scaffold and/or bone segment. Frames or inserts may be made of any suitable material, for example, a biocompatible, non-toxic, moldable plastic.

In one embodiment the present invention provides scaffolds suitable for use in the manufacture of bone grafts, for example as described herein. In one embodiment, the scaffold is generated using computer-assisted manufacturing. In another embodiment, the manufacturing comprises a computer-numerical-control milling machine, casting technologies, laser cutting and/or three-dimensional printing. In one embodiment, the scaffold consists essentially of decellularized bone tissue. In one embodiment, the scaffold comprises a synthetic ceramic/polymer composite material. In one embodiment, the scaffold consists essentially of a material capable of being absorbed by cells.

In some embodiments, the invention provides a model system for bone diseases or disorders and/or vascular diseases or disorders, the model system comprising a vascularized bone graft according to the invention. In one aspect, the invention provides a model system for bone deficiencies, defects, diseases or disorders, the model system comprising a vascularized bone graft comprising two or more bone graft segments, wherein the two or more bone graft segments are connected together to form a bone graft. In one aspect, the invention provides a method of identifying a compound that may be useful for treating a bone deficiency, defect, disease or disorder, comprising (a) contacting a bone graft, in vivo or in vitro, with a test agent, wherein the bone graft comprises two or more bone graft segments, wherein the two or more bone graft segments are connected together to form a bone graft; and (b) determining whether the test agent improves the function of, or improves the growth of, or prevents or delays degeneration of the bone graft of (a). In some embodiments the bone deficiency, defect, disease or disorder comprises congenital, pathological or traumatic defects, cosmetic procedures, degenerative disorders, surgical resection following neoplastic transformation, or chronic infection. In one aspect, the invention provides a method of identifying a compound that may be useful for treating a vascular disease or disorder, comprising (a) contacting a vascularized bone graft, in vivo or in vitro, with a test agent, wherein the vascularized bone graft comprises two or more vascularized bone graft segments, wherein the two or more vascularized bone graft segments are connected together to form a vascularized bone graft; and (b) determining whether the test agent treats or prevents or delays the progression of the vascular disease or disorder. In some embodiments, the bone graft segments comprise bone cells derived from progenitor cells (such as mesenchymal progenitor cells), pluripotent cells (such as induced pluripotent stem cells), autologous cells (such as the subject's own cells), or any cell capable of (i) forming bone, or (ii) differentiating into a cell that is capable of forming bone. In some embodiments, the bone graft segments comprise endothelial or blood vessel cells derived from progenitor cells (such as endothelial progenitor cells), pluripotent cells (such as induced pluripotent stem cells), autologous cells (such as the subject's own cells), or any cell capable of (i) forming endothelium and/or blood vessels, or (ii) differentiating into a cell that is capable of forming endothelium and/or blood vessels. In some embodiments, each bone segment has a maximum thickness of less than about one centimeter, or has a maximum thickness of about 0.3 millimeters to about 10 millimeters.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Engineering Vascularized Bone Grafts for Repairing Large Skeletal Defects

Introduction

Bone deficiencies resulting from trauma, birth defects and diseases affect an increasing number of patients worldwide, with a combined annual U.S. market for bone repair and regeneration therapies projected to reach 3.5 billion by 2017. Current treatments for these patients, which rely on the implantation of alloplastic materials or transplantation of bone tissue, are not optimal and alternative therapeutic strategies are required to restore skeletal integrity and functionality in a large number of clinical cases.

Figure 2:
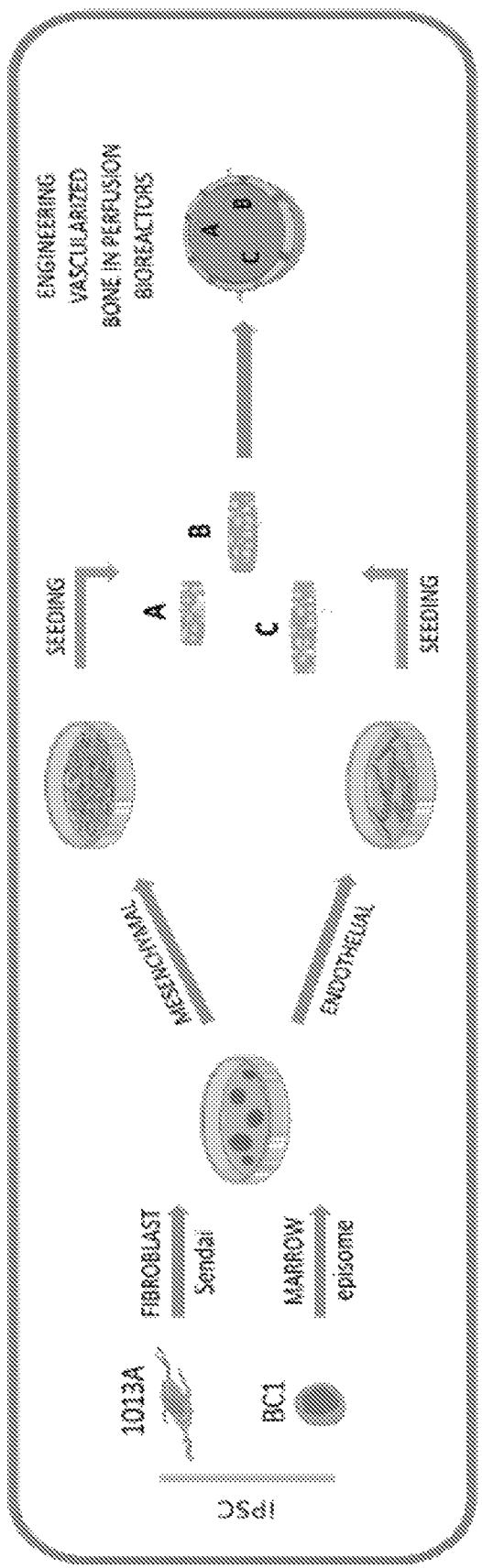
FIG. 2. Osteogenic and vascular progenitors are generated from hiPSC and co-cultured onto custom-made osteoinductive scaffolds (here, on three scaffolds labeled A, B and C) in perfusion bioreactors.
Figure 3:
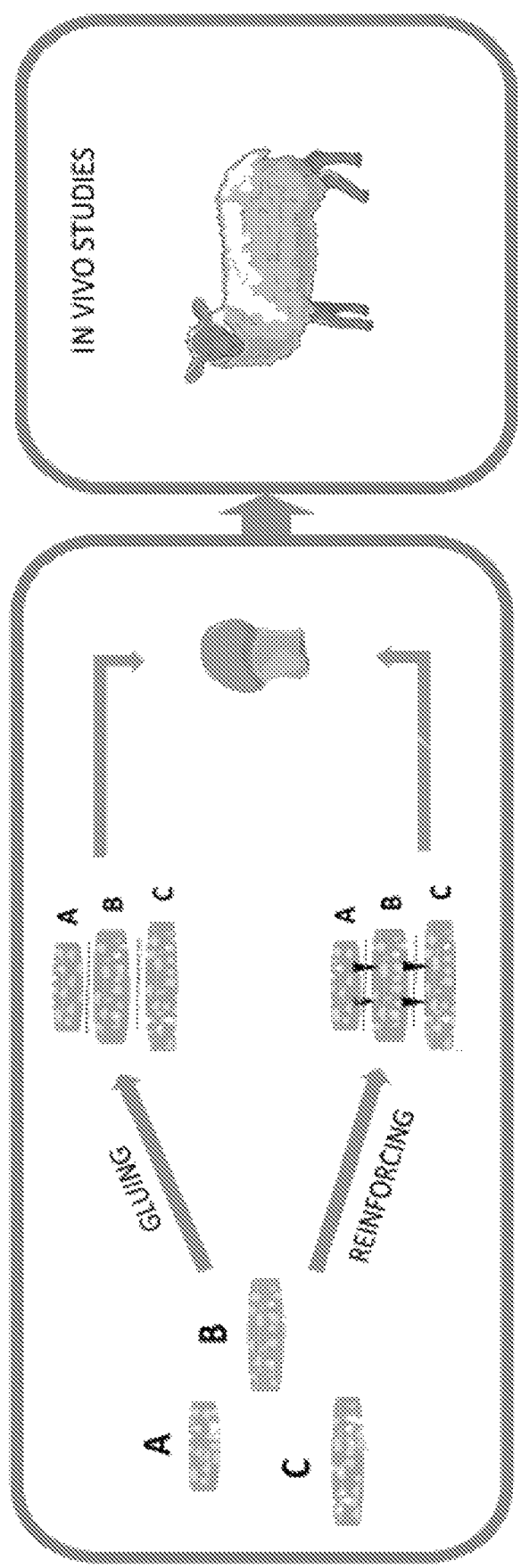
FIG. 3. Engineered vascularized bone segments (here, three segments labeled A, B and C) are assembled using biocompatible bone glues and/or reinforced using 3D printed titanium pins and holes. Additional studies can be designed to repair clinically relevant skeletal defects in large animals.

This Example proposes a strategy for engineering vascularized bone grafts from human induced pluripotent stem cells (hiPSCs) for enhanced healing of complex skeletal defects. In particular, the ability to derive autologous osteogenic and vascular cells constituting healthy bone from hiPSCs for any patient in virtually unlimited numbers represents an unprecedented therapeutic resource. Vascularized bone substitutes will be engineered using a biomimetic scaffold-bioreactor approach of bone development. Computer-aided and rapid prototyping technologies will allow the preparation of bone substitutes of any shape and size. Digital models of large bone defects will be created and then segmented in complementary sub-parts that will be used to produce customized biomaterial scaffolds and bioreactors via computer-aided design and manufacturing technologies, such as 3D printing (see, FIG. 1). The proposed engineering strategy overcomes the limitations associated with perfusion culture of large bone grafts. Mesenchymal and endothelial progenitor cells will be derived from hiPSCs generated using any available reprogramming method, and then combined with compliant scaffolds and cultured in perfusion bioreactors until maturation of functional vascularized tissue (see, FIG. 2). Engineered bone segments will then be assembled together (lego-like approach) using a biocompatible bone glue, and/or reinforced using 3D printed titanium holes and pins to match the shape and dimension of the original defect. Future studies will be aimed at exploring the therapeutic potential of hiPSC-engineered bone using different animal models of complex skeletal defects (see, FIG. 3).

Engineering large and geometrically defined vascularized bone grafts from hiPSCs represents a novel solution for the treatment of skeletal defects characterized by severe bone loss, and opens the opportunity to provide personalized therapies to a large number of patients. As importantly, such bone grafts represent qualified models to study bone development and pathologies, as well as screening new drugs and test biomaterials.

The Example describes studies designed to engineer vascularized bone grafts from human induced pluripotent stem cells (hiPSC) for enhanced healing of skeletal defects. Patient-specific bone grafts will be engineered using a biomimetic scaffold-bioreactor approach of bone development in vitro, and customized to meet specific clinical needs with the aid of computer-assisted and rapid prototyping technologies. Engineering patient-specific customized bone grafts could be used to develop innovative treatments to restore skeletal integrity and functionality in clinical situations characterized by severe bone loss.

Skeletal reconstructive therapies are needed to obviate bone deficiencies associated with, for example, reconstruction of congenital and traumatic skeletal defects, cosmetic procedures, degenerative disorders and surgical resection following neoplastic transformation and chronic infection. The worldwide market for bone replacement and repair therapies is massive, and the need for bone tissue substitutes constantly increasing due to the rapid growth of human population and extension of life expectancy. Today, the number of elderly reporting age-related fractures is estimated to be over 100 million per year worldwide, and this number is projected to constantly increase during the next decades, with the number of elderly people (+65 years) estimated to be about 2 billion by 2050. New approaches are therefore required to develop effective therapies for complex bone reconstructions. Biomimetic tissue engineering strategies have recently been explored for the ex vivo cultivation of functional bone substitutes by interfacing osteocompetent cells to biomaterials under appropriate culture conditions in bioreactors, which provide mechanical stimulation and a proper environment that guide functional tissue maturation. Attempts to engineer geometrically defined bone substitutes have been reported recently, culturing human mesenchymal stem cells in an osteoinductive scaffold-perfusion bioreactor system. However, restrictions associated with 1) the limited regenerative potential of stem cells derived from adult tissues, 2) lack of vascularization and 3) culture of large bone substitutes in direct perfusion bioreactors were not addressed, but all affect the ability to engineer functional grafts for enhanced healing of large and complex skeletal defects. In particular, engineering large cell/scaffold constructs is cumbersome using direct perfusion bioreactors, due to the resistance provided by the large constructs to the flow. The development of new tissue inside the scaffold progressively limits the perfusion of the fluid through the construct, with negative consequences on the functionality of the perfusion system. Independent studies demonstrated that a similar scenario could be seen when culturing 4×4 mm constructs in direct perfusion bioreactors for 5 weeks.

This Example proposes studies to engineer vascularized bone substitutes from hiPSCs, and adopt a combination of medical imaging procedures, computer-aided technologies and rapid prototyping to allow the construction of clinically relevant bone substitutes in perfusion bioreactors. The strategy represents a novel and innovative solution to cope with the burden of bone deficiencies, whose clinical translation will have profound social impact by improving the health status and quality of life of many patients. These studies will also provide new insights into hiPSC biology, which are critical to understand functional differentiation of pluripotent stem cells into mature tissues and organs. Additionally, hiPSC-engineered vascularized bone grafts would provide valuable high-fidelity models to investigate tissue development in normal and pathological conditions, and test new pharmaceuticals and biomaterials within a context that resembles several aspects of the native bone environment.

Background

Bone displays intrinsic capacity to regenerate and self-repair but this ability is limited to small fractures and reconstructive therapies are needed in a large number of clinical conditions to restore tissue integrity and functionality. Current treatments are based on the transplantation of autogeneic and/or allogeneic bone grafts, or implantation of graft materials with osteoconductive and osteoinductive properties. Autogeneic bone grafts represent the gold standard treatment for bone replacement procedures, due to immune tolerability and provision of essential components supporting bone regeneration and repair, but limited availability and donor site morbidity often restrict their clinical use. On the other hand, allogeneic decellularized bone grafts are available in large amounts but integrate slowly, carry the risk of infection transmission and may display immune incompatibility leading to transplant rejection. Implantation of alloplastic materials overcomes some of the restrictions encountered with autogeneic and allogeneic grafts, including disease transmission, complex shape and availability, but display poor integration, frequently result in biomaterial-associated infection, and lack biological functionality and mechanical compliance, leading to implant failure and substitution. Bone tissue engineering represents a promising therapeutic solution, since it opens the possibility to engineer an unlimited amount of viable bone substitutes to meet specific clinical needs. Human mesenchymal stem cells (hMSC) derived from adult tissues have been extensively used for bone engineering applications with encouraging results, but exhibit restricted potential for clinical applications due to limited availability, inadequate regenerative potential and decrease in functionality associated with in vitro expansion and donor age.

Autologous bone substitutes in the size range of ~1 cm have been grown from adult stem cells and used to facilitate bone healing in experimental animals and in humans. However, their scale-up to clinical sizes and functionality are limited due to the lack of blood supply, and limited proliferation and vasculogenic potential of cultured adult stem cells. An appropriate blood supply has been recognized as an essential component of normal fracture healing and defective angiogenesis at the fracture site has been a primary consideration when poor outcomes occur. Poor blood supply leads to hypoxia and necrosis of the grafted tissue, and can result in decreased bone formation ("atrophic bone"). Similarly, implantation of large cellularized bone substitutes without the connection to vascular supply can result in cell death in the interior regions of the transplant. To expedite cell survival and bone regeneration, recent tissue engineering approaches have involved transplantation of endothelial progenitors or vascular networks within bone substitutes. Studies have shown the positive effects of endothelial cells and osteogenic cells in direct co-culture model. In addition, studies suggest that co-transplantation of endothelial cells and BMSC promoted new bone formation in vivo, and that endothelial networks engineered within bone substitutes can functionally anastomose with the host vasculature.

Pluripotent stem cells display high regenerative potential and ability to differentiate toward all specialized cells constituting healthy bone tissue. When derived using nuclear reprogramming technologies, pluripotent stem cells allow the construction of patient-specific bone substitutes for personalized applications. Both mesenchymal and endothelial progenitor cells have recently been derived from pluripotent stem cells, opening new opportunities for the unlimited construction of vascularized bone substitutes for enhanced reconstructions of large skeletal defect. It is therefore important to explore the possibility to engineer vascularized bone grafts from induced pluripotent stem cells, in order to develop safe and effective treatments for many patients affected by severe skeletal defects and bone disorders.

Results

The inventors have extensive experience with cultivation of bone substitutes from mesenchymal stem cells derived from adult tissues and from human pluripotent stem cells. A set of studies exploring the relative regenerative potential of hMSCs and mesenchymal progenitors derived from human embryonic stem cell (hESC) lines have demonstrated comparative advantages of hESC-derived mesenchymal progenitors for bone engineering applications. Studies in monolayer and 3D cultures on scaffolds in bioreactors have shown that hESC-derived mesenchymal progenitors highly resemble hMSCs in terms of morphology, surface antigen and global gene expression profile, but display higher proliferation potential, biosynthetic activity and mineralization properties, all paramount features for the unlimited construction of functional substitutes for bone engineering applications. The derivation protocol has been extended to hiPSC lines generated from different tissues and using different reprogramming technologies based on non-integrating vectors, opening the possibility to engineer safe patient-specific bone substitutes for personalized applications. hiPSC lines were characterized by immunohistochemistry to assess pluripotency and karyotyped, before being induced toward the mesenchymal lineage for 7 days. Mesenchymal-like phenotype was characterized by flow cytometry and by probing surface marker expression and differentiation potential in monolayer (osteogenesis, adipogenesis) and pellet cultures (chondrogenesis). Differentiation toward the osteogenic lineage was confirmed by alkaline phosphatase and mineralization, differentiation toward the chondrogenic lineage was shown by glycosaminoglycans, and differentiation toward the adipogenic lineages was shown by lipid characterization.

Cells were then seeded on decellularized bone scaffolds (4 mm Ø×4 mm height), and cultured in osteogenic medium under constant perfusion (linear flow velocity of 800 µm/sec) for 5 weeks before 12-week subcutaneous implantation in immunocompromised mice to assess stability and further tissue maturation. Histological and immunohistochemical analyses of engineered bone were carried out following bioreactor cultivation and subcutaneous implantation in immunocompromised mice. Micrographs showed maturation of phenotypically stable bone-like tissue and vascularization. MicroCT analysis of engineered bone showed an increase in mineral density and structural parameters.

Altogether the results demonstrate that mesenchymal progenitors can be derived from hiPSC lines, and used to engineer mature and phenotypically stable bone tissue for repair treatments of skeletal defects in personalized applications. In all studies, perfusion bioreactors were shown to be particularly important for bone development, as they provide biomechanical stimulation to the cells, and support survival of the cells in the interior of the constructs, resulting in the production of thick homogenous bone-like matrix. Studies are now directed at developing suitable protocols for engineering vascularized bone substitutes for enhanced healing of large and geometrically complex skeletal defects. Preliminary studies have shown that functional endothelial progenitors can be derived from hESC lines. Following differentiation of embryoid bodies in controlled conditions, isolated CD34 positive cells were able to specifically internalize DiI-Ac-LDL and form tubes when plated on Matrigel™. This approach is being translated to hiPSCs for the construction of patient-specific multicellular composite bone substitutes.

In addition, preliminary vascularization studies in 3D cultures have shown that co-culture of hiPSC-derived mesenchymal progenitors and human bone marrow stromal cells (BMSC) with human umbilical vein endothelial cells (HUVEC) result in long-lasting formation of vascular networks, both when cells are embedded in fibrin clots or seeded onto decellularized bone scaffolds, which represent more compliant substrates for skeletal repair treatments. Interestingly, number and stability of vascular structures were similar when HUVEC were cultured with hiPSC-derived mesenchymal progenitors and human BMSC in fibrin clots. Epifluorescence micrographs showed the presence of stable 3D vascular networks 3 weeks after seeding. Hematoxylin/Eosin staining of clot cross sections showed the presence of hollow vessels across the entire construct for both co-culture of mesenchymal progenitors derived from hiPSC line 1013A and BMSC with HUVEC 4 weeks after seeding. To follow the formation of vascular network in vitro, cell populations were specifically labeled with different Vybrant tracker dyes before embedding in fibrin clots, and cultured for 4 weeks in a mixture of osteogenic and endothelial inducing media before harvesting for histological analysis. No vascular structures were observed when HUVEC were cultured alone, suggesting the pivotal role of mesenchymal cells to support and guide tissue vascularization. Studies can be carried out to identify the molecular mechanism underlying this finding in order to develop improved protocols to support maturation of vascularized bone tissue in vitro.

Similar outcomes were observed when cells were seeded onto decellularized bone scaffolds (8 mm Ø×2 mm height) and cultured for 6 weeks under osteogenic- and vascular-inducing conditions. The maturation of bone-like tissue, evidenced by the positive staining for osteocalcin, osteopontin and bone sialoprotein, was accompanied by the formation of networks of hollow vessels inside the constructs. Immunohistochemical examination showed that the tubular structures were positive for the endothelial marker CD31.

Different seeding ratios, and culture conditions can be tested to explore the potential to enhance the formation of vascularized bone tissue, as well as to assess the potential of other hiPSC lines for engineering vascularized bone grafts. Future studies are aimed at exploring the effect of dynamic conditions in perfusion bioreactors on the vascularization process. Development of proper vascularization protocols, in combination with the biomimetic osteoinductive scaffold-perfusion bioreactor approach, will allow the construction of vascularized bone grafts for personalized repair treatments of complex skeletal defects.

Research Design and Methods

This Example proposes the engineering of vascularized bone grafts from hiPSCs using a stepwise differentiation approach, starting with derivation of lineage-specific osteogenic and endothelial progenitors, and subsequent co-culture of these progenitors in a "biomimetic" scaffold-bioreactor model, which ensure controlled development of functional bone tissue in vitro. Computer-aided and rapid prototyping technologies will be employed to enable the fabrication of custom-made bone substitutes for the reconstruction of large and geometrically complex skeletal defects. Engineering patient-specific custom-made bone grafts can be used to develop innovative treatments to restore skeletal integrity and functionality in clinical situations characterized by severe bone loss. This Example describes three sub-projects as described below.

1. Computer-Aided Design (CAD) of Skeletal Models and Computer-Aided Manufacturing (CAM) of Biomaterial Scaffolds and Perfusion Bioreactors.

The objective of Part 1 is to create and elaborate digital models of skeletal defects to guide the design and manufacturing of customized biomaterial scaffolds and perfusion bioreactors. Digital models of skeletal defects will be created and segmented into complementary sub-parts using CAD software, then these models will be used as a reference for the computer-aided fabrication of biomaterial scaffolds of corresponding size and shape and custom-made perfusion bioreactors. Bioreactors will be machined and/or free-form fabricated using the digital models in order to accommodate each specific cell/scaffold construct in a press-fit fashion and allow culture under direct perfusion.

Digital models of skeletal defects will be created using CAD software (e.g., Autocad™, Solidworks™, ProE™, Creo™). To validate the therapeutic potential of the proposed engineering strategy, this approach can be extended to defect models of different size and shape. Reference models of skeletal defects in CAD will be edited and segmented into smaller complementary sub-parts (lego-like building parts) that can be cultured in perfusion bioreactors without affecting the perfusion system. The segmented bone sample files will then be saved in compatible IGES or SLT formats and imported in CAM software (e.g., SprutCAM™). The generated files in CAM software will then be processed to generate the appropriate G-Codes to drive a computer-numerical-control (CNC) milling machine (e.g., Tormach™, Bridgeport™), select appropriate machining tools bits and program the machining paths to cut the scaffolding materials into the desired segmented shapes. Plugs of trabecular bone (cow and/or human) of adequate size will be drilled, cleansed under high-pressure streamed water to remove the bone marrow, and then sequentially washed to remove cellular material as previously described (de Peppo et al., *Proc Natl Acad Sci USA* 110(21):8680-5 (2013)). Decellularized bone plugs will then be freeze-dried, and used for the fabrication of scaffolds corresponding to the shape and size of the segmented samples of the skeletal defect. The potential to use synthetic, resorbable and mechanically compliant ceramic/polymer composite materials will be explored in parallel, since it represents an essential requisite for the reproducible and large-scale fabrication of bone substitutes for clinical applications. Fabricated scaffolds will be sterilized and conditioned in culture medium overnight prior to cell seeding. The segmented bone sample files edited in CAD will then be used to design customized bioreactor, which can accommodate the cell/scaffold construct(s) in a press-fit fashion under direct perfusion conditions. Again, the CAD files will be converted into compatible formats and imported into CAM and/or 3D printer software, and used to fabricate the bioreactors using different plastic materials. Each bioreactor will be constituted of two parts (top and bottom) that will be secured together, for example, by means of metallic screws. The cell/scaffold constructs will be cultured in between the top and bottom elements. The bottom part will include key elements including but not limited to the inlet port and channels for flow perfusion, as well as anatomically shaped chambers to accommodate the cell/scaffold constructs. The top part will include elements such as a medium reservoir and the outlet port for flow perfusion. A system of tubes can be used to connect the inlet and outlet ports and allow perfusion throughout the bioreactors via the control of a peristaltic pump.

2. Engineering Vascularized Bone in Custom-Made Perfusion Bioreactors.

The objective of Part 2 is to engineer vascularized patient-specific bone grafts in vitro. hiPSC lines reprogrammed from different tissues using non-integrating vectors will be induced toward the mesenchymal and endothelial lineage prior to culture under biomimetic conditions in the osteoinductive scaffold-perfusion bioreactor system to guide maturation of functional vascularized bone tissue.

hiPSC reprogrammed using non-integrating vectors from different donors and source tissues (line BC1 and 1013A) will be expanded, characterized for pluripotency and karyotyped before induction toward the mesenchymal and endothelial lineages. Derived progenitor cells will be expanded, characterized by flow cytometry, and karyotyped to assess genetic normality. Qualitative and quantitative methods will be used to evaluate osteogenic and endothelial phenotype in vitro, including histological and immunohistochemical examination, biochemical and morphological assays, and gene expression analysis. Vascular induction will be tested in monolayer cultures and embryoid bodies, in the presence of specific factors (BMP-4, activin, bFGF, VEGF). Differentiated progenitors will be sorted based on surface antigen expression (CD34, CD31, KDR, C-KIT) and cultured in endothelial media. Progenitor yield, viability, proliferation and phenotype-expression of specific markers (CD31, vWF, VE-cadherin, SMA) will be assessed by flow cytometry, immunofluorescence and gene expression. Network formation and sprouting will be tested by encapsulation in collagen/fibronectin/Matrigel™ before co-cultivation studies. Commercially available BMSC (Lonza) and HUVEC (Lonza) will be used as reference lines to assess the quality and functionality of hiPSC-derived mesenchymal and endothelial progenitors. To engineer vascularized bone tissue, hiPSC-derived mesenchymal and endothelial progenitors will be co-seeded onto decellularized bone scaffolds (or others) and cultured in bioreactor in a mix of osteogenic and endothelial medium. Pre-differentiation, cell seeding ratios, concentration of differentiation factors and use of fibrin sealants will be explored to design optimal culture conditions for the development of fully vascularized bone grafts in vitro. Culture in bioreactors will be conducted for a period of 3-5 weeks, until the formation of a mature vascularized tissue. Tissue development will be assessed using qualitative and quantitative methods, including histological and immunohistochemical examination, biochemical assays, high-resolution characterization techniques (SEM, FIB-TEM, Tof-SIMS), imaging procedures (microCT) and mechanical testing (Young's modulus, tensile and compressive strength).

3. Gluing of Engineered Bone Segments and Evaluation of Stability.

The objective of Part 3 is to fabricate custom-made bone grafts for complex skeletal reconstruction. Engineered vascularized bone segments will be assembled to match the shape of the skeletal defect by means of a biocompatible bone glue, or reinforced using 3D printed metallic (for example, titanium) or resorbable pins and holes. Future studies will be aimed at exploring safety and efficacy of engineered bone in animal models of critical-sized skeletal defects (both in loading and non-loading anatomical locations).

Engineered bone segments will be assembled to match the shape of the model of skeletal defect by means of a biocompatible bone glue for welding large bone grafts or reinforced using 3D printed metallic (for example, titanium) or resorbable pins and holes. Future studies will be aimed at exploring the safety and regenerative potential of engineered bone in animal models of complex critical sized skeletal defects (both in loading and non-loading skeletal locations). For example, digital models of femoral head defects in adult animals will be created using medical imaging procedures (CT scan) and 3D images processed and segmented (as described above) and used to engineer vascularized bone as described herein. Femoral head ostectomy will then be performed in the animals to remove the femur head to an extent matching the digital model generated (as described above), and the engineered vascularized bone place in site to restore skeletal integrity and functionality. Tissue development, healing and quality of regenerated tissue will be evaluated in vivo using medical imaging procedures and following explanation using histological and immunohistochemical techniques, high-resolution characterization techniques (e.g., SEM, FIB-TEM, Tof-SIMS), and mechanical testing (e.g., Young's modulus, tensile and compressive strength).

As described herein, vascularized bone grafts can be engineered using osteogenic and endothelial progenitors derived from human induced pluripotent stem cells for personalized reconstructive therapies. Although endothelial progenitors can be derived from both hESCs and hiPSCs, the derivation efficiency is low and the derived progenitors display scarce proliferation ability, which limits the possibility to generate enough cells for engineering large vascularized bone substitutes. To speed up the development of suitable vascularization protocols, in parallel to optimizing the derivation of highly proliferative endothelial progenitors from hiPSCs, commercially available HUVECs can be used, and then the protocols can be translated to endothelial progenitors derived from hiPSCs. The hiPSC-derived mesenchymal progenitors may be expanded to a required amount before induction toward the endothelial lineage, and then used to engineer vascularized bone substitutes.

As described herein, the engineered bone substitutes can be assembled to match the shape of the skeletal defect using a biocompatible bone glue for welding large bone grafts, which might be insufficient to ensure a stable connection following implantation in high load-bearing locations. To solve this problem, alternative solutions will be tested, including reinforcement using 3D printed metallic or resorbable pins and holes.

Human Stem Cells

A stepwise protocol is proposed for preparation of vascularized bone grafts from human iPSCs, which will include: (a) differentiation and expansion of osteogenic and vascular progenitors from human iPSCs, and testing their functional potential for new tissue formation; (b) preparation and seeding of decellularized bone scaffolds or any other biocompatible and resorbable biomaterial scaffolds; and (c) cultivation of osteogenic tissue phase in conjunction/sequence with formation of microvascular network.

Cell lines: Human iPSC lines 1013A (derived by Sendai virus in the NYSCF laboratory) and BC1 (derived by episomal plasmid vector, from Life Technologies) can be used. Initial studies will be done in parallel with ESC line H9 (from Wicell Research Institute) and commercially available adult cells (BMSC and HUVEC from Lonza).

Sources of Materials

Human iPSC line BC1 was obtained from Life Technologies. This line, originally derived from the bone marrow of an anonymous donor, was published in Cell Research (18 Jan. 2011). This line is being used as a control line against which future control lines will be tested.

Human iPSC line 1013A was derived at the New York Stem Cell Foundation laboratory from a skin biopsy.

Reference BMSC and HUVEC lines are commercially available and can be purchased from Lonza.

Conclusions

The data generated from this protocol are expected to provide a proof of concept for development of vascularized bone substitutes from hiPSC. New insights will be gained into bone formation and vascularization by hiPSC cultured under biomimetic conditions, using scaffolds and bioreactors. Additionally, engineered vascularized bone substitutes would provide valuable high-fidelity models for quantitative in vitro studies of bone development and disease as well as drug and biomaterial testing (see, e.g., Example 2), within a context that resembles selected aspects of the native bone environment.

Example 2

A Biomimetic Platform to Screen Implant Materials In Vitro

An in vitro screening platform for biomedical implants is developed using engineered bone. The screening platform contributes to the establishment of alternative methods to animal testing according to the 3Rs principle (Replacement, Reduction and Refinement; see, below). Bone grafts are engineered as experimental platforms to screen implant materials. Bone grafts are engineered from induced pluripotent stem cells (iPSCs) using a biomimetic approach of bone development in vitro, and used as alternative to animal testing to screen and develop materials with chemical and topographic features suitable for implantation. The 3D screening platform is validated for metal implants comparing animal, human and synthetic engineered bone.

Relevance for the 3R Field

Craniofacial and skeletal bone deficiencies cause pain, discomfort and psychological distress to the patient. These conditions can be ameliorated via implantation of alloplastic materials, whose development however requires extensive animal testing and long time periods. Alternative human-relevant methods can be used to screen efficacy and safety of new implants without using animal models, and contribute to the development of products with higher clinical potential.

Using the proposed screening platform animals are not just reduced, but could fully be replaced on the long-term. In fact, the fine characterization and understanding of the biological and chemical phenomena occurring at the bone-implant interface could help developing new implant surfaces using a knowledge-driven approach for direct applications in human patients. The present invention can be used for the screening of new implant materials more cheaply, faster and in high-throughput fashion without the need for animal testing.

Developing In Vitro Screening Platforms Using Engineered Bone Grafts.

Bone grafts are engineered by combining iPSC-derived mesenchymal progenitor cells, decellularized bone scaffolds and implant materials to be screened. Bone grafts are grown using a biomimetic approach of bone development in vitro, and used to study the cellular response to the implant material, the strength of interaction of the implant with the engineered bone tissue, and the quality of the bone-implant interface.

The geometrical form of the platform is standardized to insert titanium mini-implants (screws, about 6 mm in height and 2 mm in diameter) into decellularized bovine bone scaffolds. For comparison reasons the Ti-implants are machined and sterilized. Machined surfaces constitute the majority of the published results from animal and clinical studies. Also modern Ti-surfaces are further optimized for optimal bone contact and even for bone bonding, i.e., bioactive surface. With the objective to draw accurate conclusions regarding the effects of implant surface, the chemical and topographic characteristics of the implants are studied using surface profilometry, electron microscopy, X-ray photoelectron spectroscopy (XPS) and computed tomography (CT). Plugs of trabecular bone (8 mm in diameter) are drilled from the subchondral region of meta-carpal joints of calves. Soon after, plugs are cleansed under high-pressure streamed water to remove the bone marrow and then sequentially treated with different washing solutions to remove the cellular and genetic material. Following decellularization, bone plugs are freeze-dried and cut to a final dimension of 3-4 mm in thickness and 8 mm in diameter. Each individual scaffold is weighted and measured to calculate the density. Following, the implants are inserted into decellularized bovine bone scaffolds (3-4 mm in thickness and 8 mm in diameter) using a motorized torque wrench with select rotation speed. The implant is screwed throughout the entire thickness of the scaffold and, after sterilization in 70% ethanol overnight, the implant-scaffold constructs are used to measure the mechanical stability of the interaction using removal torque testing.

Mesenchymal progenitor cells are derived from human iPSC lines available at NYSCF (line 1013A and/or BC1) and/or a NIH-registered line using a previously established protocol to generate large amount of progenitor cells and, following thorough characterization, seeded onto decellularized bone scaffolds anchoring the Ti implants. Constructs seeded with commercially available BMSCs, which are recognized to give rise to bone-forming cells and form bone tissue in vitro and in vivo, are used as reference for all experiments. Cells are seeded at different densities (1 to 3 million per sample) to study the effect of initial cell mass on tissue formation and implant integration. Constructs seeded with cells are cultured under osteogenic conditions for 5, 7 and 10 weeks. During the culture period, cell proliferation is estimated weekly using the PrestoBlue™ assay. Culture medium is collected at each change to study the release of bone-specific proteins (gla-type osteocalcin and osteopontin) via ELISA and cytotoxicity via measuring the amount of lactate dehydrogenase. After culture, the samples are harvested to determine cell viability, the biological response to the implant material, the strength of interaction of the implant with the engineered bone tissue and the quality of the bone-implant interface.

The biological response to the materials is determined via molecular biology technologies. Osteogenic differentiation is assessed by studying the expression and production/activity of bone-specific genes and proteins, including RUNX2, COL1A1, ALPL, OPN, OC and PDGFRB via real time PCR, Western blot and enzymatic assays. Genotoxicity is determined via karyotyping using the Nanostring™ technology. Cells are detached from constructs using a combination of collagenase and trypsin treatment, expanded to the required number, and then lysed to isolate the DNA for analysis. Tissue formation and mineralization, with a major interest toward the bone-implant interface, is evaluated via micro-CT (µCT) analysis and histological and histochemical methods. For histology, samples are embedded in PMMA plastic, cut lengthwise into sections, ground and stained with Stevenel's blue followed by van Gieson picro-fuchsin and Goldner's Masson trichrome stain. To evaluate bone matrix deposition, samples are demineralized, embedded in paraffin, cut and stained against osteopontin, bone sialoprotein and osteocalcin. One key parameter to determine is the biomechanical properties of the biomaterial—engineered bone system, e.g., removal torque and push-out strength. For this to be meaningful the testing needs to be standardized and evaluated for size of implants and insertion forces (torque) (see, Johansson et al., *Clin Implant Dent Relat Res* 14(4):603-11 (2012); see also, Buser et al., *Int J Oral Maxillofac Implants* 13(5):611-9 (1998)).

Assessing the Effect of Scaffold Origin on the Quality of the Screening Platform.

To study the effect of interspecies differences in bone quality on tissue growth and implant stability and integration, screening platforms are generated as described herein using either decellularized cow bone or decellularized human bone, and the effects of scaffold origin on the quality of tissue formed, the strength of interaction of the implant with the newly formed tissue, and the quality of the bone-implant interface are studied.

Titanium screws are manufactured and characterized as described herein. Plugs of trabecular bone (8 mm in diameter) are drilled from the subchondral region of meta-carpal joints of calves and human cadaveric tissues, processed and cut as described herein. Cadaveric bone specimens are provided by LifeNet Health®. Each individual scaffold is weighted and measured to calculate the density. A combination of medical imaging procedures, electron microscopy, high-resolution characterization methods and mechanical testing is used to study and compare the structure, composition and quality of scaffolds derived from decellularized human or cow bone. Characterization results are used to find any relevant correlation between the nature of the scaffold, the formation of new tissue and the extent of the interaction of the implant with the engineered bone. After characterization, Ti implants are placed in decellularized bone scaffold samples as described herein, and constructs are seeded with iPSC-derived mesenchymal progenitor cells and cultured under osteogenic conditions for several weeks (the optimal number of weeks is established as described herein). Cell attachment, viability and proliferation, the quality of tissue formed, the strength of interaction of the implant with the newly formed tissue, and the quality of the bone-implant interface are studied as described herein.

Assessing the Effect of Culture Systems on the Quality of the Screening Platform.

The effect of dynamic conditions in perfusion bioreactors on tissue growth and implant-tissue interaction in vitro is studies by generating screening platforms (as described herein), culturing them under static and dynamic conditions in perfusion bioreactors, and studying the effects of perfusion on the quality and amount of tissue formed, the strength of interaction of the implant with the newly formed tissue, and the quality of the engineered bone-implant interface.

Figure 18:
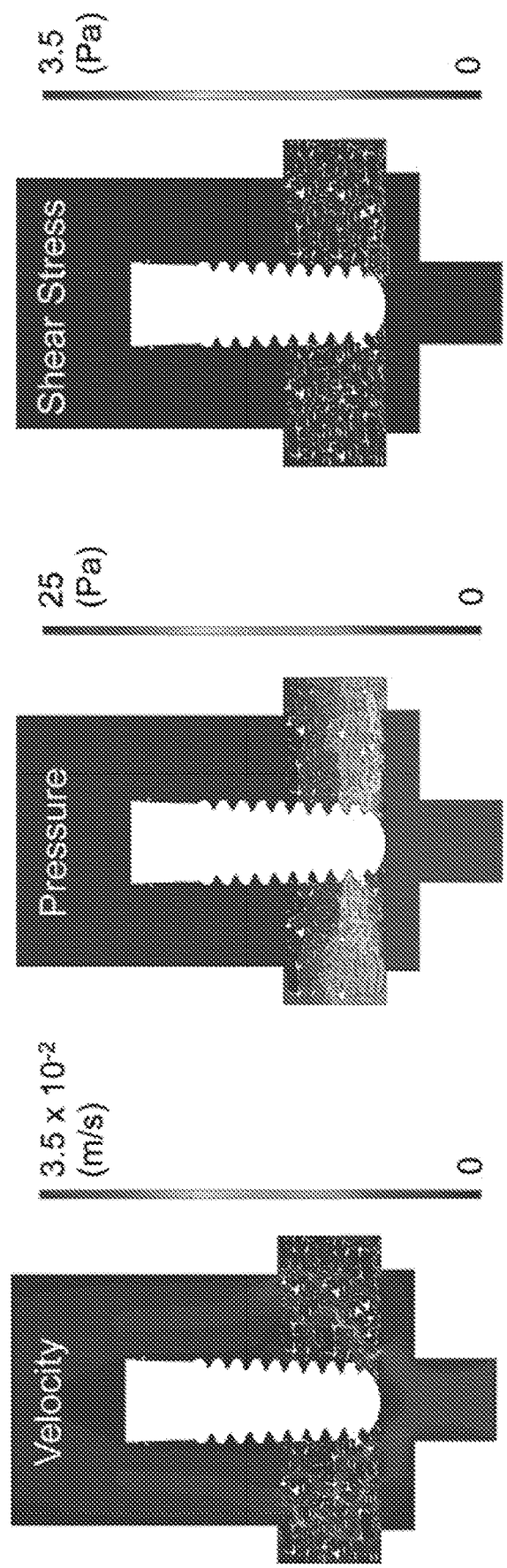
FIG. 18. Simulation studies in Comsol Multiphysics™ showing the fluid dynamics within a perfusion system for bone samples interlocked with implant materials. The results show negligible effect played by the implant on fluid velocity and pressure, as well as on the shear stress applied to the cells across the volume of the bone-implant constructs.
Figure 19:
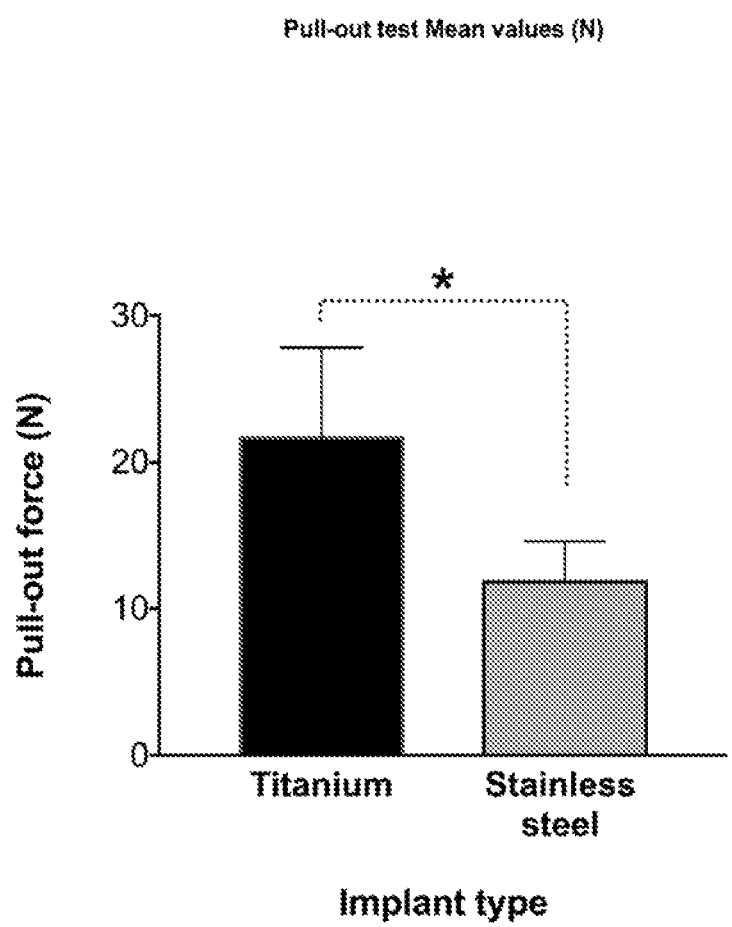
FIG. 19 is a graph of a comparison between pullout force required to extract implants (titanium and stainless steel) after insertion into decellularized bone scaffold, seeding with bone progenitor cells and culturing as discussed in Example 3.

After determining the effect of decellularized bone scaffolds (cow and human), the effect of dynamic conditions is explored in perfusion bioreactors on the quality and amount of tissue formed, the strength of interaction of the implant with the newly formed tissue, and the quality of the engineered bone-implant interface. Constructs of iPSC-derived mesenchymal progenitors and decellularized bone scaffolds anchoring the implants are cultured for different weeks under static and dynamic conditions, using perfusion regimes previously established (a uniform flow rate of 3.6 ml/min corresponding to the interstitial velocity of 0.8 mm/s) (Grayson et al., *Biotechnol Bioeng* 108:1159-1170 (2011)). In order to estimate the degree of shear stresses applied to the cells under dynamic conditions, and explore the possibility to identify perfusion regimes corresponding to stresses of higher physiological relevance, a combination of medical imaging procedures, 3D image processing, digital design and simulation software is used. DICOM files generated from CT scans are used to reconstruct a 2D image of the scaffolds along the direction of perfusion, and the model anchoring the implant placed into a perfusion system framework in COMSOL Multiphysics™ to simulate the hydrodynamic environment (FIG. 18). Cell attachment, viability and proliferation, the quality of tissue formed, the strength of interaction of the implant with the newly formed tissue, and the quality of the bone-implant interface is studies as described herein.

Assessing the Potential of Synthetic Scaffolds for Engineering the Screening Platform.

The potential of using synthetic scaffolds to screen implant materials is explored by manufacturing cement scaffolds with specified chemical composition and porosity similar to bone, seeding them with iPSC-derived mesenchymal progenitor cells, and studying their potential for screening implant materials as described herein.

To avoid drawbacks with biological scaffolds, including high cost and extensive processing time, a dissolving phase approach to manufacture bone cement scaffolds with different porosity and mechanical properties was developed. From a material point of view, it should be possible to shape the scaffold into complex geometries, and the scaffold material should have a chemical composition suitable for bone regeneration and contain interconnected pores of adequate size (for cells to be able to penetrate). Bioceramic materials with similar chemical composition as natural bone can be designed including macro-porous features to also resemble the natural morphology. The bioceramic technology is based on calcium phosphate cement chemistry (CPC). CPCs can in general be found from two different chemistries, apatite cements (neutral to alkaline pH) or brushite cements (acidic pH) (Ginebra et al., *Acta Biomater* 6(8):2863-73 (2010)). The natural bone has apatite as the calcium phosphate phase and the formation of the apatite is from a precipitation type of chemistry involving cell activity. Synthetic materials with similar chemistry are not as amenable to manufacture using precipitation type of bonding reactions and instead a cement reaction can be used. Both brushite and apatite types of cements are molded into the desired shape and macro pores are created via addition of a dissolving phase of polyethylene glycol particles (PEG) (Unosson et al., *J Biomed Mater Res B* (2015)). The molded cement is hardened in a moist and heated environment (e.g., 37 degrees C. in a 100% relative humidity) followed by hardening in phosphate buffered saline at 37° C. for two days. Hardened scaffolds are evaluated for diametral tensile and compressive strength, and via X-ray diffraction, scanning electron microscopy. Pore size distribution are determined from microscopy images and cross-section analysis. The scaffold can then be handled and testing is performed according to the input from methods described herein. Constructs of decellularized bone scaffolds are used as control for all experiments. Results from these studies may include knowledge of optimal chemical composition and macro porosity for also assessing the possibility of replacing the need for natural bone in the screening method.

Figures 13A, 13B, 13C, 13D, 13E, 13F:
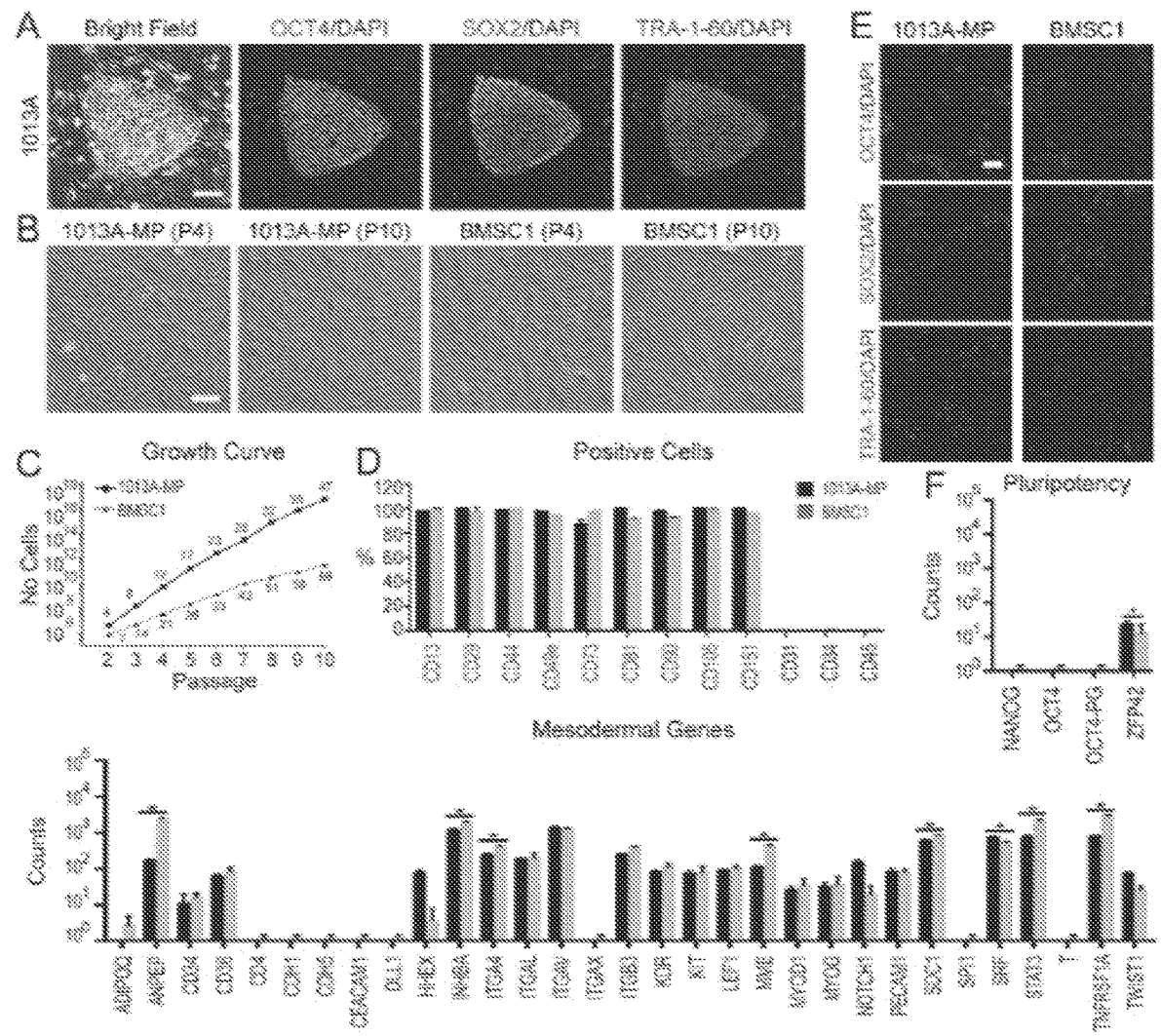
FIGS. 13A-13F are a series of representations relating to phenotypic characteristics of human iPSC-MP cells.

The inventors have extensive experience with cultivation of bone substitutes from human mesenchymal stem cells (MSCs) derived from adult tissues and from human pluripotent stem cells and from synthesis and analysis of biomaterial scaffolds and implants. Studies in monolayer and 3D cultures onto scaffolds under static or dynamic conditions in bioreactors have shown that mesenchymal progenitors derived from pluripotent stem cells highly resemble bone marrow-derived human MSCs (BMSCs) in terms of morphology, molecular signature and bone differentiation potential, but display much higher proliferation potential and are therefore suitable for tissue engineering applications. In particular, human iPSCs can give rise to all cell types constituting the healthy bone tissue and open the possibility to engineer patient-specific bone tissue grafts substitutes for personalized applications. Highly proliferative mesenchymal progenitor cells were derived from human iPSCs (iPSC-MP; FIG. 13), and interfaced with biomimetic cement and decellularized bone scaffolds to engineer tissue grafts for basic and applied research.

Figures 14A, 14B, 14C, 14D, 14E:
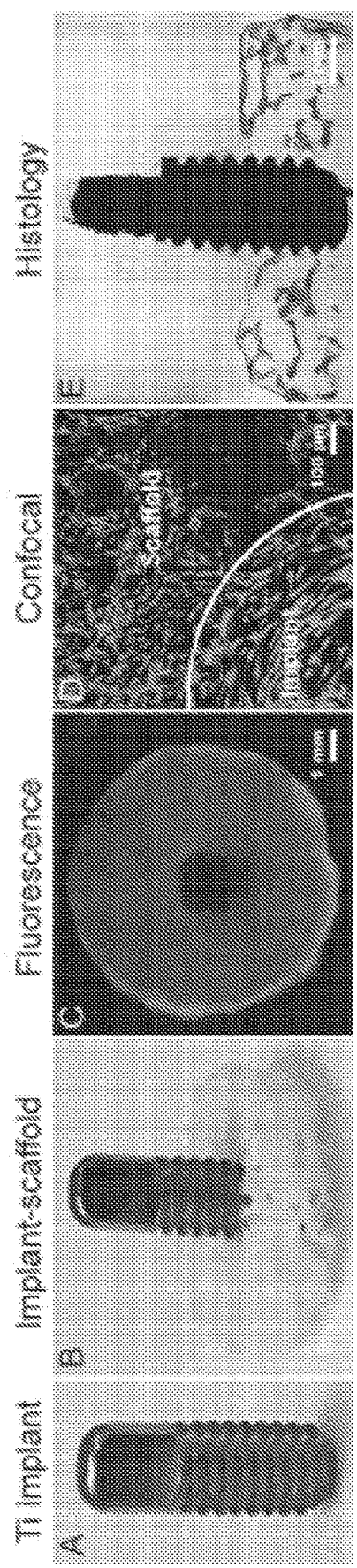
FIGS. 14A-14E are a series of representations relating to biomimetic platforms to screen implant materials.

To develop innovative research tools and reduce or fully replace animal experiments, Ti mini-implants were anchored into decellularized cow bone scaffolds, and these constructs seeded with iPSC-MP cells and cultured under osteogenic conditions for up to 7 weeks. Results using live/dead assays and histological investigations demonstrated full integration of the implant with the engineered bone graft (FIG. 14), such results can be used to engineer biomimetic platforms to screen implant materials in vitro. Studies are aimed at further developing this platform and find optimal culture conditions that increase its performance and ability to predict results obtained from in vivo studies. Calcium phosphate macroporous cement scaffolds were also developed and found to support cell attachment, proliferation and osteogenic differentiation of human iPSC-MP cells to a similar extent as decellularized bone scaffolds, and therefore may be used for engineering bone grafts for experimental and clinical applications.

The formation of a mineralized matrix at the bone-implant interface may influence the mechanical stability of the implant material in vitro, results that can be used to predict outcomes of applications in animals and patients. Differentiation of pluripotent stem cells toward some specific lineages can vary depending on the derivation method, genetic background and other factors. To cope with this inconvenient more cell lines are used, including registered lines with sequenced genome and known biology. Commercially available BMSC lines are also used to explore their potential for engineering the screening platform, and as a reference line to validate the performance of the mesenchymal progenitors derived from the different iPSC lines.

A long-term goal is to be able to screen commercially available implants and biomaterials in the screening platform. The integration of commercially available implant materials is studied in vitro and the results are compared with published data in animal models. Implants with known chemistry and topography are screened using the in vitro bone platform, and their anchoring potential is compared to results obtained from in vivo studies in animal models/patients. With the availability of an in vitro screening platform, new biomaterials could be developed and analyzed more thoroughly than has been possible using conventional extensive (and expensive) preclinical models.

Example 3

Tissue Engineering for Implantology Research—A Paradigm Shift in Biomaterial Testing Biomaterials can restore or augment tissue functionality, and are essential to the modern medical practice. In dentistry and orthopedics, prosthetic materials are used daily to treat edentulous people and patients affected by skeletal defects, with a global market worth many billion dollars every year. These devices have improved the life of numerous patients over the last decades, but are far from being optimal and in many instances fail, such as in people with poor bone quality and in the elderly. Intense research efforts are thus necessary to develop materials that are cost-effective, safe, and optimal for each patient in each clinical situation. Unfortunately, available research tools show limitations, and are becoming anachronistic in light of new breakthrough technologies. Two-dimensional (2D) methods are inherently limited because they fail to depict the typical cytoarchitecture of tissues and organs, and the cell-to-cell and cell-to-matrix interactions that are critical for cell fate control and tissue function. In addition, 2D methods preclude the possibility to study the strength of interaction between the tissue and the implant, and therefore predict the integration potential of new implant materials in patients. On the other side, animal studies are time and resource intensive, and fundamentally unreliable due to existing interspecies differences in tissue quality, physiology and metabolism. These studies are also associated with unnecessary suffering, and alternative human relevant methods are in strong demand. To overcome these limitations, and bridge the existing gap between available methods, three-dimensional (3D) tissue platforms for material testing have been developed that have the potential to revolutionize research and development in implantology, prosthetics and biomaterial science in general.

A tissue engineering approach will be used to grow functional human bone in the laboratory. The bone tissue will be grown using human induced pluripotent stem cells (iPSCs), biomimetic scaffolds, and advanced culture systems, and used to better comprehend the mechanisms leading to integration, or failure, of implant materials. Human iPSC can be derived from any patient (using, for example, small skin biopsies or a drop of blood), and represent a single cell source that can give rise to all cell types constituting the bone tissue. This will allow us to grow patient-specific bone in the laboratory, and study the biological response of any given individual to the treatments, be these new implant materials or drugs promoting tissue regeneration surrounding the implants. Human iPSCs will be differentiated into relevant cells using protocols previously established, and then combined with compliant scaffolding materials to grow personalized bone tissue. The use of scaffolding materials with tuned architectural and mechanical properties opens the possibility to mimic the bone environment typical of specific degenerative disorders, such as osteoporosis, and enables modeling of diseases in the Petri dish. To support cell growth and formation of functional bone tissue in the laboratory, tissue will be cultured in advanced chambers called bioreactors, under perfusion regimes corresponding to shear stress values typical of the native bone environment at rest or under loading conditions. It becomes evident that tissue-engineered human bone can be used as an advanced tool to study the tissue-implant interaction process under physiological or pathological conditions in vitro, and to drive the development of smarter implant materials and therapeutics, which can be individualized and exhibit broader clinical use, without the need for animal testing.

In brief, the following content is addressed: 1) Advanced Biomaterial Testing; 2) Hybrid Tissue Engineering; and 3) Personalized Medicine.

Study Overview

The overall goal of the study is to use tissue-engineered human bone for advanced testing of biomaterials. The project will contribute to the establishment of alternative methods to animal testing according to the 3Rs principle (Replacement, Reduction and Refinement). A tissue engineering approach will be used to grow functional human bone in the laboratory. Human bone will be grown using induced pluripotent stem cells (iPSCs), biomimetic scaffolds, and advanced culture systems, and use it to better comprehend the mechanisms leading to integration, or failure, of implant materials. In addition to generating an enormous amount of new data and insights on the tissue-implant interaction process in 3D, the proposed research will lead to development of personalized treatments, smarter implant materials and new therapeutics, without the need for in vivo studies and avoiding unnecessary animal suffering. Listed below are the expected outcomes of the research described.

1. Tissue Engineering for Implantology Research

Objective: To use tissue-engineered human bone for biomaterial testing. Human bone will be grown and used as an experimental platform to study the bone-implant interaction process in vitro. The inventors expect to contribute to the development of personalized treatments and new implant materials.

2. Bone-Implant Platforms for Advanced Disease Modeling

Objective: To engineer models of diseased human bone and study the bone-implant interaction process under pathological conditions. Human bone will be grown displaying typical features observed in osteoporotic patients and the causes leading to implant failure will be studied. The inventors expect to develop better implant materials and therapeutics to cope with the burden of bone deficiencies associated with global population growth, increasing longevity and the aging of the "baby boom" generations.

3. Bone-Implant Platforms for Drug Discovery Research

Objective: To engineer models of normal or diseased human bone and screen new drugs that facilitate implant integration in normal or pathological conditions. models of normal or diseased human bone (as per 1 and 2) will be grown and the effect of different drugs on the bone-implant interaction process will be studied. The inventors expect to contribute to the discovery of new drugs that are safer and more effective, and promote enhanced osseointegration of new and commercially available implants.

Hybrid Bone-Implant Grafts

Objective: To grow patient-specific bone around implants. We will interlock implants with biomimetic scaffolds (natural or synthetic), and then seed these scaffold-implant constructs with patient-specific cells to grow hybrid bone-implant grafts. We expect to develop products with enhanced therapeutic potential for complex maxillofacial and skeletal reconstructions.

Background

Every year millions of patients achieve improved quality of life through implantation of biomaterials and medical devices. Materials for skeletal reconstructions vary depending on the specific application and include metals, ceramics, and composite materials. Metals and alloys are commonly used for their good mechanical properties and ability, under favorable conditions, to form a stable bond with the surrounding tissue-osseointegration. The quality of this bond is highly dependent on the surface characteristics of the implant material at macro-, micro- and nano-scale. Yet, full integration of prosthetic implants takes time, and often fails in clinical situations characterized by poor bone quality, compromised regenerative capacity, and other factors that are still unclear. Intense research efforts are thus necessary to develop materials that are cost-effective, safe, and optimal for each patient in each clinical situation. For both creation of fundamental understanding and for safety and efficacy testing, all new implant materials need to be rigorously tested in vitro and in preclinical models. However, current methods to test toxicity and cytocompatibility in vitro display poor technical accessibility and fail to provide insights regarding the complex tissue response to the materials in 3D, as well under conditions resembling the normal or pathological environment in the human body. In conclusion, 2D methods are not sufficient to achieve full understanding of the tissue-implant interaction process. On the other side, in vivo studies are time and resource intensive, usually biased by the number of samples, and not fully reliable due to interspecies differences in tissue quality and metabolism, thus providing only a "crude indication of the biomechanical consequences in patients". Animal models also preclude the identification of genetic factors leading to insufficient implant integration or failure in at-risk patients. Therefore, in light of new breakthrough technologies, it is important to develop new testing strategies that bridge the existing gap between available methods, and facilitate research and development in biomaterial science. Tissue engineering allows researchers to grow functional tissues that exhibit features closer to the complex in vivo conditions, and may provide unique perspectives on the events occurring at the tissue-implant interface. The proposed research aims at using tissue-engineered human bone as a 3D in vitro platform to study the cellular response to the implant material, the strength of interaction of the implant with the engineered tissue, and the quality of the bone-implant interface. The technology opens unprecedented possibilities for development of smarter implant materials and therapeutics, that can be individualized and exhibit broader clinical use, without the need for animal testing.

Preliminary Results

Figure 15:
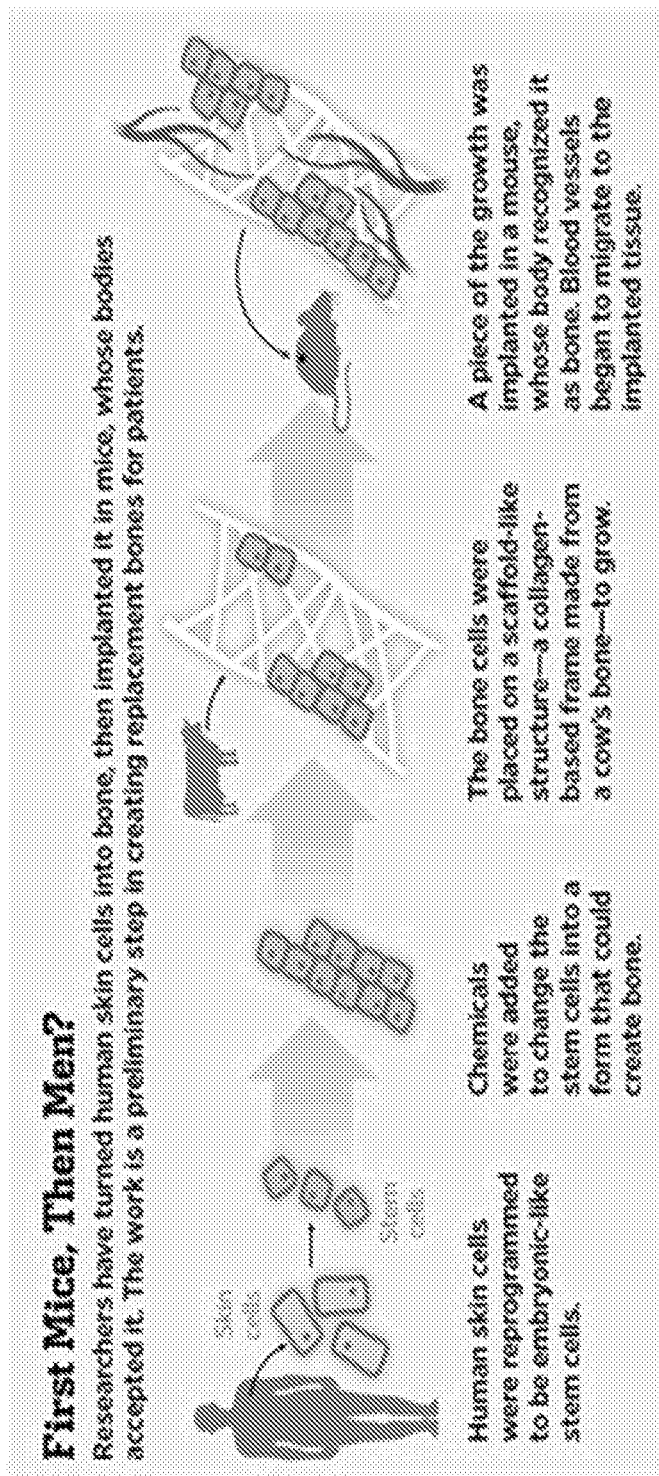
FIG. 15. Engineering bone tissue substitutes from human induced pluripotent stem cells. Human fibroblasts derived from skin biopsies were reprogrammed using non-integrating vectors. Generated iPSC lines were then induced toward the mesenchymal lineage and seeded onto decellularized bone scaffolds. The cell-scaffold constructs were cultured for 5 weeks in perfusion bioreactors, then implanted in immune-deficient mice for 3 months. Analysis of explants revealed the formation of phenotypically stable and mature bone-like tissue.

The inventors have extensive experience with cultivation of bone substitutes from human mesenchymal cells derived from adult tissues and human pluripotent stem cells, with manufacturing and characterization of biomaterial scaffolds and implants, and with design and validation of bioreactor systems. With studies in monolayer and 3D cultures onto scaffolds, under static or dynamic conditions in bioreactors, the inventors have shown that mesenchymal progenitors derived from pluripotent stem cells highly resemble mesenchymal stem cells isolated from adult tissues in morphology, molecular signature and differentiation potential. In order to engineer autologous tissue grafts, highly proliferative mesenchymal progenitor cells were derived from human induced pluripotent stem cells (iPSC-MPs), and used them to grow bone grafts using a biomimetic scaffold-perfusion bioreactor approach to bone development (FIG. 15). In particular, human induced pluripotent stem cells can give rise to all cell types constituting the bone tissue, and open the possibility to engineer physiologically complex bone grafts for personalized applications in basic and applied research, and in the clinics.

Figures 16A, 16B, 16C:
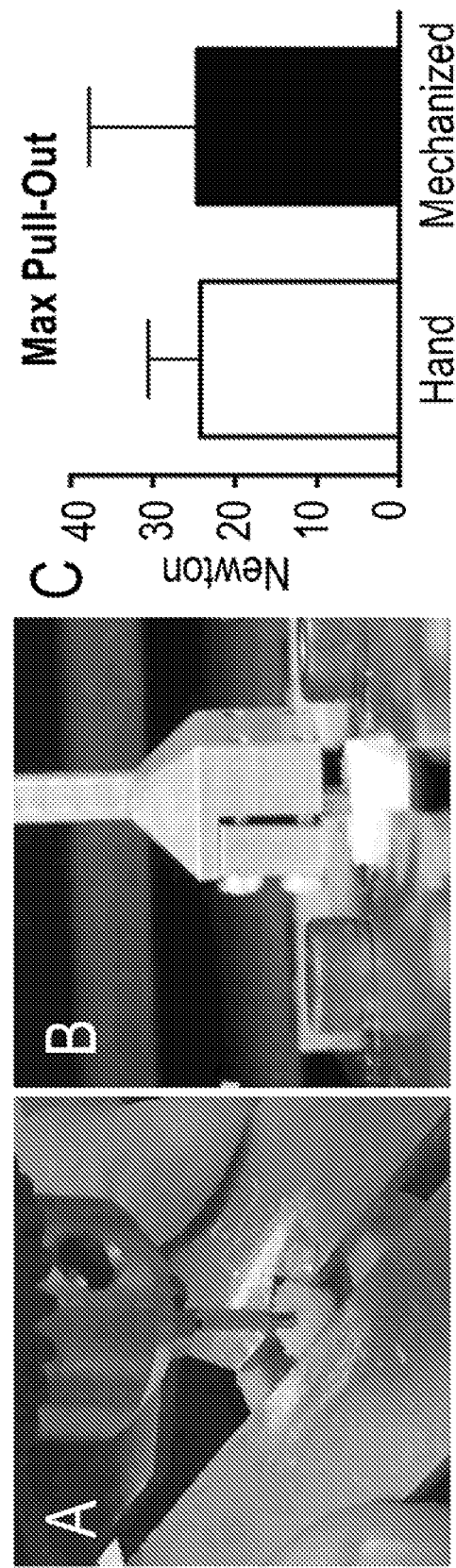
FIGS. 16A-16C are a series of images relating to implant insertion into scaffolds and mechanical stability.

In an attempt to develop innovative research tools and reduce or fully replace animal experiments, titanium implants (2 mm diameter, 6 mm height) were anchored into decellularized cow bone scaffolds (8 mm diameter, 3-4 mm height), and seeded the implant-scaffold constructs with human iPSC-MPs to grow living tissue around the implant. To interlock the implants with the scaffolds, a perpendicular thread was made in the center of the scaffold and then inserted the implants either manually or mechanically (using an electric screwdriver at a rotation angle of 2000 degrees). The implant-scaffold mechanical stability (primary stability) was studied via pullout test (FIG. 16).

Figures 17A, 17B, 17C, 17D, 17E, 17F:
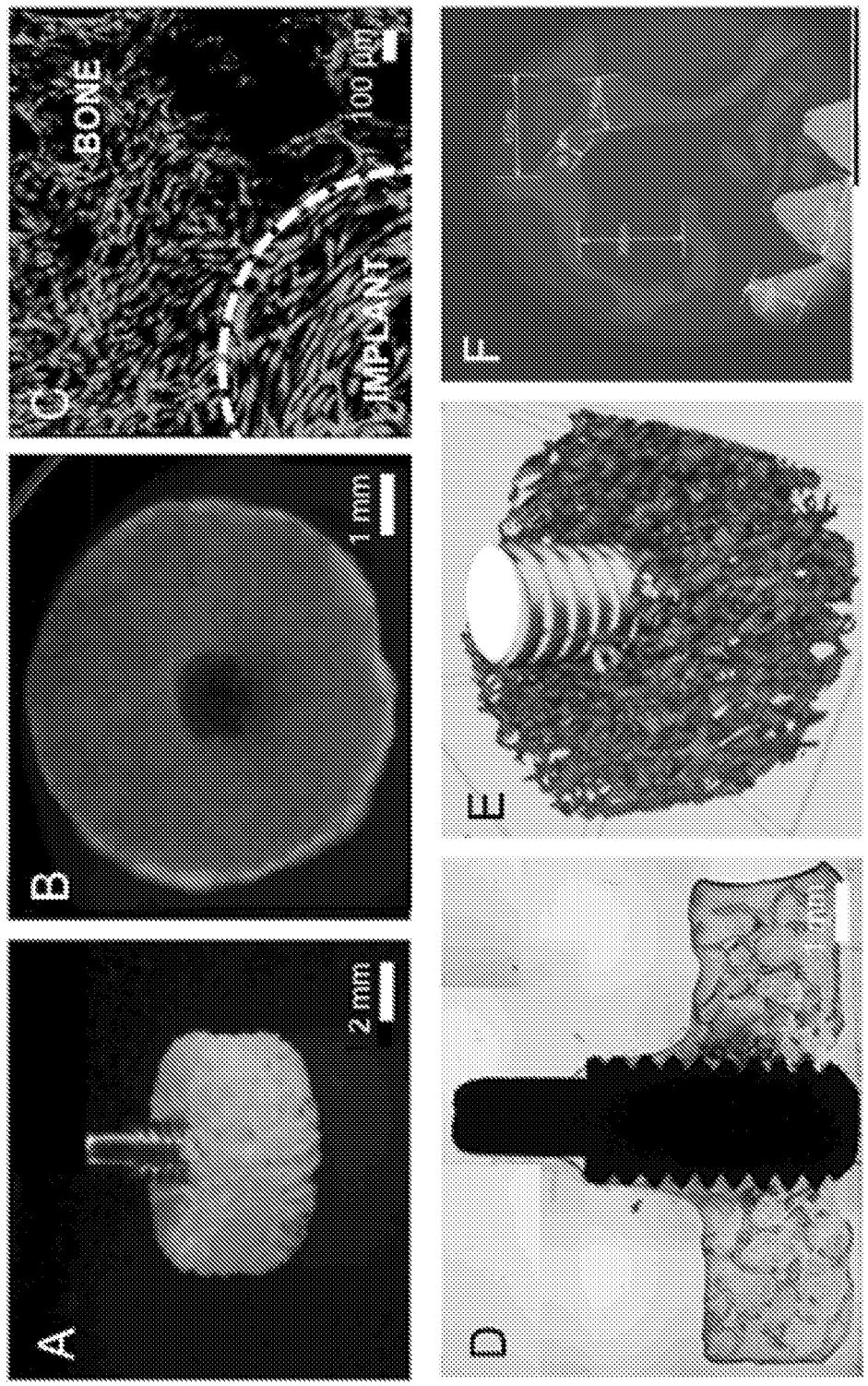
FIGS. 17A-17F are a series of images relating to a biomimetic platform to test implant materials.

Culture of iPSC-MPs on implant-scaffold constructs was documented via live/dead assays, hard histology, microcomputed tomography ($\mu$CT), and energy-dispersive X-ray spectroscopy. The results reveal good cell compatibility and tissue growth surrounding the implants in 3D (FIG. 17), highlighting the benefits that such a testing platform would provide for conducting research on implants, prostheses and biomaterials.

Project Description

Tissue-engineered human bone will be used as a 3D experimental platform (alternative to animal testing) to study the tissue-implant interaction process in vitro, understand the mechanisms leading to implant integration, and develop next-generation materials and therapeutics that can be individualized and lead to better clinical outcomes. Human bone will be grown in vitro from induced pluripotent stem cells and biomimetic scaffolds using engineering strategies previously established by the inventors.

The interaction of the implant material with the forming tissue will be assessed using a combination of molecular biology, biochemical assays, histological investigations, medical imaging procedures, high-resolution characterization techniques and biomechanical testing.

1. Tissue Engineering for Implantology Research.

Tissue-engineered human bone will be used to test implant materials. Commercially available implant materials will be tested, such as titanium and stainless steel, and the results compared with data previously published from animal and clinical testing. This will give an idea on the predictive value of the testing platform for in vivo studies. The implants will be characterized to study the chemical and topographic characteristics via profilometry, electron microscopy, and X-ray photoelectron spectroscopy (XPS). Plugs of trabecular bone (8 mm in diameter) will be drilled from the subchondral region of meta-carpal joints of calves, and remove the cellular and genetic material as previously reported (de Peppo et al., *Proc Natl Acad Sci USA,* 21; 110(21):8680-5 (2013)). Following decellularization, the scaffold will be cut to a final thickness of 3-4 mm. The density of each scaffold will be calculated and interlocked with the implants as described in FIG. 16. The scaffold-implant constructs will be CT scanned and the relationships among the scaffold features (density, porosity, contact area, etc) and the mechanical stability of the implants without cells (primary stability) will be studied. Any identified effect will be considered when measuring the strength of interaction achieved following culture of the scaffold-implant constructs with cells (secondary stability). After sterilization, the scaffold-implant constructs will be seeded with human iPSC-MPs (derived using established protocols from NYSCF and/or NIH-registered lines), and culture the samples in osteogenic conditions until maturation of functional tissue. Optimization studies will be performed and the effects of scaffold origin, cell density, and culture period and conditions on the quality of the testing platforms will be evaluated. The inventors will study cell recruitment, toxicity, proliferation, differentiation and genetic stability, as well as the content and quality of the newly formed tissue at the interface. The inventors will estimate cell proliferation weekly using the PrestoBlue™ assay. The inventors will collect the culture medium at each change to study the release of bone-specific proteins via ELISA and cytotoxicity via measuring the amount of lactate dehydrogenase. The inventors will study osteogenic differentiation by studying the expression and production/activity of bone-specific factors via real time PCR, Nanostring™ Western blot and enzymatic assays. The inventors will study genotoxicity of extracted cells via karyotyping. The inventors will study tissue formation and mineralization, with a major interest toward the bone-implant interface, via micro-CT (μCT) analysis, hard and soft histology, and immunohistochemistry. The inventors will study the biomechanical properties of the tissue-implant system, such as pullout strength and removal torque. For this to be meaningful, the testing will be standardized and evaluated for size of implants and insertion forces (torque). Importantly, the inventors will concentrate on the relation between the amount and quality of matrix formed at the interface and the strength of the tissue-implant interaction. Following pullout, the inventors will characterize the implants again via SEM, XPS and Time-of-flight Secondary Ion Mass Spectrometry (Tof-SIMS) to explore any relation between the implant surface and the quality of deposited matrix. This set of studies, in addition to providing new insights on the tissue-implant interaction process, will reveal the predictive values of the testing platform for in vivo studies. If predictive, these studies will open the possibility to pre-screen implants available on the market, and guide patients toward better treatment choices.

Synthetic scaffolds: to avoid drawbacks with biological scaffolds, including high cost and extensive processing time, the inventors will use traditional and/or additive manufacturing technologies to fabricate bone cement scaffolds with tunable shape, porosity and mechanical properties. Initially, the inventors will use a dissolving phase approach to fabricate brushite- and apatite-based scaffolds with defined chemistry and architectural features, and interlock them with implant materials as per FIG. 16. Alternatively, the inventors will place the implants in the cement paste before the setting reaction to achieve good primary mechanical stability between the scaffolds and the implants. The inventors will characterize the scaffolds for diametral tensile and compressive strength, chemistry via X-ray diffraction and XPS, and architectural features via scanning electron microscopy and μCT. Then, the inventors will seed the cells to grow the tissue and evaluate the suitability of synthetic materials for studying the tissue-implant interaction using the platform. By controlling the scaffold architecture (such as porosity, pore size and pore distribution) the inventors will be able to mimic the microenvironment of the native bone tissue that is typical of specific pathological conditions, and develop disease models in the Petri dish.

Culture in bioreactors: culture under dynamic conditions is known to promote tissue regeneration and mineralization. In order to improve the relevance of the testing platform, the inventors will culture the samples in direct perfusion bioreactors as previously described, and explore the effect of dynamic conditions on the amount and quality of the newly formed tissue. If needed, the inventors will conduct simulation studies in Comsol Multiphysics to optimize the bioreactor design and identify perfusion regimes corresponding to stresses of higher physiological relevance, i.e. shear stress values typical of the native bone environment at rest or under loading conditions. Again, the inventors will study cell recruitment, viability, proliferation, and differentiation, as well as the content and quality of tissue formed, the strength of interaction of the implant with the newly formed tissue, and the quality of the bone-implant interface as per 1).

Other cell types: when a medical device is implanted into a bone cavity or defect, a sequence of molecular and cellular events occurs at the bone-implant interface, in which inflammation, regeneration, and remodeling overlap. Yet, the basic mechanisms are still unclear and difficult to unravel using current research tools. The inventors will use the testing platform to answer these questions and better understand the biological response of different cell types to the materials in a 3D environment. The inventors will also study the contribution of each cell type during the healing process, and the molecular and biological relations existing among platelets, inflammatory cells, bone-forming cells and osteoclasts. The inventors will create co-culture systems, where cells are seeded at the same time or sequentially, to understand the good and the bad occurring in the body following implantation of a medical device. Understanding of the sequential events leading to integration will help to design implant surfaces that can control the regeneration process.

Development of new implants and biomaterials: Implant chemistry, topography and design all influence the molecular and cellular phenomena that take place at the tissue-implant interface in vivo, and research is ongoing to develop implants with higher therapeutic potential. The inventors will use the testing platform described here to develop new implants. The inventors will tune chemistry and topography of implants, and change the design, to improve their tissue compatibility and integration potential. The inventors will start with medical grade titanium implants. The inventors will modify the implants at different scale using different technologies and progressively screen implants with better surface characteristics that lead to improved healing. In particular, the inventors recently demonstrated that nanopatterning of implant materials could guide cell response in 2D systems, and will now use colloidal lithography to modify the surface of implants (both chemistry and topography) and study how these modifications affect the tissue-implant interaction in 3D. An adapted version of the testing platform will be explored to test the tissue compatibility of different types of biomaterials. The inventors will create donut-like bone grafts that can accommodate plugs of materials with select properties, and test biocompatibility, osteoinductivity and osteoconductivity under conditions never reached before. Such a system could radically change the way biomaterial research is conducted, for development of cheaper, safer and more effective biomedical materials.

2. Bone-Implant Platforms for Advanced Disease Modeling.

Osseointegration of orthopedic implants is limited in aged patients due to compromised bone structure and quality, and new solutions are required to cope with challenges posed by an aging global population. The technology described in this proposal allows us to recapitulate important aspects of the bone microenvironment in osteoporotic patients, and could help to clarify the causes leading to implant failure in the elderly. The inventors will fabricate biomaterial scaffolds (natural or synthetic) mimicking the architecture of osteoporotic bone, and then interlock them with implant materials to mimic conditions that are typical in aged patients. To simulate the poor bone regeneration properties observed in aged patients, the inventors will use senescent iPSC-MPs obtained from prolonged in vitro culture under expansion conditions. The inventors will use these models of aged bone to study the biology and the biomechanics of the tissue-implant interaction under pathological conditions. These models could lead to design of better implant materials and therapeutics for an increasing number of patients worldwide.

3. Bone-Implant Platforms for Drug Discovery Research.

New candidate drugs are first tested in vitro then in animals to assess safety and efficacy. This process involves large investments, requires long periods of time, and often fails due to inadequacy of available research tools. Development and validation of superior methods, alternative to conventional ones, is highly desired in the field of pharmaco-toxicology. The inventors will grow models of normal or diseased human bone anchoring implant materials, and study the effect of different drugs on the bone-implant interaction process. In addition to representing a potential bridge to cover the gap between existing methods for more successful drug discovery, the platform opens new horizons for accurate pharmacodynamics and pharmacokinetics studies in vitro. The inventors will attempt to simulate the effect of circulation on drug clearance culturing the samples in bioreactor systems under select perfusion regimes. The ability to construct bone-implant models of disease in 3D in the Petri dish represents a revolution in the field, and could facilitate discovery of better therapeutics in a shorter period of time.

4. Hybrid Bone-Implant Grafts.

Reconstruction of large maxillofacial defects at the interface between the skull and the teeth often requires multiple surgeries and long healing and rehabilitation times. Current treatments are deficient and can lead themselves to further complications. To provide better treatment options to these patients, we will grow anatomically shaped patient-specific bone tissue around implant materials. We will interlock dental implants (or other prostheses) with biomimetic scaffolds (natural or synthetic), and then seed the scaffold-implant constructs with patient-specific cells to grow customized bone-implant grafts in the laboratory. With the objective to increase the size of engineered tissues, we recently proposed and developed an alternative engineering strategy called segmental additive tissue engineering (SATE) as described in the international patent application No. PCT/US2014/72579.

Significance

The need for skeletal reconstructions is constantly growing and new development of implant systems are constantly ongoing in industry, academia and at research institutes. For both creation of fundamental understanding and for safety and efficacy testing, all new implant materials need to be tested in vitro and in preclinical models. However, these methods show profound limitations and can require time periods of several years with extensive costs. Tissue engineering provides new research possibilities in biomaterial science, and opens new perspectives on the way the inventors study and understand the complex interaction of medical devices with our body. The testing platform described in this work is a versatile research tool, which can be refined at will to put more light on the various mechanisms leading to integration, or failure, of implant materials. It is likely that this new technology will lead to development of more advanced treatments, without the need for animal testing.

Although the invention has been described with reference to the above example, it will be understood that modifications and variations are encompassed within the spirit and scope of the invention. Accordingly, the invention is limited only by the following claims.

What is claimed is:

1. A hybrid bone-implant graft comprising:
   a) an implant material; and
   b) an engineered bone tissue graft having a scaffold, wherein the graft is vascularized and composed of cells seeded on the scaffold and cultured in vitro with the implant material to promote the formation of a stable bond between the implant material and the engineered bone tissue,
   wherein the cells include mesenchymal progenitor cells derived from induced pluripotent stem cells and endothelial progenitor cells, and
   wherein the cells seeded on the scaffold are cultured in vitro under dynamic conditions and exhibit increased expression and deposition of collagen, osteopontin, bone sialoprotein and osteocalcin as compared to culture under static conditions.

2. The graft of claim 1, wherein the implant material comprises titanium or steel.

3. The graft of claim 1, wherein the scaffold has a thickness of from about 0.3 millimeters to about 10 millimeters.

4. The graft of claim 1, wherein the scaffold has a thickness of less than one centimeter.

5. The graft of claim 1, wherein the scaffold consists essentially of decellularized bone tissue.

6. The graft of claim 5, wherein the bone tissue is bovine bone tissue.

7. The graft of claim 5, wherein the bone tissue is human bone tissue.

8. The graft of claim 1, wherein the scaffold comprises one or more synthetic materials.

9. The graft of claim 8, wherein the synthetic material comprises ceramic, cement, polymer composite, or any combination thereof.

10. The graft of claim 1, wherein the scaffold has been functionalized.

11. The graft of claim 1, wherein the scaffold comprises one or more openings to accommodate the implant material.

12. The graft of claim 1, wherein the culturing is carried out for about 2, about 3, about 4, about 5, about 6, about 7, about 8, about 9, or about 10 weeks.

13. The graft of claim 1, wherein the culturing is carried out for more than 10 weeks.

14. The graft of claim 1, wherein the culturing is carried out in a culture vessel.

15. The graft of claim 1, wherein the culture vessel comprises a bioreactor, a spinner flask, a rotating vessel, a perfusion or compressive system, or any combination thereof.

16. The graft of claim 1, wherein the tissue graft is a bone graft.

17. The graft of claim 1, wherein the scaffold has a customized shape and/or size.

18. The graft of claim 1, wherein the scaffold seeded cells promote formation of new tissue surrounding the implant material.

19. The graft of claim 1, wherein the graft is analyzed to determine a molecular and/or biological response of the tissue to the implant material.

20. The graft of claim 19, wherein analysis comprises determining one or more of the following:
   a) integration of the implant material with the tissue graft;
   b) amount and/or quality of the tissue graft;
   c) interaction of the implant material with the tissue graft;
   d) migration of cells to and/or on and/or around the implant material;
   e) cell attachment, cell morphology, cell survival and/or cell proliferation;
   f) gene and/or protein expression and/or release in the tissue graft;
   g) strength of the interaction of the implant material with the tissue graft; or
   h) biomechanics of the implant material.

21. The graft of claim 20, wherein the analysis comprises computed tomography (CT), microtomography (microCT), microscopy, electron microscopy, scanning electron microscopy, immunohistochemistry, histology, or any combination thereof.

22. A hybrid bone-implant graft comprising:
   a) an implant material; and
   b) an engineered bone tissue graft having a scaffold, wherein the graft is composed of cells seeded on the scaffold and cultured in vitro with the implant material to promote the formation of a stable bond between the implant material and the engineered bone tissue,
   wherein the cells include mesenchymal progenitor cells derived from induced pluripotent stem cells, and
   wherein the cells seeded on the scaffold are cultured in vitro under dynamic conditions and exhibit increased expression and deposition of collagen, osteopontin, bone sialoprotein and osteocalcin as compared to culture under static conditions.

* * * * *